(12) United States Patent
Jacobson

(10) Patent No.: US 6,733,434 B2
(45) Date of Patent: May 11, 2004

(54) METHOD AND APPARATUS FOR ELECTROMAGNETICALLY RESTRUCTURING INGESTIBLE SUBSTANCES FOR ORGANISMIC CONSUMPTION

(76) Inventor: Jerry I. Jacobson, 2006 Mainsail Cir., Jupiter, FL (US) 33477

( * ) Notice: Subject to any disclaimer, the term of this patent is extended or adjusted under 35 U.S.C. 154(b) by 113 days.

(21) Appl. No.: 10/013,325

(22) Filed: Dec. 10, 2001

(65) Prior Publication Data

US 2003/0028070 A1 Feb. 6, 2003

Related U.S. Application Data

(63) Continuation-in-part of application No. 09/386,696, filed on Aug. 31, 1999, now Pat. No. 6,458,071, which is a continuation-in-part of application No. 08/986,832, filed on Dec. 8, 1997, now abandoned.

(51) Int. Cl.$^7$ ................................................ A61N 2/00
(52) U.S. Cl. .......................................... 600/9; 426/237
(58) Field of Search ......................... 600/9–15; 426/237

(56) References Cited

U.S. PATENT DOCUMENTS 4,524,079 A * 6/1985 Hofmann .................... 426/234
6,022,479 A * 2/2000 Smirnov ..................... 210/695
6,287,614 B1 * 9/2001 Peiffer ........................ 426/237
6,458,071 B1 * 10/2002 Jacobson ........................ 600/9
6,579,375 B2 * 6/2003 Beckett et al. ................ 127/58

\* cited by examiner

*Primary Examiner*—John P. Lacyk
(74) *Attorney, Agent, or Firm*—Kilpatrick Stockton LLP; Charles W. Calkins; Cynthia B. Rothschild

(57) ABSTRACT

A method for beneficially restructuring ingestible substances such as sports drinks, water, neutraceuticals, pharmaceuticals, and the like and its contents for consumption by organisms. The method is also applied to topical substances such as lotions and creams. The method involves subjecting such substances for a period of time to an electromagnetic field of a specified flux density varying from $10^{-5}$ to $10^{-21}$ gauss and a specific frequency varying from 0 hertz to 300 hertz, depending on the intended subsequent use of the substance. The specific flux density and the specific frequency is empirically determined to restructure the substances such that the substances beneficially affect the organism which has the substances incorporated into the organism's metabolism.

18 Claims, 9 Drawing Sheets

Hydrophobic Bonds

METHOD AND APPARATUS FOR ELECTROMAGNETICALLY RESTRUCTURING INGESTIBLE SUBSTANCES FOR ORGANISMIC CONSUMPTION

RELATED APPLICATIONS

This application is a continuation-in-part of application Ser. No. 09/386,696 filed Aug. 31, 1999, now U.S. Pat. No. 6,458,071 which is a continuation-in-part of application Ser. No. 08/986,832, filed Dec. 8, 1997 now abandoned. This application claims priority to the filing date of both the prior filed applications. This application is also related to U.S. Pat. Nos. 5,269,746, 6,004,257 and 6,099,459 of the same inventor as the inventor herein.

TECHNICAL FIELD

This invention relates to applying electromagnetic energy to water and other substances such as beverages, foods, neutraceuticals, pharmaceuticals, and the like (substances which are ingested or ingestible) in order to beneficially restructure such substances for consumption by organisms. More particularly, such substances are subjected to specific electromagnetic flux densities and frequencies of electromagnetic radiation in order to beneficially restructure the substance and/or its contents.

BACKGROUND OF THE INVENTION

In order to treat disease, organisms have previously been subjected to electromagnetic fields of various types, and a number of procedures involving the use of magnetic fields to treat disease have been described in various references. For example, U.S. Pat. No. 4,323,056 discloses numerous prior art patents and publications describing the use of electromagnetic materials and electromagnetic fields, e.g., lasers, microwaves and radio frequency ("RF") induced magnetic fields, in the therapeutic treatment of mammals suffering from various disease conditions. These patents and publications typically teach ingestion of magnetic materials, for example, iron oxide, in patients in conjunction with the application of a magnetic force. Ferromagnetic particles become heated as a result of the coupling thereof to the magnetic field through their dielectric and hysteresis loss, the induced heating constituting the therapeutic properties of this form of treatment.

It is believed that these prior art processes were not successful for a number of reasons. The magnetic form of iron oxide is insoluble in body fluids and in substantial concentrations may be toxic to, or rejected by, the body. In addition, in many instances the amount of heat generated by these particles was excessive and substantial unwanted injury to tissue was experienced.

Devices for applying electromagnetic energy to living tissue are also disclosed, for example, in U.S. Pat. No. 2,099,511, to Caesar; U.S. Pat. No. 2,103,440, to Weissenberg; and U.S. Pat. No. 781,448 to McIntyre. Caesar teaches applying an alternating magnetic field to a localized area, and it is also believed to rely primarily on localized heating (diathermy). Weissenberg teaches application of a low level field, and McIntyre teaches means ostensibly applying a homogeneous field to the whole body of a plant or animal, for therapeutic reasons. These patents demonstrate the interest in application of electromagnetic energy to plants and animals for therapeutic reasons, but do not teach any particular means for determining a field strength or frequency that will have any particular beneficial effects.

In connection with accelerating healing of traumatic injuries, U.S. Pat. Nos. 4,611,599 and 4,576,172, both to Bentall, U.S. Pat. No. 3,890,953 to Kraus et al., and U.S. Pat. No. 3,738,369 to Adams et al., induce particular fields for purposes of promoting growth of damaged tissue. The prior art includes a wide range of field strengths and frequencies, Bentall teaching RF frequencies and Kraus teaching power line frequencies.

In addition, U.S. Pat. No. 5,269,746, to Jacobson, the present inventor, teaches a method of therapeutically treating epilepsy and Parkinson's disease which comprises subjecting mammals suffering from these diseases to an alternating magnetic field having flux density and a frequency calculated as a function of the mass of the oncogene, target gene, messenger RNA, protein, enzyme and/or hormone. This calculation equates the energy of a current electromagnetically induced in the mammal with the gravitational energy of the target genetic material, such that a dual resonance is achieved.

Although these references may disclose certain beneficial effects of electromagnetism on organisms, they do not disclose a process whereby water, beverages, foods, neutraceuticals, pharmaceuticals, topical creams and lotions, and the like, are themselves treated with an electromagnetic field in order to beneficially restructure the substances or contents thereof. For purposes of this disclosure, such substances shall hereafter be referred to as "ingestible substances" and it is intended that such term encompass any substance which is beneficially ingested or ingestible, or topically applied to or by a living organism such as a human being, etc. such that the living organism incorporates the substance into its metabolic processes. The substances provide a life support function such as that of water, nutritional function such as food, electrolyte balancing or rehydration such as pedialyte or other beneficial therapeutic function such as neutraceuticals, pharmaceuticals, creams, lotions and the like. As noted, although the term "ingestible" is used, it encompasses absorbed or topically applied substances as skin cream and the like which are not typically ingested as food or drink but absorbed through application on the skin. Methods and devices for beneficially restructuring such substances are therefore needed, and are provided by the present invention.

SUMMARY OF THE INVENTION

According to the present invention, means are provided for calculating the flux densities and frequencies appropriate for restructuring ingestible substances and their contents, by tailoring the flux density and frequency applied to the ingestible substances for a given purpose. After determining the correct flux density and frequency to be applied to the ingestible substances for a particular application, a homogeneous electromagnetic field is applied to the ingestible substance at the prescribed levels thereby inducing changes in the physical properties of the ingestible substance.

Ingestible substances which have been subjected to Jacobson Resonance (also referred to as "restructured", "resonated" or "organized" ingestible substances) is more quickly absorbed and has improved solvency properties; i.e., it is able to resonate with more soluble matter. Therefore, restructured ingestible substances will improve the health of humans and animals through resonance derived of improved organization. The restructured ingestible substance, in particular, in the case of water will enhance the growth of fruits, vegetables, and plants in general.

Magnetization of water solvents in ingestible substances will improve the detergent capability of organisms by improving reactivity and capacity for interactivity with more soluble matter. The beneficial properties of organized ingestible substances will therefore be seen when the ingestible substance is utilized for bathing, cooking, cleaning, drinking, agriculture, medicine, veterinary medicine, cosmetics, and other applications. It is important to appreciate that in the case of such ingestible substances, a large component thereof is often water. The benefits of resonated water have been explained in co-pending parent application Ser. No. 09/386,696. It has been unexpectedly discovered that such benefits can be imparted to ingestible substances as discussed and defined herein.

The present invention, therefore provides for electromagnetic treatment of water, more preferably substances containing water (natural, spring or otherwise), with Jacobson Resonance in order to render the ingestible substance more conducive to organismic life by restructuring and clustering molecules, both water and otherwise, within the ingestible substance, thereby increasing the absorption rates, biological coherence, and cooperativity of the ingestible substance to the solute within the ingestible substance. The present invention generally includes subjecting ingestible substances to alternating and steady magnetic fields having flux densities ranging from $10^{-5}$ gauss to $10^{-21}$ gauss, and frequencies ranging from direct current ("DC" or 0 hertz) to 300 hertz.

The present invention also provides an apparatus for applying magnetic fields of the type described above to ingestible substances. The apparatus, referred to as the "Jacobson Resonator" or the "Resonator", is comprised of a signal generator, attenuator unit, a set of simplified Helmholtz coils, and an application device on which the ingestible substance to be treated is placed.

DETAILED DISCUSSION OF THE INVENTION

Figure 1:
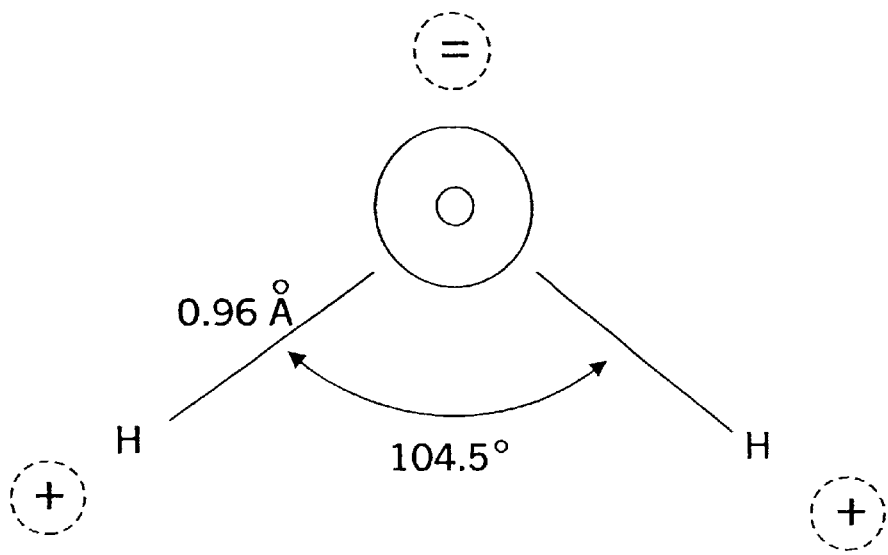
FIG. 1 shows a water molecule's angular structure.

The method of the present invention provides for electromagnetic treatment of ingestible substances, with Jacobson Resonance in order to render the ingestible substance more conducive to organismic life by restructuring and clustering molecules within the ingestible substance, thereby increasing the absorption rates, biological coherence, and cooperativity of the ingestible substance to the solute within the ingestible substance. The method generally includes resonation of ingestible substances at various flux densities and frequencies depending upon the use which will subsequently be made of the resonated ingestible substance. After resonation, the ingestible substance is thereafter applied to, or consumed by, organisms to treat disease and promote health of animal organisms and, in the case of water, for example, containing plant nutrients, is also beneficial in enhancing the growth of plants, particularly fruits and vegetables.

According to the present invention, ingestible substances are subjected to alternating and steady magnetic fields having flux densities ranging from $10^{-5}$ gauss to $10^{-21}$ gauss, and frequencies ranging from direct current ("DC" or 0 hertz) to 300 hertz. These magnetic fields recrystallize water molecules, which are constituents, particularly those water molecules with trace metals critical to the regulation of genetic information transfer. Other constituents of the ingestible substances are also believed beneficially affected, as in the case with water, particularly those with the trace metals critical to the regulation of genetic information transfer.

The invention may utilize various protocols in order to mechanically vibrate targets such as whole viruses, parts of viruses (such as the gp 120 envelope of HIV which juts into a CD4 receptor site of T-4 lymphocytes), bacterium, fungi, and other pathogens and foreign bodies. The method of the present invention impinges certain resonant frequencies upon water and other molecules in ingestible substances which are restructured and will send electromagnetic messages to macromolecules like enzymes which then change their vibrational states. The size of the seed, plant, fetus, animal and adult to which the restructured ingestible substances are applied or which are to consume the ingestible substances, changes the requirements for the signal at which the ingestible substances are resonated. After an ingestible substance is restructured, the restructured ingestible substance is subsequently supplied to an organismic system for which the ingestible substance was prepared.

An organismic system may be generally described as an aqueous solution in which water is mostly well ordered, nearly crystalline (or semi-crystalline). A polarized multilayer of water was described which can be considered to be in a quasi-crystalline state. Relative order formed "dilute salted water" in the system has entirely different mechanical, chemical, physical behaviors than the normal aqueous solutions. The important role in the living systems of "ordered water" was pointed out in the mid-1960's and was later proved.

At first, it was suggested that ordered water was as much as 50% of the total amount of water in living bodies, but systematic investigations approximated more ordered water than was expected before. One expert, for example, has suggested that at least 95% of the cell water is bonded to fully extended proteins. In other organismic systems, 75% of the cell water was found to be bonded to fully extended proteins.

Current theories teach the conventional membrane-pump model of interaction between water and cells. Pursuant to this model, the bulk of the cell water is normal liquid water, and there is little or no interaction between the bulk-phase water and cell macromolecules. It is believed that this theory is incorrect. The more accurate theory is the association-induction model proposed by Dr. G. Ling, in which the bulk-phase water in living cells exists as polarized multilayers, interacting strongly and pervasively with intracellular macromolecules; i.e., extended proteins. Of course, it is expected that a more refined polarized-multilayer theory may be developed because there is still a lack of quantitative knowledge about the structural properties of the water molecule (e.g.; the radial distribution function and the space-time correlation function). Dr. Ling's association induction hypothesis is not yet sufficiently detailed to permit a calculation of the Nuclear Magnetic Resonance ("NMR") relaxation times, as well as diffusive properties of cellular water. However, there is sufficient data about the diffusive motion of water molecules in biological systems to make two general qualitative statements: (1) within a cell, the amount of water experiencing reduced diffusive motion is substantial; and (2) the rotational motion of the majority of water molecules in a cell is reduced significantly from that of ordinary water. These principles are consistent with the present invention which is based on the interaction between water, other constituents of ingestible substances and solids within the organismic system which is treated by the restructured ingestible substance. By beneficially restructuring the ingestible substance that is supplied to the organismic system, the organismic system is beneficially affected.

It should be evident, therefore, that the present invention takes advantage of the physical properties of ingestible substances as including solvents and constituents thereof which are subject to change when macromolecular structure and/or motion is altered. These changes arise from intrinsic reorientations of biomolecular systems which are secondary to underpinning electromagnetic dispositional states and extrinsic changes in electromagnetic fields. The relationship of matter contained in the cells and the electromagnetic field to which the ingestible substances are is subjected is called superradiance.

Biological systems are held together by long range forces, namely electromagnetic forces in the ground state, i.e., the minimum energy configuration. Coulomb forces are short range forces and cannot account for the order of biosystems. Therefore, static forces acting at short distances are key-lock in type, and cannot account for the property of rigidity in matter, or account for communications in biological matter.

Body interactions are therefore not just the sum of the number of body interactions. Photons are emitted or absorbed during transition of energy states of atoms. When there are many particles in the unit volume super-radiance is the quantum result without any classical analog. Spontaneous fluctuations in atoms induce force fluctuations in other atoms which refer to phase coherence in the ground state. Photons are a commonwealth and cannot be traced back to any particular atom. Rather, photons are convicted and energy is lost. Although photon frequency decreases, photon momentum is unchanged. Photons are thus not radiated. Fields beyond a density threshold are trapped in biological matter. Photons with definite oscillations are shared among many particles. Thus, all the particles are compelled to oscillate according to the phase of the photons. The foregoing occurs as the particles of a gas move closer together.

The sides of coherence domains are the wavelengths of photons. According to the formulas:

$$(\text{wavelength})\lambda = \frac{h}{mv} = \frac{mc^2 \cdot t}{mv} \text{ and } f = \frac{mc^2}{mvl},$$

$f$ decreases as $l$ increases, that is the photons are shared by greater numbers of particles. Momentum remains the same. Energy is therefore given off as the electromagnetic field assumes a minimum energy configuration, and the photons serve as glue for the condensed system.

When the biosystem changes, photons are emitted resulting, for example, in bioluminescence. The gain of energy is proportional to density. Particles stop collapsing only when they meet the repulsive hard core forces i.e., the impenetrability of matter. The only task of this field is to keep the particles in phase without producing any work. Thus, the second principle of thermodynamics is not violated and spontaneous creation of order in the ground state occurs. Congruent and coherent oscillatory trajectories or vibrational states whether rotational and/or translational are shared by aggregations, groups, strings, or clusters of molecules e.g., water which produce the ordering and cooperativity of systems.

The earth rotates at approximately 1000 mi/hour and orbits the sun at 18.5 mi/sec and moves through the local star cluster toward the bright star Vega with the solar system at about 12 mi/sec. The local cluster of stars takes part in the rotation about the center of our galaxy at an average speed of 200 miles per second. Similarly, groups, collections, strings or polarized layers of water molecules maintain numerous frequencies of vibrational modes and relative motions simultaneously. Likewise, resonating water molecules with a variety of magnetic flux densities and frequencies will engender vibrational patterns or periodicity or clusters in sets or clusters of molecules that can be retained for some time only to interact with macromolecular complexes once ingested into a biological system as the solvent relates and communicates with solute particles thus inducing phase coherence and adjustments of electrophysiological states and biochemistry. The force between particles in a liquid or solid (condensed matter) depends upon how many particles share a common phase. Because it represents an atypical coherence domain in ingestible substances, the force between particles is directly proportional to the number of molecules as compared to the force in vacuo, where there is only a small force between a small number of molecules.

In vacuo, the dominant force is the static force, and in condensed systems the dominant force is the radiated force. Moving from the gaseous state to the liquid state the density of water is 1600 times greater, thus increasing the force between molecules accordingly. In renormalizing frequency electromagnetic field is trapped in the ground state while (mv) remains the same. When momentum (mv) is renormalized the trapped light will come out e.g., bioluminescence. Light will be emitted by biosystems (e.g. sonoluminescence) when sound waves are produced in the system. From the antinode of the stationary wave light is emitted. The frequency of the emitted light depends upon the liquid. Each liquid has its own frequency. Biosystems have many frequencies contained by the solvent. Collapsing bubbles affect temperature (a diabatic compression) in applying van der Waals equation, p molecules are excited and light is emitted.

Yet, carbonation is not the only explanation of sonoluminesence. Thousands of particles firing their photons synchronously into a short time interval in coherence domains accounts for light being emitted from a pressure wave, i.e., sound. Trapped light of superradiance is explicable through an understanding of aggregations of molecules maintaining phase coherence. Various frequencies in water and other ingestible substances with multi-polarized layers refer to collective processes. In liquids it is the electrons which move coherently. Electrons compel nuclei to stay at fixed distances, but not a fixed place in water or other ingestible substances. Solids appear when we get superradiance of nuclei.

Consider for example, two foreign molecules A and B entering into water or other ingestible substances from outside the system. In the spectra of A and B, there are frequencies $W_A$ and $W_B$ which are equal and equal to the common superradiance of water (renormalized frequency). Since the field depends upon frequency and since these molecules contain the code of recognition of frequency these molecules are not distinguishable from water. Frequency is the natural language of the molecules. The two body attraction is magnified by the larger number of particles as the water attraction in pure water or water as a constituent of ingestible substances. The attraction between A and B while in water or other ingestible substance is highly magnified. When a third molecule C is introduced into the water or ingestible substance which is unable to co-resonate with water or ingestible substance and its constituents, C does not have in its own spectrum or frequency propensity for recognition of the pattern. A and B will interact strongly while in the water or ingestible substance and not C. The chemical pattern in this way is governed by the superradiant behavior of the solvent, which is able through this mechanism to select interacting molecules on the basis of pattern recognition which is the code of frequency.

Consider, however, 3 molecules A, B and C, each one having 2 possible frequencies in their spectra. If that water has now 2 superradiances and WA=WB, A and B will interact strongly and not C. Without touching A, B and C the superradiance of water or the ingestible substance can change for example, if in this case, the equality changes between B and C and not A then WB=WC. Thus, the chemistry would suddenly change. B and C would attract strongly, and A would not attract.

In this example, A, B and C did not change at all. Rather, the water or ingestible substance changed. Since we can affect the properties of the solvent without touching the solute we can dramatically change the chemistry of the solute just by changing the frequency at which superradiance could occur. In biosystems we have ordered patterns of reactions and we can regulate these reactions by restructuring water with magnetic signals having physiologic amplitudes and frequencies for water or the ingestible substance, the selection at each given time of which molecules will interact strongly controls cooperating of systems.

When there is disease the order of biochemical maturity is altered. It is possible to reorder the pattern by introducing resonated water with codes for frequencies to restore the proper biochemistry to the biosystem. Or, in the case of giving resonated water or water containing plant nutrient to plants we may regulate the various processes that regulate growth and repair. Furthermore, in this manner of giving resonated or restructured ingestible substances such as electrolyte drinks, such as pedialyte, water and the like to biosystems we may even regulate genetic information transfer as well as the susceptibility of an organism to foreign interaction, e.g., alter the immune responses. When biological systems are poisoned, cavities increase and more light is lost.

In order to understand the present invention, one may envision a living system as an aggregation of atoms which share ubiquitous photons (quanta of light) which serve as the "glue of matter". These photons are bound in the ground state where they will remain due to the long range force of matter. Since living systems are composed of coherent charged states and cooperative systems, restructuring the solvent, namely the water, in the living systems changes the molecular vibrational frequencies of the living system itself.

It is possible to regulate the structure of ingestible substances and thereby induce critical molecules like genes, enzymes, neurotransmitters, antibodies and hormones to restructure by changing the spin angular momenta of electrons and protons with externally sourced pico Tesla range, physiologic fields. When pathophysiological states occur, there are biophotonic emissions, or the release of the radiant quanta which regulated coherence and communications. If water within cells and in tissues is organized, then the organization of water is sensitive to the physiological and pathophysiological states of cells and tissues. When ingestible substances, in particular ingestible substances with water as a constituent, are treated with electromagnetic fields corresponding to normal magnetic profiles in humans, animals and plants and ingested by these systems, there occurs systemic reorganization of superradiances: frequencies of vibrational modes through which constituents communicate to improve total function of the living system. Therefore, the consumed ingestible substance affects the solutes which it comes into contact with and vice versa. The effect is therefore multidirectional—water affecting solids and solids affecting the water. Additionally, human tissue is piezoelectric, that is mechanical vibrations are converted into electromagnetic oscillations and vice versa. Therefore, vibrational modalities of molecules of water, as well as macromolecular systems, will enhance mutual coherence domains so all the constituents of the system will be correlated as they come into contact with each other.

Consumption of organized or coherent water or ingestible substance molecules will reorganize the particles of the solute (critical molecules) to produce increase in coherence domains, improved communications between the various atomic constituents of living systems and improve health. Consumption of electromagnetically treated water therefore improves health as these ingestible substance molecules, including water molecules, take their places as solvent in the living systems.

The living process involves the gradual loss of the electron energy of incoming compounds (nutriments, foods) by a multi-step oxidation having very little energy changes in a single step. The typical metabolic energy-step is in the range of the hydrogen-bridge bond. Consequently, it is possible to rearrange the ingestible substance structure.

Water alone or as a constituent of ingestible substances is an excellent solvent, a catalyst for many chemical reactions, a good storehouse for both heat and cold, and a poor electrical conductor when pure. The unique properties of water and water in ingestible substances are based on its unusual structure and on the polarity of its molecule. Adding ions to water, for example, or constituents of ingestible substances, typically as trace metals adds to the capacity for reactivity. The water molecule's angular structure is shown in FIG. 1. The hydrogen atoms are about 1 angstrom unit away from the oxygen atom, bound to it by covalent bonds. Each covalent bond is due to the mutual sharing of a pair of electrons between each hydrogen and the oxygen. However, the sharing is unequal because an oxygen atom is considerably more electronegative than a hydrogen atom. The oxygen atom is able to pull both electron pairs much closer to it. The oxygen has a partial positive charge. Although the water molecule as a whole is electrically neutral, it is highly polar: that is, it has a negatively charged pole (at the oxygen atom) and a positively charge pole (centered between the hydrogens). The polarity results from the bent shape of the molecule and the distribution of electrical charges within it.

Figures 2A, 2B:
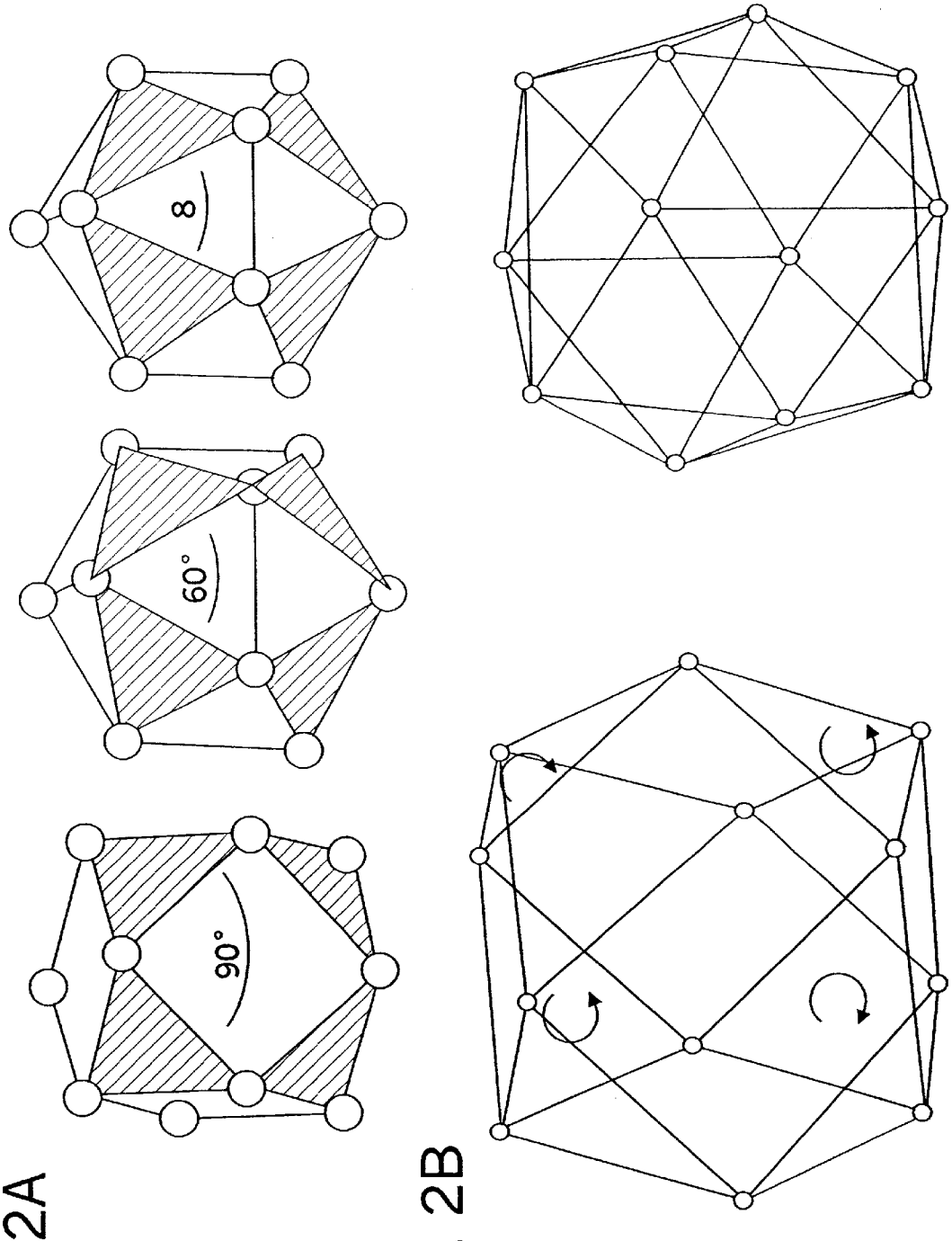
FIG. 2 shows water states in living systems.

FIG. 2 represents water states in living systems. It also shows geometrical frustration in three dimensions, where (a) breathing like, and (b) tilting like, changes the icosahedral cluster. Note that we may change the physical properties, for example the dielectric constant, of a material; e.g., water, without changing the composition (only the microscopic ordering) of the medium itself.

Figure 3:
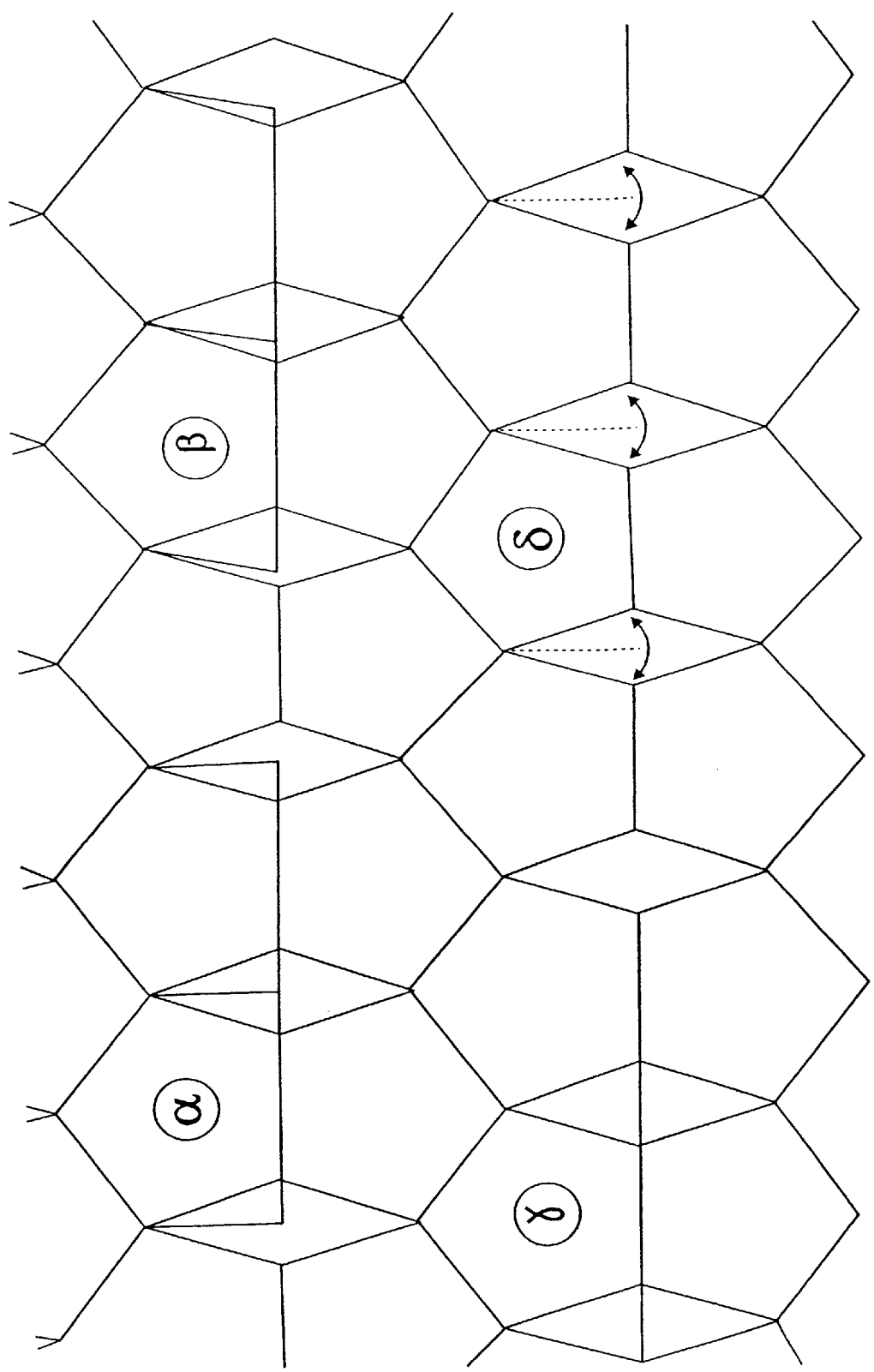
FIG. 3 shows the dynamic solution of the tessellation by regular pentagons: α β an δ are possible distortions of the five fold symmetry, thus becoming non-regular units. With δ the five fold symmetry is kept.

FIG. 3 shows the dynamic solution of the tessellation by regular pentagons: $\propto \beta$ and $\gamma$ are possible distortions of the five-fold symmetry, thus becoming non-regular units. With $\gamma$ the regular five-fold symmetry is kept; the geometric frustration causes the units to vibrate (if these units are composed of water, the hydrogen bridges will vibrate).

Figure 4:
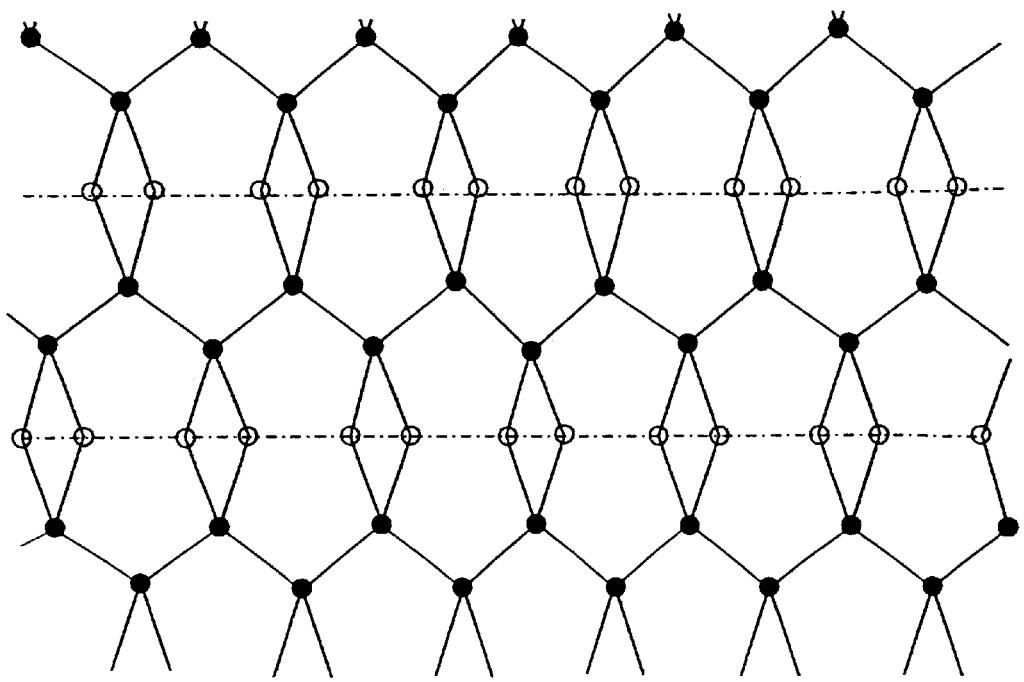
FIG. 4 shows the proper tessellation on the plain sheet by non-regular pentagons.

FIG. 4 shows the proper tessellation on the plain sheet by non-regular pentagons. Ordered states of water reveal coherence in the domains of the quantum world as subatomic particles move in relative translational and rotation modes which are dependent upon the elementary electrical charges which comprise the electromagnetic field—matter.

Figure 5:
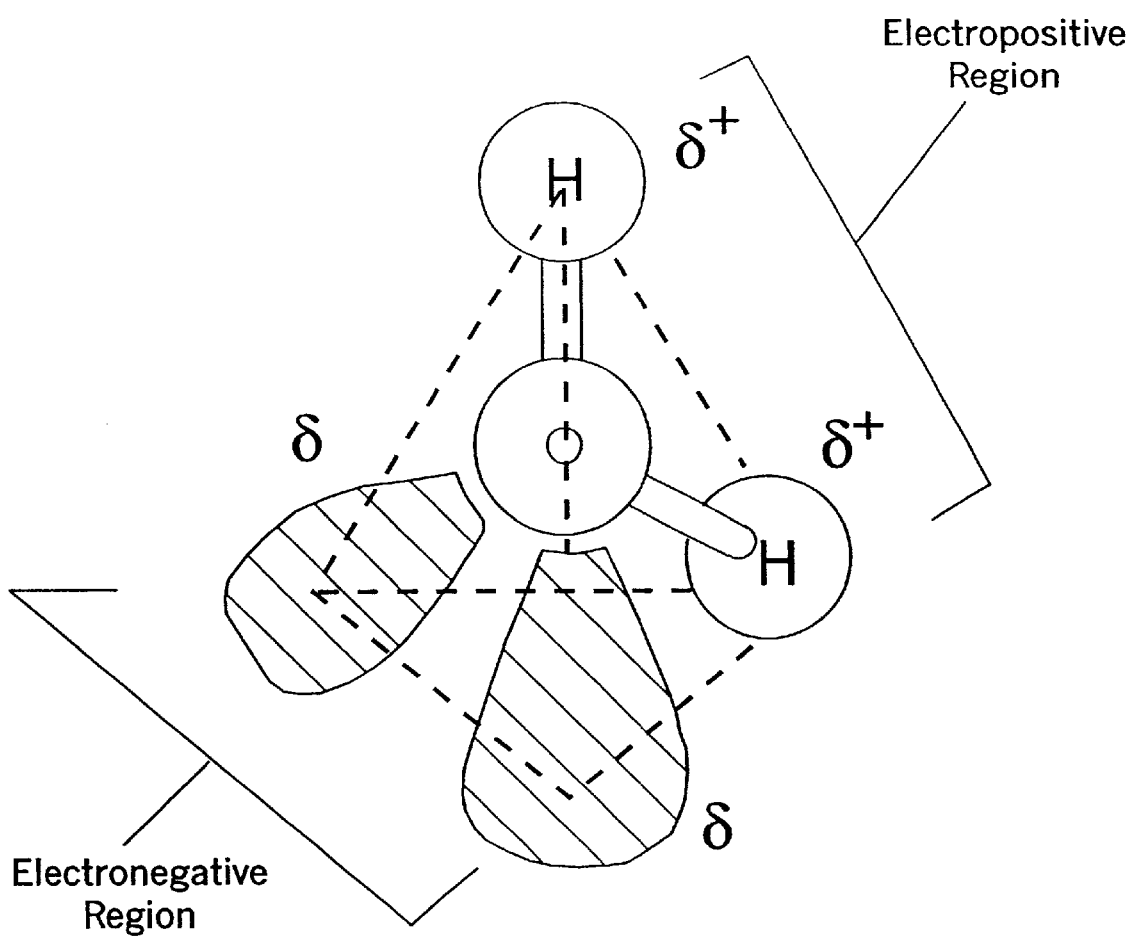
FIG. 5 shows the peculiar structure of water as a quasi-crystalline polymeric structure: wherein the molecules are permanent dipoles which join labily creating a network of hydrogen bonds.
Figure 6:
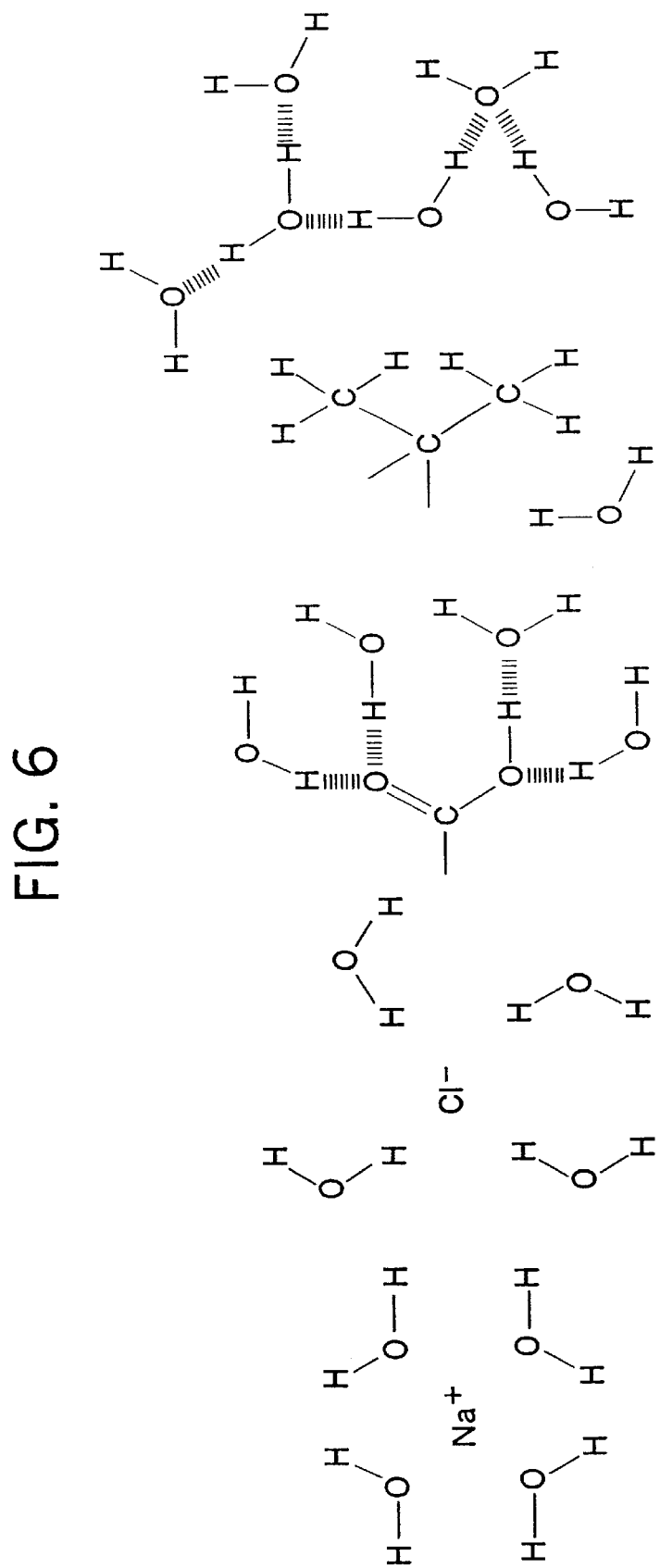
FIG. 6 illustrates that a water molecule, including water in ingestible substances, joins another four forming a constantly changing short lived polymeric highly cooperative structure. Additionally, it shows that polarity makes water molecules cluster around ions. Polar molecules are therefore also hydrophile and hydrosoluble.

The solid and aqueous phases of the cytoplasm are the meeting point between biochemistry and biophysics. Water, which includes free water in the cytoplasm, has a peculiar structure, a quasi-crystalline polymeric structure: all its molecules are permanent dipoles which join labily creating a network of hydrogen bonds. FIGS. 5 and 6 show that at 37° C. every water molecule joins another four forming a constantly changing short lived polymeric highly cooperative structure.

Although hydrogen bonds continuously form and disrupt, they give the 'water polymer' a high level of cohesion, which in turn displays certain characteristics—such as high surface tension, high specific heat, and high vaporization heat. Water has a high dielectric constant (E–80 at 20° C.) which is correlated to the refraction index and to a high absorption of infrared and microwaves. In ice, which is highly structured water, the dielectric constant is extremely low (E=5).

Water is a statistic assembly of five types of molecules which form 0, 1, 2, 3, or 4 hydrogen bonds per molecule. In this model the hydrogen bonds form and then disrupt and bending must be considered.

Theories on the structure of water postulate the existence of molecular clusters or aggregates. This hypothesis is consistent with the dielectric behavior, which is property pertaining to molecular clusters rather than to single molecules. $H_2O$ molecules connected by hydrogen bonds aggregate in clusters which have an extremely short mean life ($10^{-10}$–$10^{-11}$ sec.).

Polarity makes water molecules cluster around ions ($Na^+$ and $Cl^-$) and other polar molecules (—COOH) and establish hydrogen bonds with them. Polar molecules are therefore also hydrophile and hydrosoluble (FIG. 6). Apolar molecules break the network of hydrogen bonds, they are hydrophobic and insoluble. They tend to isolate themselves from surrounding water by forming hydrophobic interactions which play a very important functional role.

As well as reacting with ionizing radiation (forming radicals and peroxides), water interacts with non ionizing radiation to produce various conformational changes which are determined by charge distribution, motions of aggregations of clusters of water molecules through space and time, and coherent communications between water and its contained ponderable bodies.

Water forces the hydrophobic groups to aggregate or cluster to minimize the disruptive effect they could have on the H bond network. When hydrophobic groups associate like this, it is often said they are aggregated by "hydrophobic bonds".

Figure 7:
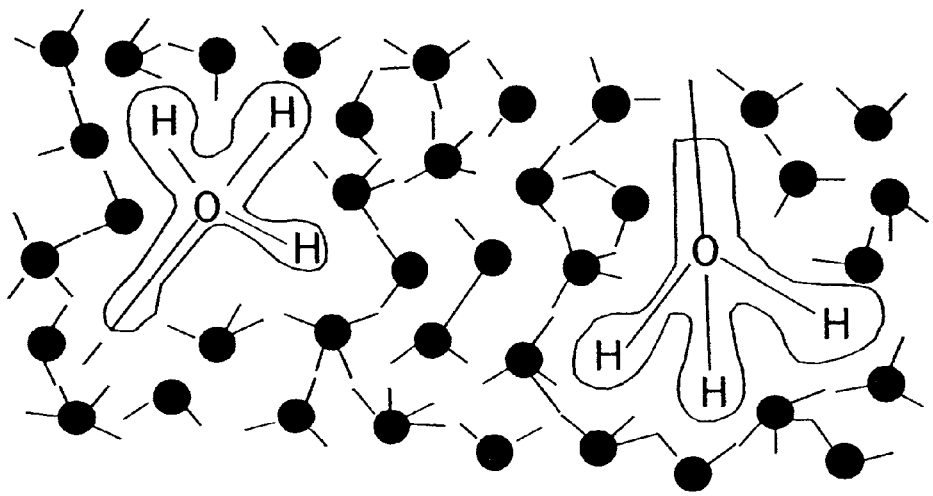
FIG. 7 illustrates hydrophobic interactions linking molecules.
Figure 7:
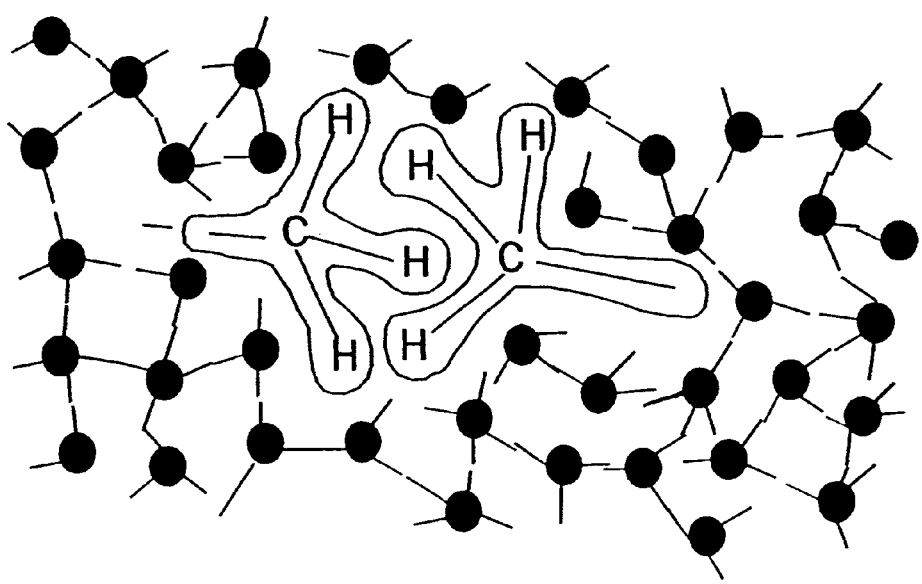

As seen in FIG. 7, hydrophobic interactions can link molecules (hydrophobic bond). Two or more hydrophobic groups tend to isolate from surrounding water with its polymeric like structure. This mechanism is the possible cause of enzyme-enzyme and enzyme-filament interactions in the sheet of structured water adjacent to the solid state protein structures.

The traditional interpretation whereby intracellular water was seen to have the same characteristics as free water has been reviewed: several experiments prove that a large fraction of intracellular water has properties which differ from those of the pure liquid. Biophysically cytoplasm is considered a gel, consisting of a rich dynamic network of interconnected filaments that give the cytoplasm that stiffness and elasticity without hindering its fluid character.

The relationship between the filament structures of the cytoplasm and water have been studied. We see the cytoskeleton as a solid state dynamic reticulum with a very vast surface, estimated at about 70–90 billion sqnm per cell. Clegg was able to prove experimentally while using several techniques that the water surrounding the cytoskeleton is ordered; that is aligned with polar links on the surface of the proteins. Consequently this means that each cell has a very thin layer of ordered water extending over at least 3 nm from the billions sqnm of solid state surfaces.

We believe through a dipolar mechanism this water can be coupled to the coherent dynamics of the protein solid state, protecting it from thermal dissipation and thus creating favorable conditions for the protein filaments to carry signals.

Biophysicists currently view hyaloplasm (that is MT reticulum+water) as a highly ordered and structurally coherent reticulum of dynamic protein polymers which is closely connected to ordered water through a vast surface; it has a lower level of entropy and a lower dielectric constant compared to the free water far from the reticulum surface.

The biological importance of the juxtafilament structured water becomes apparent when considering the well based hypothesis that all metabolic activities take place on the surface or near the surface of cell ultrastructures, because this means that enzymes operate in a microenvironment which is different from a diluted aqueous solution.

Of the relaxation processes of excited atoms and molecules one must consider fluorescence, or radiative relaxation, which is quick de-excitation with emission of a photon whose energy is less than that of the incident radiation. Excited molecules can relax by means of a chemical reaction with other excited or non-excited molecules, yielding free radicals, biradicals or stable molecular products. Excited molecules can transfer their excitation energy to other molecules through non-radiative processes (excitons, conformational variations) as well. They can also de-excite in a non-radiative mode by internal conversion of excitation energy into mechanical or vibrational energy which is our goal in utilization of physiologic magnetic fields i.e., the production of stable, balance and hemostatic products and processes.

Living systems must be regarded as a unit, since their properties cannot be additively composed from the properties of its parts, and it is not possible to divide living systems into parts carrying the properties of the system. The living reactions are special processes which are cooperative, collective phenomenon expanded over the whole living unit (protein, cell, etc.) depending on the level of the interaction. The cooperativity in the living state is the essence of the phenomenon. Some synchronized effects characterize life (for example, the growth or the dividing of cells) which have to have a general controller in the system. Some cooperative mechanisms have been ascribed to the living state, e.g., chemical, solid-state electronic and ionic transfer, as well as fractional charge-transfer. These phenomenon have succeeded in explaining different special proteins (e.g., enzymes) or whole cells. As another example, ionic concentration (pK) has also been introduced governing and explaining the collectivity of some special process.

The first suggestion of a solid-state type electronic process in living systems as one of the possible collectivity in proteins and DNA was made by Szent-Gorgyi in 1941. An early calculation strongly suggested the existence of a conduction band in proteins. This was later proven experimentally by observing a semi-conductive behavior with a forbidden gap of 2–3 eV. The measured conductivity in wet proteins (there is no effect in dry proteins) supports this conclusion.

The protocol which the water (or other material to be realigned for ingestion into the body of a human, or, abrasion to the body of a human such as a material; e.g., cotton) must be exposed to electromagnetically is determined by the physiologic nature of the signal. That is, the field impinged upon the water molecule, ingestible substances, trace metal, foreign body; e.g., virus, clothing material, cosmic construction block, etc., should be that field which the target element in vivo must experience to maintain order, coherence, cooperativity and coherent oscillatory trajectories of particulate matter composing the body thereto.

The electromagnetic field, focusing upon the magnetic component of the signal may be created by a solenoid, helmholtz coil, plates, free flowing electrical current magnetic components, poloidal magnets, toroidal coils and any other means of producing a homogeneous, isotropic magnetic field to therein induce changes in spin angular momenta of leptons and baryons, thus causing changing magnetic moments, and crystalline restructuring. Since the atoms are spinning permanent magnets, they are susceptible to reorientation by extrinsically sourced magnetic forces. Solenoids and helmholtz coils, plates, poloidal magnets, toroids, free electrical currents all may produce the appropriate EM signals. A solenoidal exposure system or a helmholtz coil exposure system is acceptable to produce a homogeneous isotropic magnetic field to therein rearrange the water molecule, ingestible substances, and/or water and other specific constituents of the ingestible substance itself; i.e., the particles that comprise the atoms that may themselves participate in changing charge densities and cooperativity between changing systems or kinetic systems such as our universe.

Figure 8:
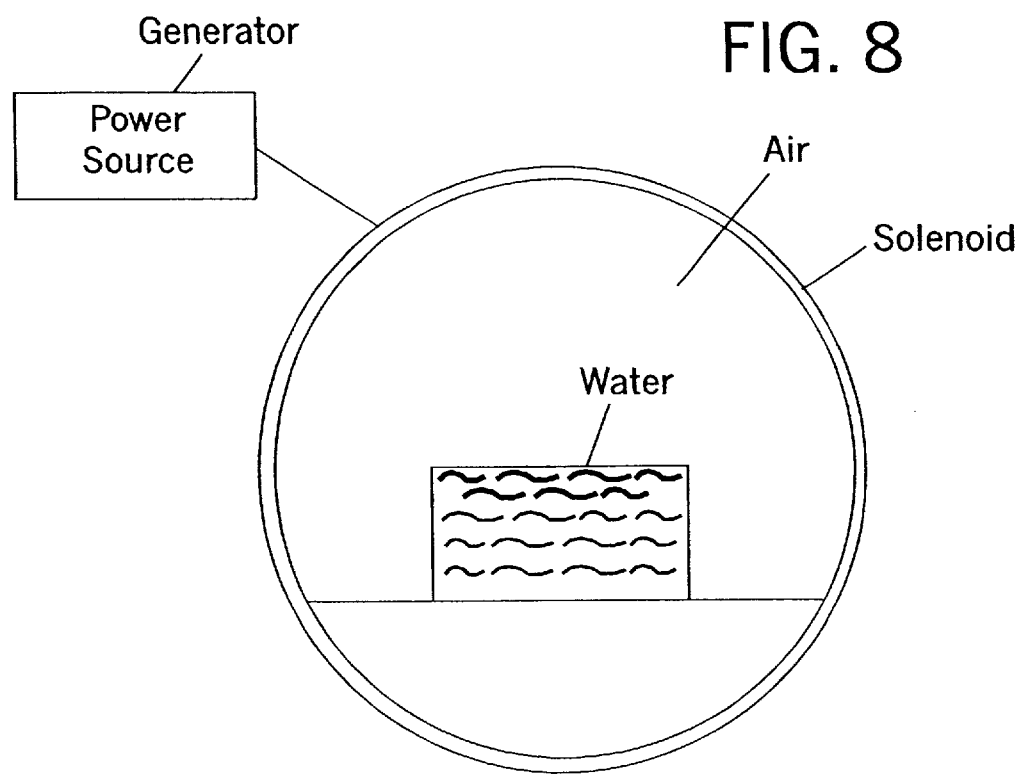
FIG. 8 illustrates a solenoidal system magnetizing water molecules, preparing the structured water in ingestible substances for human consumption.
Figure 9:
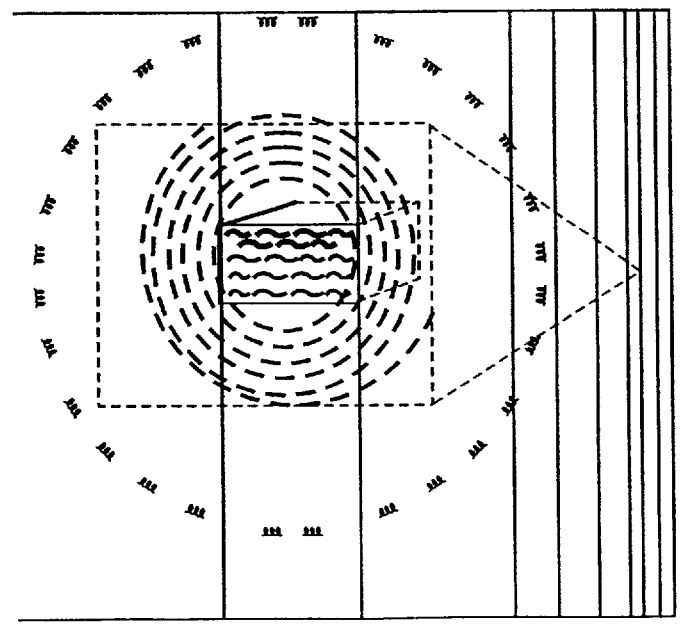
FIG. 9 is a diagram of the effect of the field on the motion of water.
Figure 10:
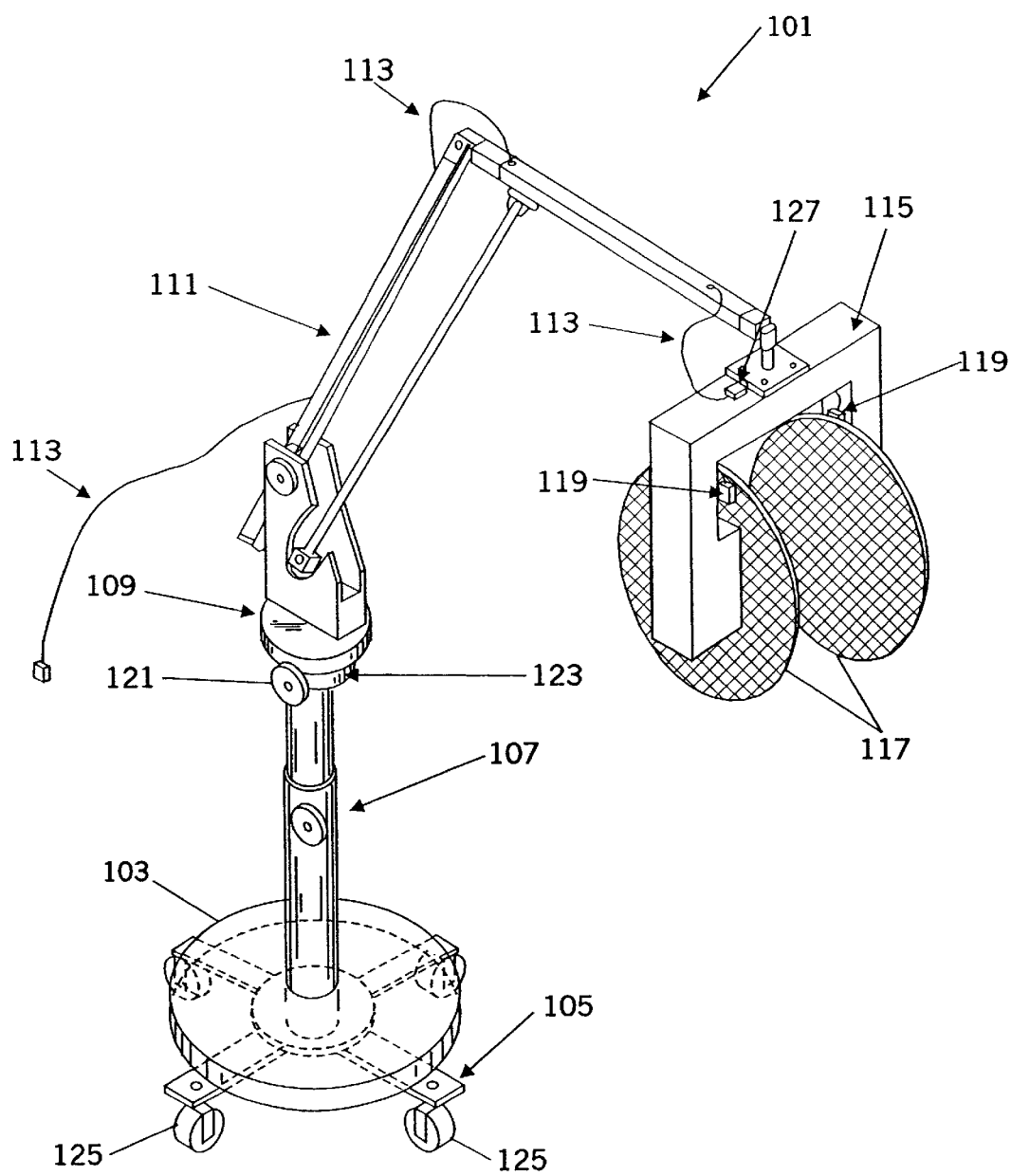
FIG. 10 is a perspective view of the support stand and application device of the Jacobson resonator.
Figure 11:
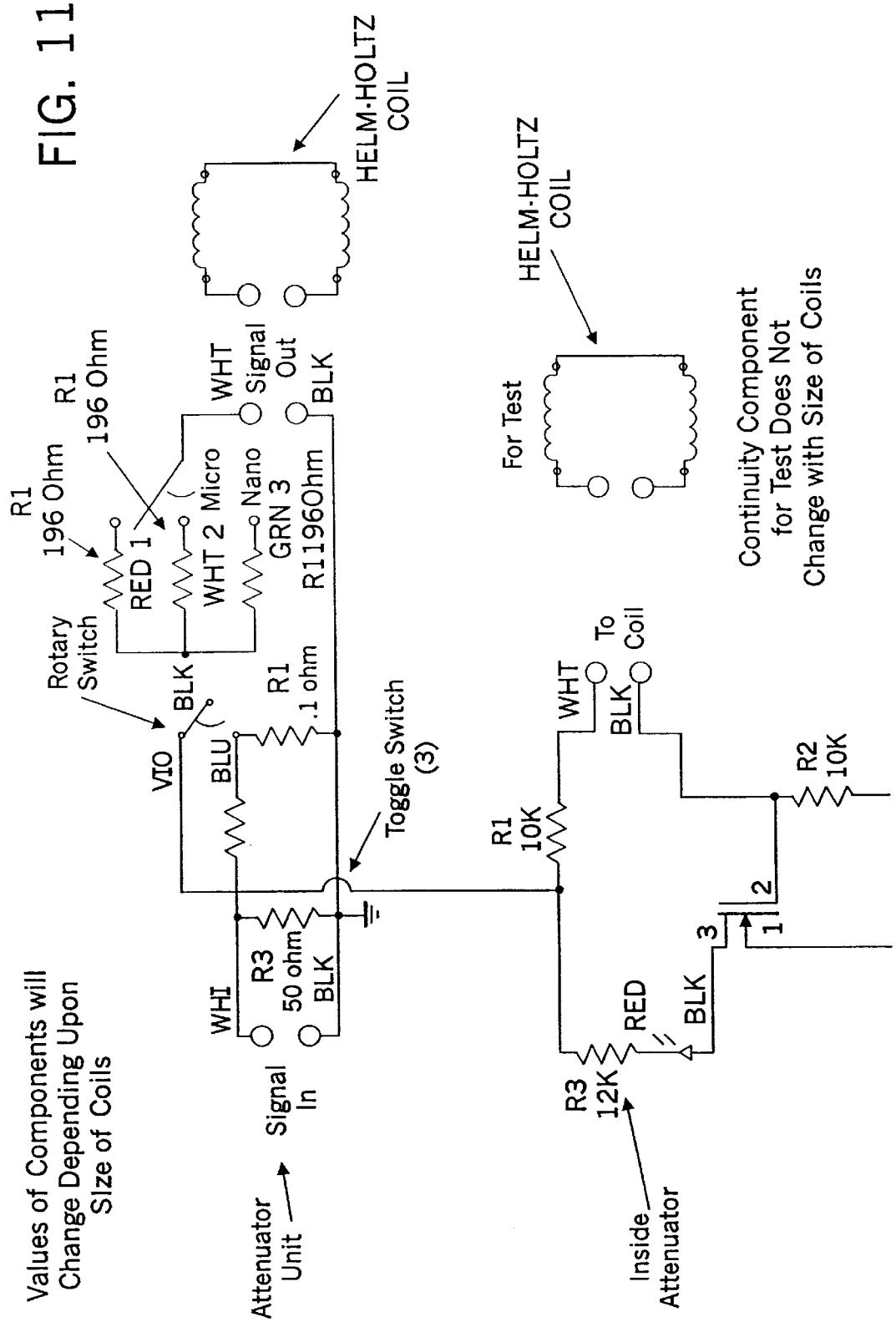
FIG. 11 is a schematic of the basic circuit of the Jacobson resonator.

FIG. 8, for example, shows a solenoidal system magnetizing water molecules, preparing the structured water for human consumption. The levels of magnetization are provided in Tables 1, 2 and 3 below. The Jacobson Resonator, described in detail below, produces such an electromagnetic field, and it is preferred to use the Jacobson Resonator to create and control the electromagnetic fields to which the water is subjected.

TABLE 1

Critical molecules used in calculating the amplitude and frequency or desired magnetic field.

| | Critical Molecules | Intensity, B (Gauss) | Freq., F (Hz) | Length, L* (cm) | Velocity, V# (cm/s) |
|---|---|---|---|---|---|
| 1 | Spectrin, Brain Specific Fodrin | $1.0 \times 10^{-5}$ | 0.15 | ML | SS |
| 2 | Neurofilaments, L-70kb, Hemoglobin, MAP-70kd | $2.5 \times 10^{-6}$ | 71.0 | ML | EO |
| 3 | Interferon, Leukotrines, Platelet Derived Growth Factor (PDGF) | $1.3 \times 10^{-6}$ | 36.0 | ML | EO |
| 4 | Nerve Growth Factor (NGF), Kinesine | $9.97 \times 10^{-7}$ | 27.9 | ML | EO |
| 5 | Motor Proteins | $9.0 \times 10^{-7}$ | 25.2 | ML | SC |
| 6 | Microtubule Associated Protein (MAP) 2a, 2b | $8.25 \times 10^{-7}$ | 23.0 | ML | SC |
| 7 | Melatonin, Calmodulin, Spectrin, Brain Specific Fodrin | $7.0 \times 10^{-7}$ | 19.0 | ML | SC |
| 8 | IgE | $6.2 \times 10^{-7}$ | 17.4 | ML | SC |
| 9 | Neurofilaments, Calmodulin | $5.7 \times 10^{-7}$ | 16.0 | ML | EO |
| 10 | IgG, Epinephrine | $4.6 \times 10^{-7}$ | 12.8 | ML | ER |
| 11 | Tubulin αβ dimer | $3.4 \times 10^{-7}$ | 3.6 | ML | SC |
| 12 | IgM (900KD), Dopamine, Norepinephrine, Homeoboxes | $2.7 \times 10^{-7}$ | 7.6 | ML | SC |
| 13 | Neurofilaments L-70KD | $2.1 \times 10^{-7}$ | 5.6 | ML | SC |
| 14 | MAP, G-actin, Calcium ion, Microtubule, Tubulin globular monomer | $1.75 \times 10^{-7}$ | 5.4 | ML | SC |
| 15 | Potassium, Bone Growth Factor (BGF) | $1.5 \times 10^{-7}$ | 4.1 | ML | SC |
| 16 | GAP, Homeoboxes, Iron | $1.26 \times 10^{-7}$ | 3.5 | ML | ER |
| 17 | Serotonin, Interferon, Platelet Derived Growth Factor (PDGF) | $9.0 \times 10^{-8}$ | 2.5 | ML | SC |
| 18 | NGF | $7.5 \times 10^{-8}$ | 2.1 | ML | SC |
| 19 | Calmodulin, Profilin | $5.0 \times 10^{-8}$ | 1.4 | ML | SC |

TABLE 1-continued

Critical molecules used in calculating the amplitude and frequency or desired magnetic field.

| Critical Molecules | Intensity, B (Gauss) | Freq., F (Hz) | Length, L* (cm) | Velocity, V[#] (cm/s) |
|---|---|---|---|---|
| 20 ATP | $3.4 \times 10^{-8}$ | 0.952 | ML | SS |
| 21 Epinephrine, Serotonin | $3.4 \times 10^{-8}$ | 0.952 | HL | SS |

Table 1: Magnetic field intensities (B) calculated from Eqn (1), and frequency (f) from Eqn (2) using the mass (m) of critically important molecules (total of 14 settings). Note B- and f-values with were calculated by the use of length (l) mice ML, and four different velocities (v): They are: EO earth orbital velocity, ER earth rotational velocity, SS solar system velocity, and SC local star velocity.
[#]In calculating the magnetic field intensities and frequencies from Equation (1), four different velocities were used. They are Earth Orbital (EO), Solar system (SS), Earth Rotation (ER), Local Star Cluster (SC).
*All of the B- and f- values were calculated using length of mice (ML), except for enpinephrine and serotonin, which was calculated from the length of human (HL).

TABLE 2

| Critical Molecules | Intensity, B (Gauss) | Freq., F (Hz) | Length, L* (cm) | Velocity, V[#] (cm/s) |
|---|---|---|---|---|
| Motor protein | $9 \times 10^{-7}$ | 25.2 | ML | SC |
| IgE | $0.2 \times 10^{-7}$ | 17.4 | ML | SC |
| Neurofilaments | $2.1 \times 10^{-7}$ | 5.6 | ML | SC |
| NGF | $7.5 \times 10^{-8}$ | 2.1 | ML | SC |
| Calmodulin, Profilin | $5 \times 10^{-8}$ | 1.4 | ML | SC |
| ATP | $3.4 \times 10^{-8}$ | 0.952 | ML | SS |
| Epinephrine, Serotonin | $3.4 \times 10^{-8}$ | 0.952 | ML | SS |

Additional magnetic field intensities (B) calculated from Equation (1), and frequency (f) from Eqn (2) using mass (m) of critically important molecules (total of 20 settings when these 8 are added to 14 settings in Table 1). Note these B- and f-values were calculated with the use of length (l) of mice ML, length (height) of human HL, and two different velocities: They are: SC local star cluster velocity and SS solar system velocity.

TABLE 3

Table For Humans (Length = $1.7 \times 10^2$ cm)
Inertial Velocities:
$3.22 \times 10^7$ cm/s  star cluster (SC)
$2.98 \times 10^6$ cm/s  earth orbital (EO)
$4.642 \times 10^4$ cm/s  rotational earth (ER)

| B (microgauss) FIELD | (Hertz) FREQUENCY | target masses in (daltons) EO | target masses in (daltons) SC |
|---|---|---|---|
| 0.001 | 0.028000001 | 339.321 | 3619.424 |
| 0.002 | 0.055000001 | 678.642 | 7238.848 |
| 0.003 | 0.084000002 | 1017.963 | 10858.272 |
| 0.004 | 0.112000002 | 1357.284 | 14477.696 |
| 0.005 | 0.140000030 | 1696.605 | 18067.120 |
| 0.006 | 0.168000003 | 2036.926 | 21716.544 |
| 0.007 | 0.196000004 | 2375.247 | 25335.968 |
| 0.008 | 0.224000004 | 2714.568 | 28955.392 |
| 0.009 | 0.252000005 | 3053.889 | 32574.816 |
| 0.010 | 0.280000006 | 3393.210 | 36194.240 |
| 0.011 | 0.308000006 | 3732.531 | 39813.664 |
| 0.012 | 0.336000007 | 4071.852 | 43433.088 |
| 0.013 | 0.640000070 | 4411.173 | 47052.512 |
| 0.014 | 0.392000008 | 4750.494 | 50871.936 |
| 0.015 | 0.420000008 | 5089.815 | 54291.360 |
| 0.016 | 0.448000009 | 5429.136 | 57910.784 |
| 0.017 | 0.478000010 | 5768.457 | 61530.208 |
| 0.018 | 0.504000010 | 6107.778 | 65149.632 |
| 0.019 | 0.532000011 | 6447.099 | 68769.058 |
| 0.020 | 0.560000011 | 6786.420 | 72388.480 |
| 0.021 | 0.588000012 | 7125.741 | 76007.904 |
| 0.022 | 0.618000012 | 7465.062 | 79627.328 |
| 0.023 | 0.644000013 | 7804.383 | 83246.752 |
| 0.024 | 0.372000013 | 8143.704 | 86866.176 |
| 0.025 | 0.700000014 | 8483.025 | 90485.600 |
| 0.026 | 0.728000015 | 8822.346 | 94105.240 |
| 0.027 | 0.756000015 | 9161.667 | 97724.448 |
| 0.028 | 0.854000016 | 9500.988 | 101343.872 |
| 0.029 | 0.812000016 | 9840.309 | 107963.296 |
| 0.030 | 0.840000017 | 10179.630 | 108582.720 |
| 0.031 | 0.868000017 | 10518.951 | 112202.144 |
| 0.032 | 0.896000018 | 10856.272 | 115821.568 |
| 0.033 | 0.924000018 | 11197.593 | 119440.992 |
| 0.034 | 0.952000019 | 11536.914 | 123060.416 |
| 0.035 | 0.980000020 | 11876.235 | 126679.840 |
| 0.036 | 1.008000020 | 12215.656 | 130299.264 |
| 0.037 | 1.036000021 | 12554.877 | 133918.888 |
| 0.038 | 1.064000021 | 12894.198 | 137538.112 |
| 0.039 | 1.092000022 | 13233.519 | 141157.538 |
| 0.040 | 1.120000022 | 13572.840 | 144776.960 |
| 0.041 | 1.148000023 | 13912.161 | 148396.384 |
| 0.042 | 1.176000024 | 14251.482 | 152015.808 |
| 0.043 | 1.204000024 | 15690.803 | 155835.232 |
| 0.044 | 1.232000025 | 14930.124 | 159254.658 |
| 0.045 | 1.260000025 | 15269.445 | 162874.080 |
| 0.046 | 1.288000026 | 15608.766 | 166493.504 |
| 0.047 | 1.316000026 | 15978.087 | 170112.928 |
| 0.048 | 1.344000027 | 16287.408 | 173732.352 |
| 0.049 | 1.372000027 | 16626.729 | 177351.776 |
| 0.050 | 1.400000028 | 16966.050 | 180971.200 |
| 0.051 | 1.428000029 | 17305.371 | 184590.624 |
| 0.052 | 1.456000029 | 17644.692 | 188210.048 |
| 0.053 | 1.484000030 | 17984.013 | 191829.472 |
| 0.054 | 1.512000030 | 18323.334 | 196448.896 |
| 0.055 | 1.640000031 | 18662.655 | 199068.320 |
| 0.056 | 1.568000031 | 19001.976 | 202687.744 |
| 0.057 | 1.596000032 | 19341.297 | 206307.168 |
| 0.058 | 1.624000032 | 19680.618 | 209926.592 |
| 0.059 | 1.652000033 | 20019.939 | 213546.016 |
| 0.060 | 1.680000034 | 20359.260 | 217165.440 |
| 0.061 | 1.708000034 | 20696.581 | 220784.864 |
| 0.062 | 1.736000035 | 21037.902 | 224404.288 |
| 0.063 | 1.764000035 | 21377.223 | 228023.712 |
| 0.064 | 1.792000036 | 21716.544 | 231643.163 |
| 0.065 | 1.820000036 | 22066.866 | 235262.560 |
| 0.066 | 1.848000037 | 22395.186 | 238881.984 |
| 0.067 | 1.876000038 | 22734.507 | 242501.408 |
| 0.068 | 1.904000038 | 23073.828 | 246120.832 |
| 0.069 | 1.932000039 | 23413.149 | 249740.256 |
| 0.070 | 1.960000039 | 23752.470 | 253359.680 |
| 0.071 | 1.988000040 | 24091.791 | 256979.104 |
| 0.072 | 2.016000040 | 24431.112 | 260598.528 |
| 0.073 | 2.044000041 | 24770.433 | 264217.952 |
| 0.074 | 2.072000041 | 25109.754 | 267837.376 |

TABLE 3-continued

Table For Humans

| | | | |
|---|---|---|---|
| 0.075 | 2.100000042 | 25449.075 | 271456.800 |
| 0.076 | 2.128000043 | 25788.396 | 275076.224 |
| 0.077 | 2.156000043 | 26127.717 | 278695.648 |
| 0.078 | 2.184000044 | 26467.038 | 282315.072 |
| 0.079 | 2.212000044 | 26806.359 | 285934.496 |
| 0.080 | 2.240000045 | 27145.680 | 289553.920 |
| 0.081 | 2.268000045 | 27485.001 | 293173.344 |
| 0.082 | 2.296000046 | 27824.322 | 296792.768 |
| 0.083 | 2.324000046 | 28163.643 | 300412.192 |
| 0.084 | 2.352000047 | 28502.964 | 304031.616 |
| 0.085 | 2.380000028 | 28842.285 | 307651.040 |
| 0.086 | 2.408000048 | 29181.606 | 311270.464 |
| 0.087 | 2.436000048 | 29520.927 | 314889.888 |
| 0.088 | 2.464000049 | 29860.248 | 318509.312 |
| 0.089 | 2.492000050 | 30199.569 | 322128.736 |
| 0.090 | 2.520000050 | 30538.890 | 325748.160 |
| 0.091 | 2.548000051 | 30878.211 | 329367.584 |
| 0.092 | 2.576000052 | 31217.532 | 332987.008 |
| 0.093 | 2.604000052 | 31556.853 | 336606.432 |
| 0.094 | 2.632000053 | 31896.174 | 340225.856 |
| 0.095 | 2.660000053 | 32235.495 | 343845.280 |
| 0.096 | 2.688000054 | 32574.816 | 347464.704 |
| 0.097 | 2.716000054 | 32914.137 | 351084.128 |
| 0.098 | 2.744000055 | 33253.458 | 354703.552 |
| 0.099 | 2.722000055 | 33592.779 | 358322.976 |
| 0.100 | 2.800000056 | 33932.100 | 361942.400 |
| 0.101 | 2.828000057 | 34271.421 | 365561.824 |
| 0.102 | 2.856000057 | 34610.742 | 369181.248 |
| 0.103 | 2.884000058 | 34950.063 | 372800.672 |
| 0.104 | 2.912000058 | 35289.384 | 376420.096 |
| 0.105 | 2.940000059 | 35628.705 | 380039.520 |
| 0.106 | 2.968000059 | 35968.026 | 383658.944 |
| 0.107 | 2.996000060 | 36307.347 | 387278.368 |
| 0.108 | 3.024000060 | 38646.668 | 390897.792 |
| 0.109 | 3.052000061 | 36985.989 | 394517.216 |
| 0.110 | 3.080000062 | 37325.31 | 398136.640 |
| 0.111 | 3.108000062 | 37664.631 | 401756.064 |
| 0.112 | 3.136000063 | 38003.952 | 405375.488 |
| 0.113 | 3.164000083 | 38343.273 | 408994.912 |
| 0.114 | 3.192000064 | 38682.594 | 412614.336 |
| 0.115 | 3.220000064 | 39021.915 | 416233.760 |
| 0.116 | 3.248000065 | 39361.236 | 419853.184 |
| 0.117 | 3.276000066 | 39700.557 | 423472.608 |
| 0.118 | 3.304000066 | 40039.878 | 427092.032 |
| 0.119 | 3.332000067 | 40379.199 | 430711.456 |
| 0.120 | 3.360000067 | 40718.520 | 434330.880 |
| 0.121 | 3.388000068 | 41057.841 | 437950.304 |
| 0.122 | 3.416000068 | 41397.162 | 441589.728 |
| 0.123 | 3.444000069 | 41736.483 | 445189.152 |
| 0.124 | 3.472000069 | 42075.804 | 448808.576 |
| 0.125 | 3.500000070 | 42415.125 | 452428.000 |
| 0.126 | 3.528000071 | 42754.446 | 456047.424 |
| 0.127 | 3.556000071 | 43093.767 | 459666.848 |
| 0.128 | 3.584000072 | 43433.088 | 463286.272 |
| 0.129 | 3.612000072 | 43772.409 | 466905.696 |
| 0.130 | 3.640000073 | 44111.730 | 470525.100 |
| 0.131 | 3.668000073 | 44451.051 | 474144.544 |
| 0.132 | 3.696000074 | 44790.372 | 477763.968 |
| 0.133 | 3.724000074 | 45129.693 | 481383.392 |
| 0.134 | 3.752000076 | 45469.014 | 485002.816 |
| 0.135 | 3.780000076 | 45808.335 | 488622.240 |
| 0.136 | 3.808000076 | 46147.658 | 492241.664 |
| 0.137 | 3.936000077 | 46486.977 | 495861.088 |
| 0.138 | 3.864000077 | 46826.298 | 499480.512 |
| 0.139 | 3.892000078 | 47165.619 | 50309.936 |
| 0.140 | 3.920000078 | 47504.940 | 506719.360 |
| 0.141 | 3.948000079 | 47844.261 | 510338.784 |
| 0.142 | 3.976000080 | 48183.582 | 513958.208 |
| 0.143 | 4.004000080 | 48522.903 | 517577.632 |
| 0.144 | 4.032000081 | 48862.224 | 521197.056 |
| 0.145 | 4.060000810 | 49201.545 | 524816.480 |
| 0.146 | 4.088000082 | 49540.866 | 528435.904 |
| 0.147 | 4.116000082 | 49880.187 | 532055.328 |
| 0.148 | 4.144000083 | 50219.508 | 535674.752 |
| 0.149 | 4.172000083 | 50558.829 | 539294.176 |
| 0.150 | 4.200000084 | 50898.150 | 542913.600 |
| 0.151 | 4.228000085 | 51237.471 | 54633.024 |
| 0.152 | 4.258000085 | 51576.792 | 550152.448 |
| 0.153 | 4.284000086 | 51916.113 | 553771.872 |
| 0.154 | 4.312000086 | 52255.434 | 557391.296 |
| 0.155 | 4.340000087 | 52594.755 | 561010.720 |
| 0.156 | 4.368000087 | 52934.076 | 564630.144 |
| 0.157 | 4.396000088 | 53273.397 | 568249.568 |
| 0.158 | 4.424000088 | 53812.718 | 571868.992 |
| 0.159 | 4.452000089 | 53952.039 | 575488.416 |
| 0.160 | 4.480000090 | 54291.360 | 579107.840 |
| 0.161 | 4.508000090 | 54630.681 | 582727.264 |
| 0.162 | 4.536000091 | 54970.002 | 586346.688 |
| 0.163 | 4.564000091 | 55309.323 | 589966.112 |
| 0.164 | 4.592000092 | 55648.644 | 593585.536 |
| 0.165 | 4.620000092 | 55987.965 | 597204.960 |
| 0.166 | 4.648000093 | 56327.286 | 600824.384 |
| 0.167 | 4.676000094 | 56686.607 | 604443.808 |
| 0.168 | 4.704000094 | 57005.928 | 608063.232 |
| 0.169 | 4.732000095 | 57345.249 | 611682.858 |
| 0.170 | 4.760000095 | 57684.570 | 615302.080 |
| 0.171 | 4.788000096 | 58023.891 | 618921.504 |
| 0.172 | 4.816000096 | 58363.212 | 622540.928 |
| 0.173 | 4.844000097 | 58702.533 | 628160.352 |
| 0.174 | 4.872000097 | 59041.854 | 629779.776 |
| 0.175 | 4.900000098 | 59381.175 | 633399.2 |
| 0.176 | 4.928000099 | 59720.496 | 637018.624 |
| 0.177 | 4.856000099 | 60059.817 | 640838.048 |
| 0.178 | 4.984000100 | 60399.138 | 644257.472 |
| 0.179 | 5.012000100 | 60738.459 | 647876.896 |
| 0.180 | 5.040000101 | 61077.780 | 651496.320 |
| 0.181 | 5.068000101 | 61417.101 | 655115.744 |
| 0.182 | 5.096000102 | 61756.422 | 658735.168 |
| 0.183 | 5.124000102 | 62095.743 | 662354.592 |
| 0.184 | 5.152000103 | 62435.064 | 665974.016 |
| 0.185 | 5.180000104 | 52774.385 | 669593.440 |
| 0.186 | 5.208000104 | 63113.706 | 763212.864 |
| 0.187 | 5.236000105 | 63453.027 | 676832.288 |
| 0.188 | 5.264000105 | 63792.348 | 680451.712 |
| 0.189 | 5.292000106 | 64131.669 | 684071.136 |
| 0.190 | 5.320000106 | 64470.99 | 687690.560 |
| 0.191 | 5.348000107 | 64810.311 | 691309.984 |
| 0.192 | 5.376000108 | 65149.532 | 694929.408 |
| 0.193 | 5.404000108 | 65488.953 | 698548.832 |
| 0.194 | 5.432000109 | 65828.274 | 702168.256 |
| 0.195 | 5.460000109 | 66167.595 | 705787.68 |
| 0.196 | 5.488000110 | 66506.916 | 709407.104 |
| 0.197 | 5.516000110 | 66846.237 | 713026.528 |
| 0.198 | 5.544000111 | 67185.558 | 716645.952 |
| 0.199 | 5.572000111 | 67524.879 | 720265.376 |
| 0.200 | 5.600000112 | 67864.200 | 723884.800 |
| 0.201 | 5.628000113 | 68203.521 | 727504.224 |
| 0.202 | 5.656000113 | 68542.842 | 731123.648 |
| 0.203 | 5.684000114 | 68882.163 | 744743.072 |
| 0.204 | 5.712000114 | 69221.484 | 7.8362.496 |
| 0.205 | 5.740000115 | 69560.805 | 741981.920 |
| 0.206 | 5.768000115 | 69900.126 | 745801.344 |
| 0.207 | 5.796000116 | 70239.447 | 749220.768 |
| 0.208 | 5.824000116 | 70578.768 | 752840.192 |
| 0.209 | 5.852000117 | 70918.089 | 756459.616 |
| 0.210 | 5.880000118 | 71257.410 | 760079.040 |
| 0.211 | 5.908000118 | 71596.731 | 763698.464 |
| 0.212 | 5.936000119 | 71936.052 | 767317.888 |
| 0.213 | 5.964000119 | 72275.373 | 770937.312 |
| 0.214 | 5.992000120 | 72614.694 | 774556.738 |
| 0.215 | 6.020000120 | 72954.015 | 778178.160 |
| 0.216 | 6.048000121 | 73293.336 | 781795.584 |
| 0.217 | 6.076000122 | 73832.657 | 785415.008 |
| 0.218 | 6.104000122 | 73971.978 | 789034.432 |
| 0.219 | 6.132000123 | 74311.299 | 492653.856 |
| 0.220 | 6.160000123 | 74650.620 | 796372.280 |
| 0.221 | 6.188000124 | 74989.941 | 799892.704 |
| 0.222 | 6.216000124 | 75329.262 | 803512.128 |
| 0.223 | 6.244000125 | 75888.583 | 807161.552 |
| 0.224 | 6.272000125 | 76007.904 | 810750.976 |
| 0.225 | 6.300000126 | 76347.225 | 814370.400 |
| 0.226 | 6.328000127 | 76686.646 | 817989.824 |
| 0.227 | 6.356000127 | 77025.867 | 821609.248 |
| 0.228 | 6.384000128 | 77365.188 | 825228.672 |

TABLE 3-continued

Table For Humans

| | | | |
|---|---|---|---|
| 0.229 | 6.412000128 | 77704.509 | 828848.096 |
| 0.230 | 6.440000129 | 78043.830 | 832467.520 |
| 0.231 | 6.468000129 | 78383.151 | 836086.944 |
| 0.232 | 6.496000130 | 78722.472 | 839706.368 |
| 0.233 | 6.524000130 | 79061.973 | 843325.792 |
| 0.234 | 6.552000131 | 79401.114 | 846945.206 |
| 0.235 | 6.580000132 | 79740.435 | 850564.640 |
| 0.236 | 6.608000132 | 80079.756 | 864184.064 |
| 0.237 | 6.636000133 | 80419.077 | 857803.488 |
| 0.238 | 6.684000133 | 80758.398 | 831422.912 |
| 0.239 | 6.692000134 | 81097.719 | 865042.336 |
| 0.240 | 6.720000134 | 81437.040 | 868661.760 |
| 0.241 | 6.748000135 | 81776.361 | 872281.184 |
| 0.242 | 6.776000136 | 82115.882 | 875900.608 |
| 0.243 | 6.804000136 | 82455.003 | 879520.032 |
| 0.244 | 6.832000137 | 82791.324 | 883139.456 |
| 0.245 | 6.860000137 | 93133.645 | 886759.880 |
| 0.246 | 6.888000138 | 83472.966 | 890378.304 |
| 0.247 | 6.916000138 | 83812.287 | 893997.728 |
| 0.248 | 6.944000139 | 84151.608 | 897617.152 |
| 0.249 | 6.972000139 | 84490.929 | 901236.576 |
| 0.250 | 7.000000140 | 84830.250 | 904856 |
| 0.251 | 7.028000141 | 95169.571 | 908475.424 |
| 0.252 | 7.055000141 | 85508.892 | 912094.848 |
| 0.253 | 7.084000142 | 85848.213 | 915714.272 |
| 0.254 | 7.112000142 | 86187.534 | 919333.696 |
| 0.255 | 7.140000143 | 86526.855 | 922953.120 |
| 0.256 | 7.168000143 | 86866.176 | 926572.544 |
| 0.257 | 7.196000144 | 87205.497 | 930191.968 |
| 0.258 | 7.224000144 | 87544.818 | 933811.392 |
| 0.259 | 7.252000145 | 87884.139 | 937430.816 |
| 0.260 | 7.280000146 | 88223.460 | 941050.240 |
| 0.261 | 7.308000146 | 88562.791 | 944668.664 |
| 0.262 | 7.336000147 | 88902.102 | 948289.088 |
| 0.263 | 7.364000147 | 89241.423 | 951908.512 |
| 0.264 | 7.392000148 | 89580.744 | 955527.936 |
| 0.265 | 7.420000148 | 89920.065 | 959147.360 |
| 0.266 | 7.448000149 | 90259.386 | 952766.784 |
| 0.267 | 7.476000150 | 90598.707 | 966386.208 |
| 0.268 | 7.504000150 | 90938.028 | 970005.632 |
| 0.269 | 7.532000151 | 91277.349 | 97362.056 |
| 0.270 | 7.560000151 | 91616.670 | 977244.480 |
| 0.271 | 7.588000152 | 91955.991 | 980863.904 |
| 0.272 | 7.616000152 | 92295.312 | 984483.328 |
| 0.273 | 7.644000153 | 92634.633 | 988102.752 |
| 0.274 | 7.672000153 | 92973.954 | 991722.176 |
| 0.275 | 7.700000154 | 93313.275 | 995341.600 |
| 0.276 | 7.728000155 | 93652.596 | 998961.024 |
| 0.277 | 7.756000155 | 93991.917 | 1002580.448 |
| 0.278 | 7.784000156 | 94331.238 | 1006199.872 |
| 0.279 | 7.812000156 | 94670.559 | 1009819.296 |
| 0.280 | 7.840000157 | 95009.880 | 1013438.720 |
| 0.281 | 7.868000157 | 95349.201 | 1017058.144 |
| 0.282 | 7.896000158 | 95688.522 | 1020677.568 |
| 0.283 | 7.924000158 | 96027.643 | 1024296.992 |
| 0.284 | 7.952000159 | 96367.164 | 1027916.416 |
| 0.285 | 7.980000160 | 96706.485 | 1031535.840 |
| 0.286 | 8.008000160 | 97045.806 | 1035155.264 |
| 0.287 | 8.036000161 | 97385.127 | 1038774.688 |
| 0.288 | 8.064000161 | 97724.448 | 1042394.112 |
| 0.289 | 8.092000162 | 98063.769 | 1046013.536 |
| 0.290 | 8.120000162 | 98403.090 | 1049632.960 |
| 0.291 | 8.148000163 | 98742.411 | 1053252.384 |
| 0.292 | 8.176000164 | 99081.732 | 1056871.808 |
| 0.293 | 8.204000164 | 99421.053 | 1060491.232 |
| 0.294 | 8.232000165 | 99760.374 | 1064110.656 |
| 0.295 | 8.260000165 | 100099.695 | 1067730.080 |
| 0.296 | 8.288000168 | 100439.016 | 1071349.504 |
| 0.297 | 8.316000166 | 100778.337 | 1072968.928 |
| 0.298 | 8.344000167 | 101117.658 | 1078588.352 |
| 0.299 | 8.372000167 | 101456.979 | 1082207.776 |
| 0.300 | 8.400000168 | 101796.300 | 1085827.200 |
| 0.301 | 8.428000169 | 102135.621 | 1089446.624 |
| 0.302 | 8.456000169 | 102474.942 | 1093066.048 |
| 0.303 | 8.484000170 | 102814.263 | 1096685.472 |
| 0.304 | 8.512000170 | 103153.584 | 1100304.896 |
| 0.305 | 8.640000171 | 103492.905 | 1103924.320 |
| 0.306 | 8.568000171 | 103832.226 | 1107543.744 |
| 0.307 | 8.596000172 | 104171.547 | 1111163.168 |
| 0.308 | 8.624000192 | 104510.868 | 1114782.592 |
| 0.309 | 8.652000173 | 104850.189 | 1118402.016 |
| 0.310 | 8.680000174 | 105189.510 | 1122021.440 |
| 0.311 | 8.708000174 | 105528.831 | 1125640.864 |
| 0.312 | 8.836000175 | 105868.152 | 1129260.288 |
| 0.313 | 8.764000175 | 106207.473 | 1132879.712 |
| 0.314 | 8.792000176 | 106546.794 | 1136499.136 |
| 0.315 | 8.820000176 | 106886.115 | 1140118.560 |
| 0.316 | 8.848000177 | 107225.436 | 1143737.984 |
| 0.317 | 8.876000178 | 107564.757 | 1147357.408 |
| 0.318 | 8.904000178 | 107904.078 | 1150976.832 |
| 0.319 | 8.932000179 | 108243.399 | 1154596.256 |
| 0.320 | 8.960000179 | 108582.720 | 1158215.680 |
| 0.321 | 8.988000180 | 108922.041 | 1161835.104 |
| 0.322 | 9.016000180 | 109261.362 | 1165454.528 |
| 0.323 | 9.044000181 | 109600.683 | 1169073.952 |
| 0.324 | 9.072000181 | 109940.004 | 1172693.376 |
| 0.325 | 9.100000182 | 110279.325 | 1176312.800 |
| 0.326 | 9.128000183 | 110618.646 | 1179932.224 |
| 0.327 | 9.156000183 | 110957.967 | 1183551.648 |
| 0.328 | 9.184000184 | 111297.288 | 1187171.072 |
| 0.329 | 9.212000184 | 111636.609 | 1190790.496 |
| 0.330 | 9.240000185 | 111975.930 | 1194409.920 |
| 0.331 | 9.268000185 | 112315.251 | 1198029.344 |
| 0.332 | 9.296000186 | 112654.572 | 1201648.768 |
| 0.333 | 9.324000186 | 112993.893 | 1205268.192 |
| 0.334 | 9.352000187 | 113333.214 | 1208887.616 |
| 0.335 | 9.380000188 | 113672.535 | 1212507.040 |
| 0.336 | 9.408000188 | 114011.856 | 1216126.464 |
| 0.337 | 9.436000189 | 114351.177 | 1219745.888 |
| 0.338 | 9.464000189 | 114890.498 | 1223365.312 |
| 0.339 | 9.492000190 | 115029.819 | 1226984.736 |
| 0.340 | 9.520000190 | 115369.140 | 1230604.160 |
| 0.341 | 9.548000191 | 115705.461 | 1234223.584 |
| 0.342 | 8.576000192 | 116047.782 | 1237843.008 |
| 0.343 | 9.604000192 | 116387.103 | 1241462.432 |
| 0.344 | 9.632000193 | 116726.424 | 1245081.856 |
| 0.345 | 9.680000193 | 117065.745 | 1248701.280 |
| 0.346 | 9.688000194 | 117405.086 | 1252320.704 |
| 0.347 | 9.716000194 | 117744.387 | 1255940.128 |
| 0.348 | 9.744000195 | 118083.708 | 1259559.552 |
| 0.349 | 9.772000195 | 118423.029 | 1263178.976 |
| 0.350 | 9.800000196 | 118762.350 | 1266798.4 |
| 0.351 | 9.828000197 | 119101.671 | 1270417.824 |
| 0.352 | 9.858000197 | 119440.992 | 1274037.248 |
| 0.353 | 9.884000198 | 119780.313 | 1277656.672 |
| 0.354 | 9.912000198 | 120119.634 | 1281276.096 |
| 0.355 | 9.940000199 | 120458.955 | 1284895.520 |
| 0.356 | 9.968000199 | 120798.276 | 1288514.944 |
| 0.357 | 9.996000200 | 121137.597 | 1292134.368 |
| 0.358 | 10.024000200 | 121476.918 | 1295759.792 |
| 0.359 | 10.052000200 | 121816.239 | 1299373.216 |
| 0.360 | 10.080000200 | 122155.560 | 1302992.640 |
| 0.361 | 10.108000200 | 122494.881 | 1306612.064 |
| 0.362 | 10.138000200 | 122834.202 | 1310231.488 |
| 0.363 | 10.164000200 | 123173.523 | 1313850.912 |
| 0.364 | 10.192000200 | 123512.844 | 1317470.336 |
| 0.365 | 10.220000200 | 123852.165 | 1321089.760 |
| 0.366 | 10.248000200 | 124191.486 | 1324709.184 |
| 0.367 | 10.276000210 | 124530.807 | 1328328.608 |
| 0.368 | 10.304000210 | 124870.128 | 1331948.032 |
| 0.369 | 10.332000210 | 125209.449 | 1335567.456 |
| 0.370 | 10.360000210 | 125548.770 | 1339186.880 |
| 0.371 | 10.388000210 | 125888.091 | 1342806.304 |
| 0.372 | 10.416000210 | 126227.412 | 1346425.728 |
| 0.373 | 10.444000210 | 126566.733 | 1650045.152 |
| 0.374 | 10.472000210 | 126906.054 | 1353664.576 |
| 0.375 | 10.500000210 | 127245.375 | 1357284.000 |
| 0.376 | 10.528000210 | 127584.696 | 1360903.424 |
| 0.377 | 10.558000210 | 127924.017 | 1364522.848 |
| 0.378 | 10.584000210 | 128263.338 | 1368142.272 |
| 0.379 | 10.612000210 | 128602.659 | 1371761.696 |
| 0.380 | 10.640000210 | 128941.980 | 1375381.120 |
| 0.381 | 10.66800021 | 129281.301 | 1379000.544 |
| 0.382 | 10.969000210 | 129620.622 | 1382619.968 |

TABLE 3-continued

Table For Humans

| | | | |
|---|---|---|---|
| 0.383 | 10.724000210 | 129959.943 | 1386239.392 |
| 0.384 | 10.752000220 | 130299.264 | 1389858.815 |
| 0.385 | 10.780000220 | 130638.585 | 1393478.240 |
| 0.386 | 10.808000220 | 130977.906 | 1397097.664 |
| 0.387 | 10.838000220 | 131317.227 | 1400717.088 |
| 0.388 | 10.864000220 | 131656.548 | 1404336.512 |
| 0.389 | 10.892000220 | 131995.869 | 1407955.936 |
| 0.390 | 10.920000220 | 132335.190 | 1411575.360 |
| 0.391 | 10.948000220 | 132674.511 | 1415194.784 |
| 0.392 | 10.976000220 | 133013.832 | 1418814.208 |
| 0.393 | 11.004000220 | 133353.153 | 1422433.632 |
| 0.394 | 11.032000220 | 133682.474 | 1426053.058 |
| 0.395 | 11.060000220 | 134031.795 | 1429672.480 |
| 0.396 | 11.088000220 | 134371.116 | 1433291.904 |
| 0.397 | 11.116000220 | 134710.437 | 1436911.328 |
| 0.398 | 11.144000220 | 135049.758 | 1440530.762 |
| 0.399 | 11.172000220 | 135389.079 | 1444150.176 |
| 0.400 | 11.200000220 | 135728.400 | 1447769.600 |
| 0.401 | 11.228000220 | 136067.721 | 1451389.024 |
| 0.402 | 11.256000230 | 136407.042 | 1455008.448 |
| 0.403 | 11.274000230 | 136746.363 | 1458627.872 |
| 0.404 | 11.312000230 | 137085.684 | 1462247.296 |
| 0.405 | 11.340002300 | 137425.005 | 1465886.720 |
| 0.406 | 11.368000230 | 137764.326 | 1469486.144 |
| 0.407 | 11.396000230 | 138103.647 | 1473105.568 |
| 0.408 | 11.424000230 | 138442.968 | 1476724.992 |
| 0.409 | 11.452000230 | 138782.289 | 1480344.416 |
| 0.410 | 11.480000230 | 139121.610 | 1483963.840 |
| 0.411 | 11.508000230 | 139460.931 | 1487583.264 |
| 0.412 | 11.536000230 | 139800.252 | 1491202.688 |
| 0.413 | 11.564000230 | 140139.573 | 1494822.112 |
| 0.414 | 11.692000230 | 140478.894 | 1498441.536 |
| 0.415 | 11.620000230 | 170818.215 | 1502060.960 |
| 0.416 | 11.648000230 | 141157.536 | 1505680.384 |
| 0.417 | 11.676000230 | 141496.857 | 1509299.808 |
| 0.418 | 11.704000230 | 141836.178 | 1512919.232 |
| 0.419 | 11.732000230 | 142175.499 | 1518538.656 |
| 0.420 | 11.760000240 | 142514.820 | 1520158.080 |
| 0.421 | 11.788000240 | 142854.141 | 1523777.504 |
| 0.422 | 11.816000240 | 143193.462 | 1527396.928 |
| 0.423 | 11.844000240 | 143532.783 | 1531016.352 |
| 0.424 | 11.872000240 | 143872.104 | 1534635.776 |
| 0.425 | 11.900000240 | 144211.425 | 1538255.200 |
| 0.426 | 11.928000240 | 144550.746 | 1541874.624 |
| 0.427 | 11.956000240 | 144890.067 | 1545494.048 |
| 0.428 | 11.984000240 | 145229.388 | 1549113.482 |
| 0.429 | 12.012000240 | 145568.709 | 1552732.896 |
| 0.430 | 12.040000240 | 145906.030 | 1556352.320 |
| 0.431 | 12.068000240 | 146247.351 | 1559971.744 |
| 0.432 | 12.096000240 | 146586.672 | 1563691.168 |
| 0.433 | 12.124000240 | 146925.993 | 1567210.592 |
| 0.434 | 12.152000240 | 147265.314 | 1570830.018 |
| 0.435 | 12.180000240 | 147604.635 | 1574449.440 |
| 0.436 | 12.208000240 | 147943.956 | 1578068.864 |
| 0.437 | 12.236000240 | 148283.277 | 1581688.288 |
| 0.438 | 12.264000250 | 148622.598 | 1585307.712 |
| 0.439 | 12.282000250 | 148961.919 | 1588927.136 |
| 0.440 | 12.320000250 | 149301.240 | 1592546.560 |
| 0.441 | 12.348000250 | 149640.561 | 1596165.984 |
| 0.442 | 12.386000250 | 149979.882 | 1599785.408 |
| 0.443 | 12.404000250 | 150319.203 | 1603404.832 |
| 0.444 | 12.432000250 | 150658.524 | 1607024.256 |
| 0.445 | 12.460000250 | 150997.845 | 1610643.680 |
| 0.446 | 12.488000250 | 151337.166 | 1614263.104 |
| 0.447 | 12.516000250 | 151676.487 | 1617882.528 |
| 0.448 | 12.544000250 | 152015.808 | 1621501.952 |
| 0.449 | 12.572000250 | 152355.129 | 1625121.376 |
| 0.450 | 12.600000250 | 152694.450 | 1628740.800 |
| 0.451 | 12.628000250 | 1533033.771 | 1632360.224 |
| 0.452 | 12.656000250 | 153373.092 | 1635979.646 |
| 0.453 | 12.684000250 | 153712.413 | 1639599.072 |
| 0.454 | 12.712000250 | 154051.734 | 1643218.496 |
| 0.455 | 12.740000250 | 154391.055 | 1646837.920 |
| 0.456 | 12.768000260 | 154730.376 | 1650457.344 |
| 0.457 | 12.796000260 | 155069.697 | 1654076.768 |
| 0.458 | 12.824000260 | 155409.018 | 1657696.792 |
| 0.459 | 12.852000260 | 155748.339 | 1661315.616 |
| 0.460 | 12.880000260 | 156087.660 | 1664935.040 |
| 0.461 | 12.908000260 | 156426.981 | 1668554.464 |
| 0.462 | 12.936000260 | 156766.302 | 1672173.888 |
| 0.463 | 12.964000260 | 157105.523 | 1675793.312 |
| 0.464 | 12.992000260 | 157444.944 | 1679412.736 |
| 0.465 | 13.020000260 | 157784.265 | 1383032.160 |
| 0.466 | 13.048000260 | 158123.586 | 1686651.584 |
| 0.467 | 13.076000260 | 128462.907 | 1690271.008 |
| 0.468 | 13.104000260 | 158802.228 | 1693890.432 |
| 0.469 | 13.132000260 | 159141.549 | 1697509.856 |
| 0.470 | 13.160000260 | 159480.870 | 1701129.280 |
| 0.471 | 13.188000260 | 159820.191 | 1704748.704 |
| 0.472 | 13.216000260 | 160159.512 | 1708368.128 |
| 0.473 | 13.244000260 | 160498.833 | 1711987.552 |
| 0.474 | 13.272000270 | 160838.154 | 1715606.976 |
| 0.475 | 13.300000270 | 161177.475 | 1719226.400 |
| 0.476 | 13.328000270 | 161516.795 | 1722845.824 |
| 0.477 | 13.356000270 | 161856.117 | 1726465.248 |
| 0.478 | 13.384000270 | 162195.438 | 1730084.672 |
| 0.479 | 13.412000270 | 162534.759 | 1733704.096 |
| 0.480 | 13.440000270 | 162874.080 | 1737323.520 |
| 0.481 | 13.468000270 | 163213.401 | 1740942.944 |
| 0.482 | 13.496000270 | 163552.722 | 1744562.368 |
| 0.483 | 13.524000270 | 163892.043 | 1748181.792 |
| 0.484 | 13.552000270 | 164231.364 | 1751801.216 |
| 0.485 | 13.580000270 | 164570.685 | 1755420.640 |
| 0.486 | 13.608000270 | 164910.006 | 1759040.064 |
| 0.487 | 13.636000270 | 165249.327 | 1762659.488 |
| 0.488 | 13.664000270 | 165588.648 | 1766276.810 |
| 0.489 | 13.692000270 | 165927.969 | 1769898.336 |
| 0.490 | 13.720000270 | 166287.29 | 1773517.76 |
| 0.491 | 13.748000270 | 166606.611 | 1777137.184 |
| 0.492 | 13.778000280 | 166945.932 | 1780756.608 |
| 0.493 | 13.804000280 | 167285.253 | 1784376.032 |
| 0.494 | 13.832000280 | 167624.574 | 1787995.456 |
| 0.495 | 13.860000280 | 167963.895 | 1791614.880 |
| 0.496 | 13.888000280 | 168303.216 | 1795234.304 |
| 0.497 | 13.916000280 | 168642.537 | 1798853.728 |
| 0.498 | 13.944000280 | 168981.858 | 1802473.152 |
| 0.499 | 13.972000280 | 169321.179 | 1806092.567 |
| 0.500 | 14.000000280 | 169660.500 | 1809712.000 |
| 0.501 | 14.028000280 | 169999.821 | 1813331.424 |
| 0.502 | 14.056000280 | 170339.142 | 1816950.848 |
| 0.503 | 14.084000280 | 170678.463 | 1820570.272 |
| 0.504 | 14.112000280 | 171017.784 | 1824189.696 |
| 0.505 | 14.140000280 | 171367.105 | 1827809.120 |
| 0.506 | 14.168000280 | 171696.426 | 1831428.544 |
| 0.507 | 14.196000280 | 172035.747 | 1835047.968 |
| 0.508 | 14.224000280 | 172375.068 | 1838667.392 |
| 0.509 | 14.252000290 | 172714.389 | 1842286.816 |
| 0.510 | 14.280000290 | 173053.710 | 1845906.240 |
| 0.511 | 14.308000290 | 173393.031 | 1849525.664 |
| 0.512 | 14.336000290 | 173732.352 | 1853145.088 |
| 0.513 | 14.364000290 | 174071.673 | 1856764.512 |
| 0.514 | 14.392000290 | 174410.994 | 1860383.936 |
| 0.515 | 14.420000290 | 174750.315 | 1864003.360 |
| 0.516 | 14.448000290 | 175089.636 | 1867622.784 |
| 0.517 | 14.476000290 | 175428.957 | 1871242.208 |
| 0.518 | 14.504000290 | 175768.278 | 1874861.632 |
| 0.519 | 14.532000290 | 176107.599 | 1878481.058 |
| 0.520 | 14.560000290 | 176446.920 | 1882100.480 |
| 0.521 | 14.588000290 | 176786.241 | 1885719.904 |
| 0.522 | 14.616000290 | 177125.562 | 1889339.328 |
| 0.523 | 14.644000290 | 177464.883 | 1892958.752 |
| 0.524 | 14.672000290 | 177804.204 | 1896578.176 |
| 0.525 | 14.700000290 | 178143.525 | 1900197.600 |
| 0.526 | 14.728000290 | 178482.846 | 1903817.024 |
| 0.527 | 14.756000300 | 178822.167 | 1907436.448 |
| 0.528 | 14.784000300 | 179161.488 | 1911055.872 |
| 0.529 | 14.812000300 | 179500.809 | 1914675.296 |
| 0.530 | 14.840000300 | 179840.130 | 1918294.720 |
| 0.531 | 14.868000300 | 180179.451 | 1921914.144 |
| 0.532 | 14.896000300 | 180518.772 | 1925533.568 |
| 0.533 | 14.924000300 | 180858.093 | 1929152.992 |
| 0.534 | 14.952000300 | 181197.414 | 1932772.416 |
| 0.535 | 14.980000300 | 181536.735 | 1936391.840 |
| 0.536 | 15.005000300 | 181876.056 | 1940011.264 |

TABLE 3-continued

Table For Humans

| | | | |
|---|---|---|---|
| 0.537 | 15.036000300 | 182215.377 | 1943630.688 |
| 0.538 | 15.064000300 | 182554.698 | 1947250.112 |
| 0.539 | 15.092000300 | 182894.019 | 1950869.536 |
| 0.540 | 15.120000300 | 183233.340 | 1954488.96 |
| 0.541 | 15.148000300 | 183572.661 | 1958108.384 |
| 0.542 | 15.176000300 | 183911.982 | 1961727.808 |
| 0.543 | 15.204000300 | 184251.303 | 1965347.232 |
| 0.544 | 15.232000300 | 184590.624 | 1968966.656 |
| 0.545 | 15.260000300 | 184929.945 | 1972586.08 |
| 0.546 | 15.288000310 | 185269.266 | 1976205.504 |
| 0.547 | 15.316000310 | 185608.587 | 1979824.928 |
| 0.548 | 15.344000310 | 185947.908 | 1983444.352 |
| 0.549 | 15.372000310 | 186287.229 | 1987063.776 |
| 0.550 | 15.400000310 | 186626.550 | 1990683.200 |
| 0.551 | 15.428000310 | 186965.871 | 1994302.624 |
| 0.552 | 15.456000310 | 187305.192 | 1997922.048 |
| 0.553 | 15.484000310 | 187644.513 | 2001541.472 |
| 0.554 | 15.512000310 | 187983.834 | 2005160.896 |
| 0.555 | 15.540000310 | 188323.155 | 2008780.320 |
| 0.556 | 15.568000310 | 188662.476 | 2012399.744 |
| 0.557 | 15.596000310 | 189001.797 | 2016019.168 |
| 0.558 | 15.624000310 | 189341.118 | 2019638.592 |
| 0.559 | 15.652000310 | 189??0.439 | 2023258.016 |
| 0.560 | 15.680000310 | 190019.760 | 2026877.440 |
| 0.561 | 15.708000310 | 190359.081 | 2030496.864 |
| 0.562 | 15.736000310 | 190698.402 | 2034116.288 |
| 0.563 | 15.764000320 | 191037.723 | 2037735.712 |
| 0.564 | 15.792000320 | 191377.044 | 2041355.136 |
| 0.565 | 15.820000320 | 191716.385 | 2044974.560 |
| 0.566 | 15.848000320 | 192055.686 | 2048593.984 |
| 0.567 | 15.876000320 | 192395.007 | 2052213.408 |
| 0.568 | 15.904000320 | 192734.328 | 2055832.832 |
| 0.569 | 15.932000320 | 193073.649 | 2059452.256 |
| 0.570 | 15.960000320 | 193412.970 | 2063071.8 |
| 0.571 | 15.988000320 | 193752.291 | 2066691.104 |
| 0.572 | 16.016000320 | 194091.612 | 2070310.528 |
| 0.573 | 16.044000320 | 194430.933 | 2073929.952 |
| 0.574 | 16.072000320 | 194770.254 | 2077549.376 |
| 0.575 | 16.100000320 | 195109.575 | 2081168.8 |
| 0.576 | 16.128000320 | 195448.896 | 2084788.224 |
| 0.577 | 16.156000320 | 195788.217 | 2088407.648 |
| 0.578 | 16.184000320 | 196127.538 | 2092027.072 |
| 0.579 | 16.212000320 | 196466.859 | 2095646.496 |
| 0.580 | 16.240000320 | 196806.180 | 2099265.920 |
| 0.581 | 16.268000330 | 197145.501 | 2102885.344 |
| 0.582 | 16.296000330 | 197484.822 | 2106504.768 |
| 0.583 | 16.324000330 | 197824.143 | 2110124.192 |
| 0.584 | 16.352000330 | 198163.434 | 2113743.616 |
| 0.585 | 16.380000330 | 198502.785 | 2117363.040 |
| 0.586 | 16.408000330 | 198842.106 | 2120982.464 |
| 0.587 | 16.436000330 | 199181.427 | 2124601.888 |
| 0.588 | 16.464000330 | 199520.748 | 2128221.312 |
| 0.589 | 16.492000330 | 199860.069 | 2131840.736 |
| 0.590 | 16.520000330 | 200199.390 | 2135460.160 |
| 0.591 | 16.548000330 | 200538.711 | 2139079.581 |
| 0.592 | 16.576000330 | 200878.032 | 2142699.008 |
| 0.593 | 16.604000330 | 201217.353 | 2146318.432 |
| 0.594 | 16.632000330 | 201556.674 | 2149937.856 |
| 0.595 | 16.660000330 | 201895.995 | 2153557.280 |
| 0.596 | 16.688000330 | 202235.316 | 2157176.704 |
| 0.597 | 16.716000330 | 202574.634 | 2160796.128 |
| 0.598 | 16.744000330 | 202913.958 | 2164415.552 |
| 0.599 | 16.772000340 | 203253.279 | 2168034.976 |
| 0.600 | 16.800000340 | 203592.600 | 2171654.4 |
| 0.601 | 16.828000340 | 203931.921 | 2175273.824 |
| 0.602 | 16.856000340 | 204271.242 | 2178893.248 |
| 0.603 | 16.884000340 | 204610.563 | 2182512.672 |
| 0.604 | 16.912000340 | 204949.884 | 2188132.096 |
| 0.605 | 16.940000340 | 205289.205 | 2189751.520 |
| 0.606 | 16.968000340 | 205628.526 | 2193370.944 |
| 0.607 | 16.996000340 | 205966.847 | 2196990.368 |
| 0.608 | 17.024000340 | 206307.168 | 2200609.792 |
| 0.609 | 17.052000340 | 206646.489 | 2204229.216 |
| 0.610 | 17.080000340 | 206985.810 | 2207848.640 |
| 0.611 | 17.108000340 | 207325.131 | 2211468.064 |
| 0.612 | 17.136000340 | 207664.452 | 2215087.488 |
| 0.613 | 17.164000340 | 208003.773 | 2218706.912 |
| 0.614 | 17.192000340 | 208343.094 | 2222326.336 |
| 0.615 | 17.220000340 | 208682.415 | 2225945.760 |
| 0.616 | 17.248000340 | 209021.736 | 2229565.184 |
| 0.617 | 17.276000350 | 209361.057 | 2233184.608 |
| 0.618 | 17.304000350 | 209700.378 | 2236804.032 |
| 0.619 | 17.332000350 | 210039.699 | 2240423.456 |
| 0.620 | 17.360000350 | 210379.020 | 2244042.880 |
| 0.621 | 17.388000350 | 210718.341 | 2247662.304 |
| 0.622 | 17.41600035 | 211057.662 | 2251281.728 |
| 0.623 | 17.444000350 | 211396.983 | 2254901.152 |
| 0.624 | 17.472000350 | 211736.304 | 2258520.576 |
| 0.625 | 17.500000350 | 212075.625 | 2262140.000 |
| 0.626 | 17.528000350 | 212414.946 | 2265759.424 |
| 0.627 | 17.550003500 | 212754.267 | 2269378.848 |
| 0.628 | 17.584000350 | 213093.588 | 2272998.272 |
| 0.629 | 17.612000350 | 213432.909 | 2276617.696 |
| 0.630 | 17.640000350 | 213772.230 | 2280237.120 |
| 0.631 | 17.66800035 | 214111.551 | 2283856.544 |
| 0.632 | 17.696000350 | 214450.872 | 2287475.968 |
| 0.633 | 17.724000350 | 214790.193 | 2291095.392 |
| 0.634 | 17.752000350 | 215139.514 | 2294714.816 |
| 0.635 | 17.780000360 | 215468.835 | 2298334.240 |
| 0.636 | 17.808000360 | 215808.156 | 2301953.664 |
| 0.637 | 17.836000360 | 216147.477 | 2305573.088 |
| 0.638 | 17.864000360 | 216486.798 | 2309192.512 |
| 0.639 | 17.892000360 | 216826.119 | 231281.936 |
| 0.640 | 17.920000360 | 217165.440 | 2316431.360 |
| 0.641 | 17.940003600 | 215704.761 | 2320050.784 |
| 0.642 | 17.976000360 | 217844.082 | 2323670.208 |
| 0.643 | 18.004000360 | 218183.403 | 2327289.632 |
| 0.644 | 18.032000360 | 218522.724 | 2330909.056 |
| 0.645 | 18.060000360 | 218862.045 | 2334528.460 |
| 0.646 | 18.088000360 | 219201.366 | 2338147.904 |
| 0.647 | 18.116000360 | 219540.687 | 2341767.328 |
| 0.648 | 18.144000360 | 219880.008 | 2345386.752 |
| 0.649 | 18.172000360 | 220219.329 | 2349006.176 |
| 0.650 | 18.200000360 | 220558.650 | 2352825.600 |
| 0.651 | 18.228000360 | 220897.971 | 2356245.024 |
| 0.652 | 18.256000370 | 221237.292 | 2359867.448 |
| 0.653 | 18.284000370 | 221576.613 | 2363483.872 |
| 0.654 | 18.312000370 | 221915.934 | 2367103.296 |
| 0.655 | 18.340000370 | 222255.255 | 2370722.720 |
| 0.656 | 18.368000370 | 222594.576 | 2374342.144 |
| 0.657 | 18.396000370 | 222933.897 | 2377961.588 |
| 0.658 | 18.424000370 | 223273.218 | 2381580.992 |
| 0.659 | 18.452000370 | 223612.539 | 2385200.416 |
| 0.660 | 18.480000370 | 223951.860 | 2388819.840 |
| 0.661 | 18.508000370 | 224291.181 | 2392439.264 |
| 0.662 | 18.536000370 | 224630.502 | 2396058.888 |
| 0.663 | 18.564000370 | 224969.823 | 2399678.112 |
| 0.664 | 18.592000370 | 225309.144 | 2403297.536 |
| 0.665 | 18.620000370 | 225648.465 | 2406916.960 |
| 0.666 | 18.648000370 | 225987.786 | 2410538.384 |
| 0.667 | 18.676000370 | 226327.107 | 2414155.808 |
| 0.668 | 18.704000370 | 226666.428 | 2417775.232 |
| 0.669 | 18.732000370 | 227005.749 | 2421394.858 |
| 0.670 | 18.760000380 | 227345.070 | 2425014.080 |
| 0.671 | 18.788000380 | 227684.391 | 2428633.504 |
| 0.672 | 18.816000380 | 228023.712 | 2432252.928 |
| 0.673 | 18.844000380 | 228363.033 | 2435872.352 |
| 0.674 | 18.87200038 | 228702.354 | 2439491.776 |
| 0.675 | 18.900000380 | 229041.675 | 2443111.200 |
| 0.676 | 18.928000380 | 229380.996 | 2446730.624 |
| 0.677 | 18.958000380 | 229720.317 | 2460350.048 |
| 0.678 | 18.984000380 | 230059.638 | 2453969.472 |
| 0.679 | 19.012000380 | 230398.959 | 2457588.896 |
| 0.680 | 19.040000380 | 230738.280 | 2461208.320 |
| 0.681 | 19.068000380 | 321077.601 | 2464827.744 |
| 0.682 | 19.096000380 | 231416.922 | 2468447.168 |
| 0.683 | 19.124000380 | 231756.243 | 2472066.592 |
| 0.684 | 19.152000380 | 232095.564 | 2475686.016 |
| 0.685 | 19.180000380 | 232434.885 | 2479305.110 |
| 0.686 | 19.208000380 | 232774.206 | 2482924.864 |
| 0.687 | 19.236000380 | 233113.527 | 2486544.288 |
| 0.688 | 19.264000390 | 233452.848 | 2490163.712 |
| 0.689 | 19.292000390 | 233792.169 | 2493783.136 |
| 0.690 | 19.320000390 | 234131.490 | 2497402.560 |

TABLE 3-continued

Table For Humans

| | | | | | | | |
|---|---|---|---|---|---|---|---|
| 0.691 | 19.348000390 | 234470.811 | 2501021.984 | 0.768 | 21.504000430 | 260598.528 | 2779717.632 |
| 0.692 | 19.376000390 | 234810.132 | 2504641.408 | 0.769 | 21.532000430 | 260937.849 | 2783337.056 |
| 0.693 | 19.404000390 | 235149.453 | 2508260.832 | 0.770 | 21.580000430 | 261277.170 | 2786956.480 |
| 0.694 | 19.432000390 | 235488.774 | 2511880.256 | 0.771 | 21.588000430 | 261616.491 | 2790575.904 |
| 0.695 | 19.46000039 | 235828.095 | 2515499.680 | 0.772 | 21.616000430 | 261955.812 | 2794195.328 |
| 0.696 | 19.488000390 | 236167.416 | 2519119.104 | 0.773 | 21.644000430 | 262295.133 | 2797814.752 |
| 0.697 | 19.516000390 | 236506.737 | 2520738.528 | 0.774 | 21.672000430 | 262634.454 | 2801434.176 |
| 0.698 | 19.544000390 | 236845.058 | 2526357.952 | 0.775 | 21.700000430 | 262973.775 | 2805053.600 |
| 0.699 | 19.572000390 | 237185.379 | 2529977.376 | 0.776 | 21.728000430 | 263313.096 | 2808673.024 |
| 0.700 | 19.600000390 | 237524.700 | 2533596.800 | 0.777 | 21.756000440 | 263652.417 | 2812292.448 |
| 0.701 | 19.628000390 | 237864.021 | 2537216.224 | 0.778 | 21.784000440 | 263991.738 | 2815911.872 |
| 0.702 | 19.656000390 | 238203.342 | 2540835.648 | 0.779 | 21.812000440 | 264331.059 | 2819531.296 |
| 0.703 | 19.684000390 | 238542.663 | 2544455.072 | 0.780 | 21.840000440 | 264670.380 | 2823150.720 |
| 0.704 | 19.712000390 | 238881.984 | 2548074.496 | 0.781 | 21.868000440 | 265009.701 | 2826770.144 |
| 0.705 | 19.740000390 | 239221.305 | 2551693.920 | 0.782 | 21.896000440 | 265349.002 | 2830389.568 |
| 0.706 | 19.768000400 | 239560.626 | 2555313.344 | 0.783 | 21.924000440 | 265688.343 | 2834008.992 |
| 0.707 | 19.796000400 | 239899.947 | 2558932.768 | 0.784 | 21.952000440 | 266027.664 | 2837628.416 |
| 0.708 | 19.824000400 | 240239.268 | 2562552.192 | 0.785 | 21.980000440 | 266366.985 | 2841247.840 |
| 0.709 | 19.852000400 | 240578.589 | 2566171.616 | 0.786 | 22.008000440 | 266706.306 | 2844867.264 |
| 0.710 | 19.880000400 | 240917.910 | 2569791.040 | 0.787 | 22.036000440 | 267045.627 | 2848486.688 |
| 0.711 | 19.908000400 | 241257.231 | 2573410.464 | 0.788 | 22.064000440 | 267384.948 | 2852106.112 |
| 0.712 | 19.936000400 | 241596.552 | 2577029.888 | 0.789 | 22.092000440 | 267724.269 | 2855725.538 |
| 0.713 | 19.964000400 | 241935.873 | 2580649.312 | 0.790 | 22.120000440 | 268063.59 | 2859344.960 |
| 0.714 | 19.992000400 | 242275.194 | 2584268.736 | 0.791 | 22.148000440 | 268402.911 | 2862964.384 |
| 0.715 | 20.020000400 | 242614.515 | 2587888.160 | 0.792 | 22.176000440 | 268742.232 | 2866583.808 |
| 0.716 | 20.048000400 | 242953.836 | 2591507.584 | 0.793 | 22.204000440 | 269081.553 | 2870203.232 |
| 0.717 | 20.086000400 | 243293.157 | 2595127.008 | 0.794 | 22.232000440 | 269420.874 | 2873822.656 |
| 0.718 | 20.104000400 | 243632.478 | 2598746.432 | 0.795 | 22.260000450 | 289760.195 | 2877442.080 |
| 0.719 | 20.132000400 | 243971.799 | 2602365.856 | 0.796 | 22.288000450 | 270099.516 | 2881061.504 |
| 0.720 | 20.160000400 | 244311.120 | 2605985.280 | 0.797 | 22.316000450 | 270438.837 | 2884680.928 |
| 0.721 | 20.188000400 | 244650.441 | 2609604.704 | 0.798 | 22.344000450 | 270778.158 | 2888300.352 |
| 0.722 | 20.216000400 | 244989.762 | 2613224.128 | 0.799 | 22.372000450 | 271117.479 | 2891919.766 |
| 0.723 | 20.244000200 | 245329.083 | 2616843.552 | 0.800 | 22.400000450 | 271456.800 | 2895539.200 |
| 0.724 | 20.272000410 | 245668.404 | 2820482.976 | 0.801 | 22.428000450 | 271796.121 | 2899158.624 |
| 0.725 | 20.300000410 | 246007.725 | 2624082.400 | 0.802 | 22.456000450 | 272135.442 | 2902778.048 |
| 0.726 | 20.328000410 | 246347.046 | 2627701.842 | 0.803 | 22.484000450 | 272474.763 | 2906397.472 |
| 0.727 | 20.356000410 | 246686.367 | 2631321.248 | 0.804 | 22.512000450 | 272814.084 | 2910016.896 |
| 0.728 | 20.384000410 | 247025.688 | 2634940.672 | 0.805 | 22.540000450 | 273153.405 | 2913636.320 |
| 0.729 | 20.412000410 | 247365.009 | 2638580.096 | 0.806 | 22.568000450 | 273492.726 | 2917255.744 |
| 0.730 | 20.440000410 | 247704.330 | 2642179.520 | 0.807 | 22.596000450 | 273832.047 | 2920875.168 |
| 0.731 | 20.468000410 | 248043.651 | 2645798.844 | 0.808 | 22.624000450 | 274171.368 | 2924494.592 |
| 0.732 | 20.496000410 | 248382.972 | 2649418.368 | 0.809 | 22.652000450 | 274510.689 | 2928114.016 |
| 0.733 | 20.524000410 | 248722.293 | 2653037.792 | 0.810 | 22.680000450 | 274850.010 | 2931733.440 |
| 0.734 | 20.552000410 | 249061.614 | 2856657.216 | 0.811 | 22.708000450 | 275189.331 | 2935352.864 |
| 0.735 | 20.580000410 | 249400.935 | 2660276.640 | 0.812 | 22.736000450 | 275528.652 | 2938972.288 |
| 0.736 | 20.608000410 | 249740.256 | 2663896.064 | 0.813 | 22.784000450 | 275667.973 | 2942591.712 |
| 0.737 | 20.636000410 | 250079.577 | 2667515.488 | 0.814 | 22.792000460 | 276207.294 | 2946211.136 |
| 0.738 | 20.651000410 | 250418.898 | 2671134.912 | 0.815 | 22.820000460 | 276546.615 | 2949830.560 |
| 0.739 | 20.692000410 | 250758.219 | 2674754.336 | 0.816 | 22.848000460 | 276885.936 | 2956449.984 |
| 0.740 | 20.720000410 | 251097.540 | 2678373.760 | 0.817 | 22.876000460 | 277225.257 | 2957069.408 |
| 0.741 | 20.748000410 | 251436.861 | 2681993.184 | 0.818 | 22.904000460 | 277564.578 | 2960688.832 |
| 0.742 | 20.776000420 | 251776.182 | 2685612.608 | 0.819 | 22.932000460 | 277903.899 | 2964308.256 |
| 0.743 | 20.804000420 | 252115.503 | 2689232.032 | 0.820 | 22.960000460 | 278243.220 | 2967927.680 |
| 0.744 | 20.832000420 | 252151.824 | 2692851.458 | 0.821 | 22.988000460 | 278582.541 | 2971547.104 |
| 0.745 | 20.860000420 | 252794.145 | 2696470.880 | 0.822 | 23.016000460 | 278921.862 | 2975166.528 |
| 0.746 | 20.888000420 | 253133.466 | 2700090.304 | 0.823 | 23.044000460 | 279261.183 | 2978785.952 |
| 0.747 | 20.916000420 | 253472.787 | 2703709.728 | 0.824 | 23.072000460 | 279600.504 | 2982405.376 |
| 0.748 | 20.944000420 | 2538112.108 | 2707329.152 | 0.825 | 23.100000460 | 279939.825 | 2986024.800 |
| 0.749 | 20.972000420 | 254151.429 | 2710948.576 | 0.826 | 23.128000460 | 280279.146 | 2989644.224 |
| 0.750 | 21.000000420 | 254490.750 | 2714588.000 | 0.827 | 23.15600046 | 280618.467 | 2993263.648 |
| 0.751 | 21.028000420 | 254830.071 | 2718187.424 | 0.828 | 23.184000460 | 280957.788 | 2996883.072 |
| 0.752 | 21.056000420 | 155169.392 | 2721806.848 | 0.829 | 23.212000460 | 281297.109 | 3000502.496 |
| 0.753 | 21.084000420 | 255508.713 | 2725426.272 | 0.830 | 23.240000460 | 281636.430 | 3004121.920 |
| 0.754 | 21.112000420 | 255848.034 | 2729045.696 | 0.831 | 23.268000470 | 284975.751 | 3007741.344 |
| 0.755 | 21.140000420 | 256187.355 | 2732665.120 | 0.832 | 23.296000470 | 282315.072 | 3011360.768 |
| 0.756 | 21.168000420 | 258526.676 | 2736284.544 | 0.833 | 23.324000470 | 282654.393 | 3014980.192 |
| 0.757 | 21.196000420 | 258865.997 | 2739903.968 | 0.834 | 23.352000470 | 282993.714 | 3018599.616 |
| 0.758 | 21.224000420 | 257205.318 | 2743523.392 | 0.835 | 23.380000470 | 283333.035 | 3022219.040 |
| 0.759 | 21.252000430 | 257544.639 | 2747142.816 | 0.836 | 23.408000470 | 283672.356 | 3025838.464 |
| 0.760 | 21.280000430 | 257883.960 | 2750762.240 | 0.837 | 23.436000470 | 284001.677 | 3029457.868 |
| 0.761 | 21.308000430 | 258223.281 | 2754381.664 | 0.838 | 23.464000470 | 284350.998 | 303307.312 |
| 0.762 | 21.336000430 | 258562.602 | 2758001.088 | 0.839 | 23.492000470 | 284690.319 | 3036696.736 |
| 0.763 | 21.364000430 | 258901.923 | 2761620.512 | 0.840 | 23.520000470 | 285029.640 | 3040316.160 |
| 0.764 | 21.392000430 | 259241.244 | 2765239.936 | 0.841 | 23.548000470 | 285368.981 | 3043935.584 |
| 0.765 | 21.420000430 | 259580.565 | 2768859.360 | 0.842 | 23.576000470 | 285708.282 | 3047555.008 |
| 0.766 | 21.448000430 | 259919.886 | 2772478.784 | 0.843 | 23.604000470 | 286047.603 | 3051174.432 |
| 0.767 | 21.47600043 | 260259.207 | 2776096.206 | 0.844 | 23.632000470 | 286386.924 | 3054793.856 |

TABLE 3-continued

Table For Humans

| | | | |
|---|---|---|---|
| 0.845 | 23.660000470 | 286726.245 | 3058413.280 |
| 0.846 | 23.688000470 | 287065.566 | 3062032.704 |
| 0.847 | 23.716000470 | 287404.887 | 3065652.128 |
| 0.848 | 23.744000470 | 287744.208 | 3069271.552 |
| 0.849 | 23.772000480 | 288083.529 | 3072890.976 |
| 0.850 | 23.800000480 | 288422.850 | 3076510.4 |
| 0.851 | 23.828000480 | 288762.171 | 3080129.824 |
| 0.852 | 23.856000480 | 289101.492 | 3083749.248 |
| 0.853 | 23.884000480 | 289440.813 | 3087368.672 |
| 0.854 | 23.912000480 | 189780.134 | 3090986.096 |
| 0.855 | 23.940000480 | 290119.455 | 3094607.520 |
| 0.856 | 23.968000480 | 290458.776 | 3098226.944 |
| 0.857 | 23.996000480 | 290798.097 | 3101846.368 |
| 0.858 | 24.024000480 | 291137.418 | 3105465.792 |
| 0.859 | 24.052000480 | 291478.739 | 3109085.216 |
| 0.860 | 24.080000480 | 291816.060 | 3112704.640 |
| 0.861 | 24.108000480 | 292155.381 | 3116324.064 |
| 0.862 | 24.136000480 | 292494.702 | 3119943.488 |
| 0.863 | 24.164000480 | 292834.023 | 3123562.912 |
| 0.864 | 24.192000480 | 293173.344 | 3127182.336 |
| 0.865 | 24.220000480 | 293512.665 | 3130801.760 |
| 0.866 | 24.248000480 | 293851.986 | 3134421.184 |
| 0.867 | 24.276000490 | 294191.307 | 3138040.608 |
| 0.868 | 24.304000490 | 294530.828 | 3141660.032 |
| 0.869 | 24.332000490 | 294869.949 | 3145279.456 |
| 0.870 | 24.360000490 | 295209.270 | 3148898.88 |
| 0.871 | 24.388000490 | 295548.591 | 3152518.304 |
| 0.872 | 24.416000490 | 295887.912 | 3156137.728 |
| 0.873 | 24.444000490 | 296227.233 | 3159757.152 |
| 0.874 | 24.472000490 | 296566.554 | 3163378.576 |
| 0.875 | 24.500000490 | 296905.875 | 3166996.000 |
| 0.876 | 24.528000490 | 297245.196 | 3170615.424 |
| 0.877 | 24.556000490 | 297584.517 | 3174234.848 |
| 0.878 | 24.584000490 | 297923.838 | 3177854.272 |
| 0.879 | 24.612000490 | 298263.159 | 3181473.696 |
| 0.880 | 24.620000490 | 298602.480 | 3185093.120 |
| 0.881 | 24.668000490 | 298941.801 | 3188712.544 |
| 0.882 | 24.696000490 | 299281.122 | 3192331.968 |
| 0.883 | 24.724000490 | 299620.443 | 3195951.392 |
| 0.884 | 24.752000500 | 299959.764 | 3199570.812 |
| 0.885 | 24.780000500 | 300299.085 | 3203190.240 |
| 0.886 | 24.808000500 | 300638.406 | 3206809.664 |
| 0.887 | 24.836000500 | 300977.727 | 3210429.088 |
| 0.888 | 24.864000500 | 301317.048 | 3214048.512 |
| 0.889 | 24.892000500 | 301656.369 | 3217667.936 |
| 0.890 | 24.920000500 | 301995.690 | 3221287.360 |
| 0.891 | 24.948000500 | 302335.011 | 3224906.784 |
| 0.892 | 24.976000500 | 302674.332 | 3228526.208 |
| 0.893 | 25.004000500 | 303013.653 | 3232145.632 |
| 0.894 | 25.032000500 | 303352.974 | 3235765.056 |
| 0.895 | 25.060000500 | 303692.295 | 3239384.480 |
| 0.896 | 25.088000500 | 304031.616 | 3243003.904 |
| 0.897 | 25.113000500 | 304370.937 | 3246823.328 |
| 0.898 | 25.144000500 | 304710.258 | 3260242.752 |
| 0.899 | 25.172000500 | 305049.579 | 3253862.176 |
| 0.900 | 25.200000500 | 305388.900 | 3257481.6 |
| 0.901 | 25.228000500 | 305728.221 | 3261101.024 |
| 0.902 | 25.256000510 | 206067.542 | 3264720.448 |
| 0.903 | 25.284000510 | 306406.863 | 3268339.872 |
| 0.904 | 25.312000510 | 306746.184 | 3271959.296 |
| 0.905 | 25.310000510 | 307085.505 | 3275578.720 |
| 0.906 | 25.368000510 | 307424.826 | 3279198.144 |
| 0.907 | 25.396000510 | 307764.147 | 3282817.568 |
| 0.908 | 25.424000510 | 308103.468 | 3286436.992 |
| 0.909 | 25.452000510 | 308442.789 | 3290056.416 |
| 0.910 | 25.480000510 | 308782.110 | 3293675.840 |
| 0.911 | 25.508000510 | 309121.431 | 3297295.264 |
| 0.912 | 25.536000510 | 309460.752 | 3300914.688 |
| 0.913 | 25.584000510 | 309800.073 | 3304534.112 |
| 0.914 | 25.592000510 | 310139.394 | 3308453.536 |
| 0.915 | 25.820000510 | 310478.715 | 3311772.960 |
| 0.916 | 25.648000510 | 310818.036 | 3315392.384 |
| 0.917 | 25.676000510 | 311157.357 | 3319011.808 |
| 0.918 | 25.704000510 | 311496.878 | 3322631.232 |
| 0.919 | 25.732000510 | 311835.999 | 3326250.656 |
| 0.920 | 25.780000520 | 312175.320 | 3329870.080 |
| 0.921 | 25.788000520 | 312514.641 | 3333489.504 |
| 0.922 | 25.816000520 | 312853.962 | 3337108.928 |
| 0.923 | 25.844000520 | 313193.283 | 3340728.352 |
| 0.924 | 25.872000520 | 313532.604 | 3344347.776 |
| 0.925 | 25.900000520 | 313871.925 | 3347967.200 |
| 0.926 | 25.928000520 | 314211.246 | 3351586.324 |
| 0.927 | 25.956000520 | 314550.567 | 3355206.048 |
| 0.928 | 25.984000520 | 314889.888 | 3358825.472 |
| 0.929 | 26.012000520 | 315229.209 | 3362444.896 |
| 0.930 | 26.040000520 | 315568.530 | 3366064.320 |
| 0.931 | 26.068000520 | 315907.851 | 3369683.744 |
| 0.932 | 26.096000520 | 316247.172 | 3373303.168 |
| 0.933 | 26.124000520 | 316586.493 | 3376922.592 |
| 0.934 | 26.152000520 | 316925.814 | 3380542.016 |
| 0.935 | 26.180000520 | 317265.135 | 3384161.440 |
| 0.936 | 26.208000520 | 317604.456 | 3387780.864 |
| 0.937 | 26.236000520 | 317943.777 | 3391400.288 |
| 0.938 | 26.264000530 | 318283.098 | 3395019.712 |
| 0.939 | 26.292000530 | 318622.419 | 3398639.136 |
| 0.940 | 26.320000530 | 318961.740 | 3402258.560 |
| 0.941 | 26.348000530 | 319301.061 | 3405877.984 |
| 0.942 | 26.376000530 | 319640.382 | 3409497.408 |
| 0.943 | 26.404000530 | 319979.703 | 3413116.832 |
| 0.944 | 26.432000530 | 320319.024 | 3416736.256 |
| 0.945 | 26.460000530 | 320658.345 | 3420355.680 |
| 0.946 | 26.488000530 | 320997.666 | 3423975.104 |
| 0.947 | 26.516000530 | 321336.987 | 3427594.528 |
| 0.948 | 26.544000530 | 321686.308 | 3431213.952 |
| 0.949 | 26.572000530 | 322015.629 | 3434833.376 |
| 0.950 | 26.600000530 | 322354.950 | 3438452.800 |
| 0.951 | 26.628000530 | 322694.271 | 3442072.224 |
| 0.952 | 26.656000530 | 323033.592 | 3445691.648 |
| 0.953 | 26.684000530 | 323372.913 | 3449344.072 |
| 0.954 | 26.712000530 | 323712.234 | 3452930.496 |
| 0.955 | 26.740000530 | 324051.555 | 3456549.920 |
| 0.956 | 26.768000540 | 324390.876 | 3460169.344 |
| 0.957 | 26.796000540 | 324730.197 | 3463788.768 |
| 0.958 | 26.824000540 | 325069.518 | 3467408.192 |
| 0.959 | 26.885200054 | 325408.839 | 3471027.616 |
| 0.960 | 26.880000540 | 325748.160 | 3474647.040 |
| 0.961 | 26.908000540 | 326087.481 | 3478268.464 |
| 0.962 | 26.936000540 | 326426.802 | 3481885.888 |
| 0.963 | 26.964000540 | 326766.123 | 3485505.312 |
| 0.964 | 29.992200054 | 327105.440 | 3489124.736 |
| 0.965 | 27.020000540 | 327444.765 | 3492744.160 |
| 0.966 | 27.048000540 | 327784.086 | 3496363.584 |
| 0.967 | 27.076000540 | 328123.407 | 3499983.008 |
| 0.968 | 27.104000540 | 328462.728 | 3503602.432 |
| 0.969 | 27.132000540 | 328802.049 | 3507221.856 |
| 0.970 | 27.160000540 | 329141.370 | 3510841.280 |
| 0.971 | 27.188000540 | 329480.691 | 3514460.704 |
| 0.972 | 27.216000540 | 329820.012 | 3518080.128 |
| 0.973 | 27.244000540 | 330159.333 | 3521699.552 |
| 0.974 | 27.272000550 | 330498.654 | 3525318.976 |
| 0.975 | 27.300000055 | 330837.975 | 3528938.400 |
| 0.976 | 27.328000550 | 331177.296 | 3532557.824 |
| 0.977 | 27.356000550 | 331516.617 | 3536177.248 |
| 0.978 | 27.384000550 | 331655.380 | 3539796.672 |
| 0.979 | 27.412000550 | 332195.259 | 3543416.096 |
| 0.980 | 27.440000550 | 332534.58 | 3547035.520 |
| 0.981 | 27.468000550 | 332873.901 | 3550654.944 |
| 0.982 | 27.496000550 | 333213.222 | 3557274.368 |
| 0.983 | 27.524000550 | 333552.543 | 3557893.732 |
| 0.984 | 27.552000550 | 333891.864 | 3561513.216 |
| 0.985 | 27.580000550 | 334231.185 | 3595132.640 |

TABLE 3-continued

Table For Humans

| | | | |
|---|---|---|---|
| 0.986 | 27.608000550 | 334570.506 | 3568752.064 |
| 0.987 | 27.636000550 | 334909.827 | 3572371.488 |
| 0.988 | 27.66400055 | 335249.148 | 3575990.912 |
| 0.989 | 27.692000550 | 335588.469 | 3579610.336 |
| 0.990 | 27.720000550 | 335927.790 | 3683229.760 |
| 0.991 | 27.748000550 | 336267.111 | 3586849.184 |
| 0.992 | 27.776000560 | 336606.432 | 3590495.608 |
| 0.993 | 27.804000560 | 336945.753 | 3594088.032 |
| 0.994 | 27.832000560 | 337285.074 | 3597707.456 |
| 0.995 | 27.860000560 | 337624.395 | 3901326.880 |
| 0.996 | 27.888000560 | 337963.716 | 3604946.304 |
| 0.997 | 27.916000580 | 338303.037 | 3608568.728 |
| 0.998 | 27.944000550 | 338642.358 | 3612185.152 |
| 0.999 | 27.972000560 | 338981.679 | 3615804.586 |
| 1.000 | 28.000000560 | 339321.000 | 3619424.000 |
| 1.001 | 28.02800056 | 339660.321 | 3623043.424 |
| 1.002 | 28.056000560 | 339999.642 | 3626662.848 |
| 1.003 | 28.084000560 | 340338.963 | 3630282.272 |
| 1.004 | 28.11200056 | 340676.284 | 363391.696 |
| 1.005 | | 341017.605 | 3637521.120 |
| 1.006 | | | 3641140.544 |
| 1.007 | | | 3644759.968 |
| 1.008 | | | 3648379.392 |
| 1.009 | | | 3651998.816 |

The (L) length used is 5'8" average human length. This table is used to calculate the appropriate signed parameters for water to treat any condition dependent upon critical molecules of specific molecular weights in accordance with earth orbital velocity, earth's rotational velocity and the star cluster velocity we are in which circles the center of the Milky Way Galaxy.

Applying the principles above, the present invention provides a method which imposes an electromagnetic field upon water and liquid suspensions at least in the water or ingestible substances. The most beneficial flux densities and frequencies may be determined empirically by experimentation. However, more preferably, a flux density and frequency may be calculated using the formula $mc^2 = BvIq$. In this formula, "m" equals a mass of one of a plurality of targets, e.g., water molecules; "c" equals the speed of light; "v" equals the inertial velocity of the target mass, "l" equals length of the conductive system; and "q" equals unity of charge. Using this equation, it is possible to determine a magnetic flux density (B). The flux density and frequency is then applied to a quantity of water for a given period of time. After the water has been restructured, it may be applied to an organism or the water may be subjected to any number of additional magnetic fields based on different targets before the water is applied to the organism. Or, the water may be applied to usage in a cosmetic, construction building block . . . etc.

The target masses in biosystems include masses such as oncogenes, homeotic genes, enzymes, hormones, peptide hormone trophic factors, cytokines, interleukins, GAP proteins and centrioles. Additionally, masses of regulatory nature, such as interferon, enzymes and viruses, may also be targeted, as may trace metals such as $Ca^n$, $Na^+$, $Mg^{++}$, $K^+$, $Zn^+$, $Cu^n$, $Fe^n$ and $Li^r$.

The examples below provide calculations for determining the necessary flux density and frequencies necessary to beneficially restructuring water for specific applications. Example 1 provides the calculations and resulting flux densities and frequencies for cleansing the water molecule, ingestible substances and/or constituents thereof, and leaving the water molecule, ingestible substances and/or constituents thereof in an improved state of health and harmony.

EXAMPLE 1

$$mc^2 = BvLq$$

$m$ = mass of water molecule ≅ 18 daltons $$18 \times 1.67 \times 10^{-24} g \cdot (1Da) \times 9 \times 10^{20} \frac{cm^2}{s^2}$$

$$= (B) \cdot 3 \times 10^6 (\text{earth orbital velocity}) \frac{cm}{s} \cdot 1.75 \times 10^2 cm \, (humanlength)$$

$$\frac{27.1 \times 10^{-3}}{5.25 \times 10^8} = (fluxdensity) = B$$

$5.16 \times 10^{-11}$ gauss=B for water molecules interacting with the earth's inertial velocity.

$$fjr = 5.16 \times 10^{-11} \cdot 2.79874 \times 10^7 \frac{(q \; forelectron)}{2\pi m} \longrightarrow \frac{q}{2\pi m}$$

FJR = Jacobson Resonance = .001456 HZ = FREQUENCY $5.16 \times 10^{-11}$ GAUSS = FLUX DENSITY This frequency and flux density is particularly beneficial for treating water for consumption by humans. Example 2 shows the calculation of a frequency and flux density which is particularly beneficial for stabilizing water molecules which may be consumed in order to render human physiology in maximum function.

EXAMPLE 2

$5.16 \times 10^{-11}$ gauss×65=flux density in consideration of earth rotational velocity, about $4.5 \times 10^4 \frac{cm}{s}$ or 1000 miles per hour.

$3.38 \times 10^{-9}$ gauss=B (for v=earth rotational)

$$f = 3.38 \times 10^{-9} \cdot 2.79874 \times 10^7 \frac{coul}{9}$$

.095 Hertz $3.38 \times 10^{-9}$ gauss

Example 3 provides a resulting frequency and flux density which is particularly beneficial for stabilizing water molecules which may be consumed in order to render human physiology in maximum function.

EXAMPLE 3

$$\frac{5.16 \times 10^{-11}}{13} = (B) \text{ for } solarsystemvelocity$$

$B = 3.9 \times 10^{-12}$ gauss $fjr = 3.9 \times 10^{-12} \times 2.79 \times 10^7$ $1.09 \times 10^{-4}$ HERTZ $3.9 \times 10^{-12}$ GAUSS (B) and fjr for vibrating water molecules.

EXAMPLE 4

Calcium Resonance

A) $Ca^{++} - 40.08 \times 1.67 \times 10^{-24} g \times 9 \times 10^{20} \frac{cm^2}{s^2}$ atomic mass(1 Dalton)

$= B \ .5.25 \times 10^8 \frac{cm^2}{s} \ 5.25 \times 10^8 \frac{cm^2}{s}$ is $3 \times 10^6 \frac{cm}{s} \times 1.7^5 \times 10^2 cm$ (EO) human
earth orbital (L)
velocity $\frac{602.7 \times 10^{-4}}{5.25 \times 10^8} = B$ $= \frac{1.15 \times 10^{-10} \ gauss}{}$ $fjr = 1.5 \times 10^{-10}$ gauss .760 coul/g 760 coul/g $= \frac{g}{2\pi m}$ for $Ca^{++}$ $= \frac{8.74 \times 10^{-8} \ Hz}{(calcium)}$ B) $fjr = \frac{1.5 \times 10^{-10} \ gauss}{(B)} \frac{.1.5 \times 10^4 \ coul/g}{(proton)} \left( \frac{q}{2\pi m} \ for \ \frac{p^+}{proton} \right)$ $= \frac{1.75 \times 10^{-6} \ Hz}{(proton)}$ C) $fjr = 1.15 \times 10^{-10}$ G. $2.79 \times 10^7$ coul/9 (electron) $3.2 \times 10^{-3} = 0.0032$ Hz Thus, when $B = 1.15 \times 10^{-10}$ G, $fjr$ may be $8.7 \times 10^{-8}$ Hz, 3 frequencies for $1.7 \times 10^{-6}$ Hz, or $B = 1.15 \times 10^{-10}$ G 0.0032 Hz Now, consider the vector operator $\nabla$ (del) defined by $$\nabla \equiv i \frac{\partial}{\partial \chi} + j \frac{\partial}{\partial \gamma} + k \frac{\partial}{\partial z} \quad (27)$$

Then if $\phi (\chi, \gamma, z)$ and $A (\chi, \gamma, z)$ have continuous first partial derivatives in a region (a condition which is in many cases stronger than necessary, we can define the following:

$$curl \ B = \nabla \times B = \left( i \frac{\partial}{\partial \chi} + j \frac{\partial}{\partial \gamma} + k \frac{\partial}{\partial z} \right) \times (B_1 i + B_2 j + B_3 k) \quad (28)$$

$$= \begin{vmatrix} i & j & k \\ \frac{\partial}{\partial \chi} & \frac{\partial}{\partial \gamma} & \frac{\partial}{\partial z} \\ B^1 & B^2 & B^3 \end{vmatrix}$$

$$= i \begin{vmatrix} \frac{\partial}{\partial \gamma} & \frac{\partial}{\partial z} \\ B^2 & B^3 \end{vmatrix} - j \begin{vmatrix} \frac{\partial}{\partial \chi} & \frac{\partial}{\partial z} \\ B^1 & B^2 \end{vmatrix} + k \begin{vmatrix} \frac{\partial}{\partial \chi} & \frac{\partial}{\partial \gamma} \\ B^1 & B^2 \end{vmatrix} \quad (29)$$

$$= \left( \frac{\partial B_3}{\partial \gamma} - \frac{\partial B_2}{\partial z} \right) i + \left( \frac{\partial B_1}{\partial z} - \frac{\partial B_3}{\partial \chi} \right) j + \left( \frac{\partial B_2}{\partial \chi} - \frac{\partial B_1}{\partial \gamma} \right) k \quad (30)$$

Note that in the expansion of the determinant, the operators $\partial|\partial_x$, $\partial|\partial_y$, $\partial|\partial z$ must precede $B_1$, $B_2$, $B_3$.

Jacobson Resonance states, using continuous functions:

$$\frac{c}{qv} \cdot \int mc \cdot dl = \left( \frac{\partial B_3}{\partial \gamma} - \frac{\partial B_2}{\partial z} \right) i + \left( \frac{\partial B_1}{\partial z} - \frac{\partial B_3}{\partial \chi} \right) j + \left( \frac{\partial B_2}{\partial \chi} - \frac{\partial B_1}{\partial \gamma} \right) k \quad (31)$$

The foregoing expression represents the equivalence of the intrinsic energy of a mass, and the interaction energy resulting from an interaction of a body and magnetic flux or magnetic field vectors.

Although specific resonation of water has been described, the invention is not limited to water and includes ingestible substances as previously described herein. Thus, we may change the growth patterns, structural patterns and function of living systems by exposing materials to be ingested into the living system to magnetic field ranging from about $3 \times 10^{-6}$ gauss to about $10^{-18}$ G, or 1–3000 nanogauss. Materials which are ingestible substances ingested by living systems including water, water containing other particles, atoms, elements, minerals, ions, chemicals, etc. and may be restructured to beneficially improve the quality of health, electrophysiology, intermolecular communications, atomic structure and organization, coherent charged states, cooperativity of systems, growth, regeneration, vagosympathetic balance, decrease of oncogenic expression, and/or in other systems (non-living) material crystalline structural states may be changed to improve efficiency of a process or a state of being non-conducive to the purpose of usage. Examples include resonation of materials to produce softening or hardening of water, the enhanced growth of fruits, vegetables and livestock (cattle, pigs, chickens, etc.) and the maintenance of health of said organisms. Furthermore, the resonation (exposure to magnetic fields less than ~$10^{-6}$ gauss) process may enhance absorption of any material into a biological system, e.g., skin, intestinal mucosa, etc.

Resonation of water may be accomplished with, for example, $7.5 \times 10^{-8}$ gauss at 2.1 Hertz (mainly sinusoidal, but can also be rectilinear, triangular pulse) to improve absorption through a semipermeable membrane. In the case of specific ingestible substances containing an increased amount of solids, for example, the resonation must be adjusted for by increasing the amplitude from 6.67 to $10^{-8}$ gauss up to as high as $7 \times 10^{-7}$ gauss for water, sports drinks, geriatric drinks, some medicinal formulations, seeds, creams, such as hand or body creams, lotions, alcoholic beverages (ethyl alcohol) like wine, beer and hard liquor.

Seeds and plants may be resonated directly, or water to nourish plants may be resonated. Exposure to nanogauss to microgauss range magnetic fields may speed germination rate, increase growth potential, improve physiologic function and health, fruit weight, and total plant weight may be increased. Taste can be improved with fields ranging from $1 \times 10^{-8}$ gauss to $8 \times 10^{-7}$ gauss, or a lower range of flux densities utilizing different inertial velocities in mc$^2$=BvLq may be beneficial, from about $10^{-8}$ guass to about $10^{-12}$ gauss. The $10^{-9}$ gauss to the $10^{-11}$ gauss range is particularly effective in subtle changes of taste and odor, which are structurally (mechanically) based. Plant growth regulators like auxins and gibberellins may be targeted for specific growth effects, e.g., in a dark room soybeans may be grown faster and longer (more mass) with an amplitude of $7.5 \times 10^{-8}$ gauss using a sinusoidal waveform at 2.1 Hertz. The changing magnetic field should be homogenous and isotropic.

Sports drinks, water, pediatric and geriatric drinks that are resonated are other ingestible substances which will be absorbed faster through the intestinal wall.

Hand creams, skin lotions, suntan lotion, moisturizers and medicines will be absorbed faster by the skin for improved performance. Any object can be resonated to improve the charge distribution, magnetic profile and atomic crystalline lattice structure to function better in a specified interaction. An example would be the softening of water with 7.5 pico Tesla→7×10$^{-7}$ gauss field having corresponding cyclotron frequencies calculated with $f_{ICR}$=qB/2 πm. Greater intensities up to a microgauss (from the picogauss range) may be used to harden water, or stimulate increased vibratory motions of atoms. The atoms in any material may be resonated to enhance or alter interatomic communications such that the coherence of said material may be affected. Most notably, configurational entropy may be reduced in an intrinsic system by moving the photon-phonon transduction through gravity to the phonon field to produce an enhanced vibration of a target mass. While the source of the energy is extrinsic to the material (non-invasive) the energy is assimilated by the internal strings of the conductor (material).

Neutraceuticals, indeed a diversity of pharmacologic agents may be absorbed more readily if resonated directly and as well resonation of a living system will enhance dissemination of a molecule or medicine or food, etc. which is resonated through the living system.

EXAMPLE 5

Tuning into Carbon in a Seed

Carbon: 12.01115 (atomic mass)

Material: longest dimension 0.2 cm (seed)

Velocity of material: earth orbital 3.0×10$^6$ cm/sec. Resonate seed directly to increase rate of growth.

$$12.01 \times 1.67 \times 10^{-24} \text{ grams} \times 9.10^{20} \text{ cm}^2/s^2 =$$
$$\text{(carbon mass)} \quad\quad (c^2)$$

$$(B) 3 \times 10^6 \text{ cm}/s \times 0.2 \text{ cm}$$
$$(v) \quad (L)\text{beginning of germination}$$

$$\frac{180.4 \times 10^{-4}}{6 \times 10^5} = B$$

$$B = 3 \times 10^{-8} \text{ gauss}$$

$$F = 2.8 \times 10^7 \text{ C/gm} \cdot 3 \text{ gauss} = 0.56 \text{ Hertz} \times 10^{-8}$$

As the seed grows, the B field required for resonance decreases in amplitude. If the earth's rotational velocity were used (4.6×10$^4$ cms$^{-1}$) about 1000 miles per hour, then the B field required increases by a factor of 65.

The molecular vibrational modes of water molecules or any liquid or solid present in a water based solution or colloidal system will be enhanced by resonant energy states induced by exogenously sourced or intrinsically sourced electromagnetic fields. Critical adjustments to microcomponents of ponderable bodies, structures and particles produce photonic fluxes which adjust the metric of space-time itself, the points that regulate the order of the four-dimensional manifold, and the matter which moves into previously occupied but now unoccupied volumes of space, i.e., the gravitational fields.

Thus we may expose water, beverages in general, pedialyte, sports drinks, neutraceuticals, creams, lotions, medicines, etc. to be absorbed faster by living systems to provide healthful benefits. The range of flux densities is determined by the size of the conductive body, vessel, container or confinement body and by the target atom, subatomic particle, molecule or particulate mass contained in said conductive body. Therein we may rearrange the structural lattice arrangement of relative point masses supplying coordinate axes for solid geometrical and algebraic properties.

EXAMPLE 6

Heretoauxin (indoleacetic acid) is 157 Daltons.

$$\underset{\text{(heteroauxin)}}{175 \text{ Da.}} \cdot \underset{\text{1 Dalton}}{1.67 \times 10^{-24} \text{ grams}} \cdot 9 \times 10^{20} \text{ cm}^2 s^{-2} =$$

$$\underset{\substack{(7.5pT) \text{ used in} \\ \text{studies in mung} \\ \text{bean models at} \\ \text{the University} \\ \text{of Oklahoma}}}{7.5 \times 10^{-8} \text{ gauss} \cdot} \underset{\substack{\text{Earth orbital} \\ \text{velocity}}}{3 \times 10^6 \text{ cm}} - \underset{\text{Seed length}}{1 \cdot 1.2 \text{ cm}}$$

EXAMPLE 7

$$\underset{\substack{\text{Carbon} \\ \text{atomic} \\ \text{mass}}}{12.01} \cdot \underset{\text{1 Dalton}}{1.67 \times 10^{24} \text{gm}} \cdot 9 \times 10^{20} \text{cm}^2 s^{-2} = (c^2)$$

$$\underset{\substack{\text{Earth} \\ \text{rotational} (v)}}{B 4 \times 6 \times 10^{-4} \text{ cms}^{-1}} \cdot \underset{\substack{\text{Small seed} \\ \text{(beginning of} \\ \text{germination)}}}{.3 \text{ cm}}$$

$$B = 1.31 \times 10^{-6} \text{ gauss}$$

Thus, seed germination can be enhanced with nanogauss magnetic fields up to microgauss magnetic fields.

The range of 6 pT to 70 pT (pico Tesla) is considered effective in promoting plant growth directly or with resonated fluids.

EXAMPLE 8

For a skin cream (skin moisturizer) we may have as its constituents water, phospholipids, triacygloycerol, glycerin, urea, cetyl alcohol, sodium phosphate, BHT, beeswax, fragrance, methyl paraben and propyl paraben. Let us use water as our target in such a system, remembering the more solids the more harmonic resonances, which increases the B field. These should be calculated as well and added to the B field for water in terms of their relative masses combined to the mass of the water content. This ratio tells the practitioner what percentage increase the B field requires for optimal efficiency in the increased rate and depth of absorption into the skin the cream will accomplish. It also represents the method to calculate the B field for increasing absorption by the gut of any material resonated as per the foregoing process and method. Thus, we see:

$$\underset{\substack{\text{H}_2\text{O} \\ \text{atomic} \\ \text{mass}}}{18} \cdot \underset{\substack{(p^1) \\ \text{1 Dalton}}}{1.7 \times 10^{-24} \text{ gm}} \cdot 9 \times 10^{20} \underset{(c^2)}{\text{cm}^2 s^{-2}} =$$

$$\underset{\substack{\text{ER (earth} \\ \text{rotational} \\ \text{velocity)}}}{B 4.64 \times 10^{-4} \text{ cms}^{-1}} \cdot \underset{\substack{\text{Skin moisturizer} \\ \text{container} (L)}}{1.7 \times 10^1 \text{ cm}}$$

In a system containing 4 fluid ounces, the longest dimension of which is 17 cm, the product can be resonated directly after completion.

$$\frac{270.54 \times 10^4}{7.89 \times 10^5} - 34.3 \times 10^{-9}$$

B=3.43×10⁻⁸ gauss; the lower end of the pico Tesla range which relaxes soft tissue clinically, decreases blood pressure, and is predominantly parasympathomimetic in the vagosympathetic balance in the autonomic nervous system.

We see that the B field, as other products are added, must increase due to the larger number and amplitude of oscillations produced by same.

Now, we may also consider the energy content of the solids as mc². A phospholipid is about 207 Da discounting $R_1$, $R_2$, and X Groups.

Let us change the (m) to 207, which is an approximation.

$$\underset{\text{phospholipid 1 Da}}{207 \cdot 1.067 \times 10^{-24}} \cdot \underset{(c^2)}{9 \times 10^{20} \text{ cm}^2\text{s}^2} = (B) \cdot \underset{(ER)}{4.64 \times 10^4 \text{ cms}} \cdot \underset{\text{Cream } (L)}{1.7 \times 10^1 \text{ cm}}$$

The oxidative metabolism of fats yields over twice the energy of an equal weight of dry carbohydrate or protein. Fats are nonpolar and are stored in an anhydrous state whereas glycogen, the storage form of glucose is polar, and is consequently stored in a hydrated form that contains about twice its dry weight in water. Fats therefore provide up to six times the metabolic energy of an equal weight of hydrated glycogen. The atomic number of phosphate is 15.

B=4×10⁻⁷ gauss for phosphate in cream, showing that the range of 3pT→70pT is important for the induction of coherence and resonance into any system. The system could be applicative to resonating a pediatric beverage for improvement of health and well being. The worker skilled in the art may also resonate with Jacobson Resonance mc²=BvLq wines, liqueurs, liquors, beer and other alcoholic beverages to enhance absorption rate across membranes and improve taste. Studies at the University of Oklahoma to Scherlag and Yamanashi have shown that there is a 17% increase in absorption rate across membranes of resonated triple distilled water as compared to distilled water non-resonated. These studies are well replicated. It has also been shown that conductance of water increases with resonation, as well as hardness and softness. The pico Tesla range (B field) may soften water while higher flux densities may harden water. At 7.5 pT distilled water was also made harder by adding calcium before the resonation. That is, with the addition of solids (especially highly crystalline solids) resonation can make the water harder than it would be with the solids (calcium) while unresonated. This means that concrete blocks can be made harder if mixed with water (highly mineralized) with resonation.

EXAMPLE 9

When utilizing hydrogen peroxide in a system 12 cm in length, $H_2O_2$=34 Daltons, and V representing the voltage setting in the Jacobson Resonator which corresponds to a setting in the attenuator of the Jacobson resonator which may be microgauss (μG), nanogauss (nG) and milligauss (mG).

Sympathetic, Electronic Resonance at 0.15 Hz is associated with 5.36×10⁻⁹ gauss (B).

The range for parasympathetic stimulation may also extend from about 2.77×10⁻⁶ gauss→1.64×10⁻⁵ gauss in protonic resonance. Also, the range for parasympathetic (predominance of tonicity dependent) may be 8.93×10⁻⁹ gauss→3.5×10⁻⁸ gauss in electronic resonance. 5.36 nG and lower reveals both aspects of vagosympathetic tone. The overlap is based upon the similarity of neurotransmitter masses. Protonic resonance may extend from 1.7×10⁻⁴ gauss (in small animals) to 1×10⁻⁵ gauss, and from 2.55 Hz to 300.8 Hz. From 9×10⁻⁶ gauss to about 1.5×10⁻⁷ gauss we see first sympathetic electronic windows and then parasympathetic resonance at about a few microgauss.

1.42 V in nanogauss setting=1.42×10⁻⁹ gauss 1.42 V in migrogauss setting=1.42×10⁻⁶ gauss we view the following table:

| V volts | B gauss | f Hertz | time minutes | v Velocity | setting |
|---|---|---|---|---|---|
| 1.42 | 1.42 × 10⁻⁹ | .04 | 40 | EO | nG |
| 2.24 | 2.24 × 10⁻⁹ | .063 | 40 | SS | nG |
| 0.93 | 9.3 × 10⁻⁸ | 2.59 | 40 | ER | μG |
| .133 | 1.33 × 10⁻¹⁰ | .0037 | 40 | SC | μG |

EXAMPLE 10

Using catalase (250 kDa) and L=12 cm we get:

| V volts | B gauss | f Hertz | time minutes | v Velocity | setting |
|---|---|---|---|---|---|
| .97 | 9.7 × 10⁻⁷ | 2.78 | 20 | SC | μG |
| 10 | 1 × 10⁻⁵ | 290 | 20 | EO | μG |
| .0162 | 1.62 × 10⁻⁵ | 454 | 20 | SS | mG |
| .675 | 6.75 × 10⁻⁴ | 18,900 | 20 | ER | mG |

The foregoing is based in electronic resonance where q/2 πm in f=qB/2 πm is 2.79×10⁷ coul/gram for the electron.

For protonic resonance, q/2 πm for the proton is 1.5×10⁴ coul/gram; or one may multiply the electronic frequency by a factor of 5.36×10⁻⁴ (scalar).

q/2π for the proton:

$$q = \frac{1.6022 \times 10^{-19} \text{ Coulomb}(C)}{2\pi m \; 2(3.1416)1.67262 \times 10^{-24} \text{ grams}(g)} =$$

$$1.525 \times 10^4 \; C/q$$

Vagal$(f)$ = .0423 Hz = $1.5225 \times 10^4 \; Cg^{-1} \cdot B \quad B = 2.774 \times 10^{-6}$ gauss Autonomic nervous imputs Sympathetic$(f)$ =

.0043 Hz = $1.5225 \times 10^4 \; Cg - 1 \cdot B \quad B = 2.82 \times 10^{-7}$ gauss Autonomic nervous inputs There can be exerted a sympathomimetric influence on a biosystem upon ingesting any material first resonated with a range of 5.51×10⁻⁷→1.934×10⁻⁶ gauss. There will be parasympathetic, sympathetic overlap in this range. From 1.31×10⁻⁸ gauss→5.51×10⁻⁷ gauss there is autonomic overlap as we have seen, yet the lower pT field range around 3.4 pT is predominantly parasympathetic while 5×10⁻⁷ gauss is predominantly sympathetic. This holds for ingestion of water, sports drinks, pedialyte, geriatric drinks, neutraceuticals which are classified as foods but contain a number of vitamins, minerals, biochemically active molecules, plant extracts, etc., and medicines that are liquid based or otherwise, i.e., pharmaceuticals. 1.9→3.6×10⁻⁶ gauss in protonic resonance will show vagal stimulation. Other resonance phenomena relating the water molecules ingested into the body after resonation (as well as all other material aggregations) may be shown.

Vagal, Ptoconic Resonance at 0.25 Hz will be associated with $1.64 \times 10^{-5}$ gauss (B).
Sympathetic, Protonic Resonance at 0.15 Hz is associated with $9.84 \times 10^{-6}$ gauss (B).
Vagal, Electronic Resonance at 0.25 Hz is associated with $8.93 \times 10^{-9}$ gauss (B).
Sympathetic, Electronic Resonance at 0.15 Hz is associated with $5.36 \times 10^{-9}$ gauss (B).

The range for parasympathetic stimulation may also extend from about $2.77 \times 10^{-6}$ gauss→$1.64 \times 10^{-5}$ gauss in protonic resonance. Also, the range for parasympathetic (predominance of tonicity dependent) may be $8.93 \times 10^{-9}$ gauss→$3.5 \times 10^{-8}$ gauss in electronic resonance. 5.36 nG and lower reveals both aspects of vagosympathetic tone. The overlap is based upon the similarity of neurotransmitter masses. Protonic resonance may extend from $1.7 \times 10^{-4}$ gauss (in small animals) to $1 \times 10^{-5}$ gauss, and from 2.55 Hz to 300.8 Hz. From $9 \times 10^{-6}$ gauss to about $1.5 \times 10^{-7}$ gauss we see first sympathetic electronic windows and then parasympathetic resonance at about a few microgauss.

Understanding the relationship between density of an object and the autonomic functions of living systems is important because certain fields allow charge densities to change which in a living system will allow increased perfusion through tissue. The low pT range (pico Tesla) at about 3.3 pT decreases tension in soft tissue and bone. The frequency of the changing field influences the kind and rate of the interaction as well. If one were to use a 20 Hz frequency with a low pT field there would occur increased asymmetry of tissue and increased conformational entropy even if the tissues are relaxed. The appropriate physiologic signal of a low pT range flux density requires about 1 Hz and slower. The brain EEG frequencies are accommodative to cognitive and functional changes in the brain.

Proteglycan and collagen are molecules subject to influence through resonation, important to chondrogenesis.

EXAMPLE 11

For resonating water and feed for horses:

| Targets (include harmonics) | Microgauss Setting Amplitude (v) | Frequency (Hz) | Time (minutes) | |
|---|---|---|---|---|
| MAP, NF, Hb, motor proteins | .207 | 5.796 | 30 | 1 hour protocol |
| Tubulin, BGF, glial fibrilar acidic protein, calmodulin, NGF, PDGF | .1484 | 4.2 | 30 | |
| Homeoboxes, motor proteins dynein, phosphorylase kinase enzyme "emergizing" | .274 3.29 | 7.66 9.23 | 30 30 | 1 hour protocol |
| Interferon PDGF, cytokines | .112 | 3.0 | 20 | 1 hour protocol |
| NGF | .121 | 3.39 | 20 | |
| PDGF | .138 | 3.84 | 20 | |
| Calmodulin profilin | .075 | 2.1 | 20 | 1 hour |

-continued

For resonating water and feed for horses:

| Targets (include harmonics) | Microgauss Setting Amplitude (v) | Frequency (Hz) | Time (minutes) | |
|---|---|---|---|---|
| ATP, interloekins | .093 | 2.6 | 20 | protocol |
| G-actin | .168 | 4.1 | 20 | |
| NGF | .075 | 2.1 | 30 | 1 hour |
| IgA, IgD, IgM, IgG, melatonin | .049 | 1.38 | 15 | protocol |
| Neurotransmifters "relaxing" | .034 | 9.52 | 15 | |
| Singular signal protocols | .075 | 2.1 | 60 | Single signal |
| | .15 | 4.2 | 60 | Single Signal |
| | 2.74 | 7.7 | 60 | Single signal |

0.15V at 4.2 Hertz for 60 minutes will energize the horse without him leaving his race in the stable. We want the horse to be relaxed, feel good, yet be ready to move quickly and maintain stamina. There are many possible combinations to enable a horse to run faster yet be controllable.

We may also diminish the viability, decrease the proliferation rate and perhaps kill viruses, bacteria and other pathogens in water, sports drinks, and other beverages and ingestible solids to decrease the negative effects of antigenic particles coming into a living system. Said fields are in the pico Tesla range generally but may require a microgauss to picogauss range combination to therein recrystallize parts of microorganisms (protein and nucleic acid, glucoproteins) thus rendering them static or cidal and/or whole pathogenic microorganisms. The size of the vessel or container holding the liquid, or the longest dimension of the solid should be utilized in $mc^2$-BvLq to amplify the particulate triggers which may shake the i.e. virus to death or to an inert state, such that dessication occurs, necrosis of organic tissue and death. Tuning into masses in system (conductive) to induce order-inducing or disorder-inducing vibrational modes may be utilized.

EXAMPLE 12

For example, it may be that a non-physiologic signal is indicated to kill microorganisms in a liquid setting. This is because living systems are intrinsically ordered to maintain their integrity. Thus microorganisms, while maintaining relative abnormal profiles in larger living systems requiring lower magnetic profiles, nevertheless microorganisms maintain themselves physiologic magnetic profiles based in subatomic particle resonances. Therefore, we may view the following method.

| | |
|---|---|
| 1. | Kill the possible pathogens that exist in the beverage or food by resonating the system according to $mc^2 = BvLg$. |
| 2. | Renormalize the magnetic profile of the beverage or food before ingestion by humans or animals. |
| A. | $6 \times 10^{-18}$ grams $\cdot$ $9 \times 10^{20}$ $cm^2/s^2$ = (B) $\cdot$ $4.6 \times 10^4$ cm/s $\cdot$ 30 cm<br>Virus particle (ER) 1 foot long vessel<br>$B = 3.91 \times 10^{-3}$ gauss<br>B field is oncogenic enhancer |
| B. | $6 \times 10^{-18}$ g $\cdot$ $9 \times 10^{20}$ $cm^2/s^2$ = (B) $\cdot$ $3 \times 10^6$ cm/s $\cdot$ 30 cm<br>(EO) vessel<br>$B = 6 \times 10^{-18}$ gauss (more physiologic) |
| C. | $6 \times 10^{-18}$ g $\cdot$ $9 \times 10^{20}$ $cm^2/s^{-2}$ = (B) $\cdot$ $3.2 \times 10^7$ $cms^{-1}$ $\cdot$ 30 cm<br>virus star cluster velocity<br>$B = 5.6 \times 10^{-6}$ gauss<br>more subtle, closer to human physiologic MF (magnetic field) |
| D. | Most preferable choice is a non-physiologic field to disrupt the virus, e.g.,<br>$6.54 \times 10^{-7}$ gauss 2,750 Hertz<br>Above 1 kHz electric fields are sharply attenuated by the cell membrane.<br>$5.89 \times 10^{-19}$ grams $\cdot$ $9 \times 10^{20}$ $cm^2/s^{-2}$ = $6.54 \times 10^{-7}$ gauss $\cdot$ $3 \times 10^6$ $cms^{-1}$ $\cdot$ 30 cm |

353,000 Daltons is a larger target in a virus or bacterium, yet one sees a practical association of the B field with conductive bodies or vessels containing fluids with pathogens. The frequency will be disruptive while energizing of large aggregates in the pathogen will be continuously vibrated for about an hour by the skilled worker.

After usage of the values set forth in 2(D) above renormalization of the magnetic profile of the fluid or conductive body therein resonated should be accomplished. For general human and animal consumption a range of $3.4\times10^{-8}$ gauss at a frequency of 0.952 Hz to $1.5\times10^{-7}$ gauss at a frequency of 4.2 Hz may be used safely from an effect ranging from relaxing to stimulating respectively.

The present invention also provides a preferred apparatus for applying electromagnetic fields to water as described above. This device is referred to as "The Jacobson Resonator" or the "Resonator". The apparatus is comprised of a signal generator, an attenuator unit, a set of simplified Helmholtz coils, and an application device on which the water to be treated is placed. In order to minimize the distortions of the generated magnetic field, no ferrous metals are utilized in the construction of the coils, application device, and support stand. Some minimal amounts of ferrous metals are used in the construction of an actual embodiment of the Resonator. For example, referring to FIG. 10, a bolt (121) on the swivel clamp (123), and the swivel wheels (125) were made of ferrous materials due to strength requirements and cost consideration. However, field uniformity was not significantly affected by this small amount of ferrous metal.

The Jacobson Resonator uses a signal generator to produce a magnetic field. The signal generator produces a magnetic field of the desired amplitude and frequency. In a preferred embodiment, the signal generator is an HP 3325B signal generator manufactured by the Hewlett-Packard Company which is capable of producing signals varying in frequency from DC to approximately 20 Megahertz (Mhz) in square, sinusoidal, and triangle waveforms. The generator is also capable of generating amplitudes from 1 millivolt to 10 volts into a 50 ohm load termination. In order to maintain correct signal relationship, the signal generator should be terminated into a 50 ohm load termination during operation.

Referring to FIG. 11, (see diagram for clarity) the attenuator unit (1) uses the signal produced by the signal generator to drive the helmholtz coils. The circuitry is designed to provide impedance matching to the generator and selectable attenuation of the signal. The attenuation range is from 10 milli gauss to 1 atto gauss by combining the generator range and the attenuator selection ranges. The attenuator (1) has two switches (2), one rotary switch for milli ($10^{-3}$), micro ($10^{-6}$), and nano ($10^{-9}$) selections and one toggle switch (3) for inducing an additional micro ($10^{-6}$) level of attenuation to the above signal levels. This provides for a total of $10^{-15}$ signal attenuation. All coils should never be connected directly to the signal generator, as magnetic fields in the gauss range are possible depending on the generator settings.

The magnetic fields are produced by simplified helmholtz coils. The coils may be 18 inches or 7 feet in diameter with a separation of 9 inches or 3.5 feet respectively. The smaller coils (117) are shown in FIG. 10. These coils are preferably made of 5 turns of #37 gauge wire around an 18 inch disc made of laminated foam. Additionally, the discs have an epoxy coating, for additional strength, and a black gloss enamel finish. Coil interconnections are made via two pin friction fit connectors (127) for ease of mating.

Still referring to FIG. 11, the application device (115) provides the correct separation and mounting for the coils (117). The device is capable of 180° rotation and 90° pivoting. The application device also has an epoxy coating, for additional strength and rigidity, and a black gloss enamel finish. System interconnections are made via two pin friction fit connectors (119) for ease of mating. All connections are keyed to maintain correct polarity of the coils and the field.

The support stand provides 360° rotation of the device with vertical and horizontal movement of approximately 3 feet and the ability to secure the device in any position. This provides extreme versatility in positioning and securing the device. In one embodiment, the support stand is fabricated from PVC with brass hardware for interconnecting the sub-assemblies.

Using the Jacobson Resonator described above, it is believed that the following settings provide beneficial restructuring of water and/or other ingestible substances for application to humans. For Table 4, the Jacobson Resonator is using the "Microgauss" setting and various targets are listed in the first column. In column 2 of Table 3, the amplitude setting is listed which corresponds to a flux density produced by the resonator. The third and fourth columns, respectively, represent the frequencies e⁻ and p⁺. frequency e⁻ represents the corresponding Jacobson Resonance and ion cyclotron resonance frequency when q is the gyromagnetic ratio of the electron and frequency p⁺ corresponds to q/2 πm of the proton, in the formula $f_{ICR\text{-}JR}$=qB/2 πm These tables can be used generally with other EM devices when converted into general terms. These settings are for the resonator but can be converted generally. For example, 10V=10 μG (microgauss)=1×10⁻⁶ gauss or 0.7V=0.7× 10⁻⁶ G=7×10⁻⁷ gauss.

TABLE 4

(Human Length (L) = 1.7 × 10² cm.)

| Includes harmonics target | Amplitude (volts) | Frequency (e⁻) | Frequency (p⁺) |
|---|---|---|---|
| virus (whole) | 10 V – 1 × 10⁻⁶ gauss | 279.9 Hz | .15 Hz |
|  | 9 | 251 | .135 |
|  | 8.8 | 246 | .132 |
|  | 7 | 197 | .1 |
| Interferon | 6.35 | 178 | .095 |
| Growth factors | 5.15 | 144 | .077 |
| Enzymes | 4.55 | 126 | .067 |
| Motor proteins | 3.42 – 3.42 × 10⁻⁶ gauss | 95.8 | .0513 |
| calmodulin | 2.83 | 78 | .042 |
| NGF | 2.54 | 71 | .038 |
| kinesine | .997 | 27.9 | .015 |
| Map Spectrin | .84 | 23.5 | .0126 |
| brain specific fodrin | .7 – 7 × 10⁻⁷ gauss | 19.6 | .01 |
| neurofilaments | .57 | 15.99 | .0085 |
|  | .457 | 12.8 | .0069 |
|  | .343 | 9.59 | .0051 |
|  | .33 | 9.24 |  |
|  | .32 | 8.96 |  |
|  | .31 | 8.68 |  |
| Transforming DNA (oncogenes) | .3 | 8.4 |  |
| homeoboxes | .274 | 7.677 | .0041 |
| hemoglobin | .2 | 5.6 | .003 |
|  | .19467 | 5.448 |  |
|  | .192 | 5.36 | .0028 |
|  | .175 | 4.9 |  |
|  | .162 | 4.53 | .00243 |
| BGF,tubulin single rope (homeobox) | .15 – 1.5 × 10⁻⁷ gauss | 4.2 | .0023 |
|  | .137 | 3.84 |  |
|  | .126 | 3.5 | .0019 |
| leukotrine | .1 | 2.798 | .0015 |
| PDGF, interferon | .09 | 2.52 | .00135 |
|  | .085 | 2.38 | .00127 |
|  | .081 | 2.27 |  |
| NGF | .078 | 2.1 |  |
|  | .0667 | 2.01 |  |
|  | .06 | 1.68 |  |
| melatonin | .05 | 1.4 |  |
| calmodulin | .04 | 1.12 | (DNA repair .0005) |
| hormones, epi | .035 | .976 |  |
|  | .02 | .56 |  |
|  | .012 | .336 |  |

In Table 5, the Jacobson resonator is placed in the "Nanogauss" setting.

TABLE 5

.316 V = .316 × 1 × 10⁻⁹ gauss = 3.16 × 10⁻¹⁰ gauss

|  | 10 V = 10⁻⁸ gauss | .28 Hz |
|---|---|---|
|  | 8.6 | .24 |
|  | 7.8 | .218 |
| NGF (solar) | 5.9 | .16 |
|  | 3.5 × 10⁻⁹ gauss | .098 |
| H20 | 2.99 | .09 |
|  | 1.76 | .021 |
| Leukotrines | 1.47 | .041 |
|  | 1.195 | .033 |
|  | .895 | .025 |
| melatonin | .667 | .02 |
| serotonin | .4937 | .0138 |
| epi | .431 | .012 |
| norepi | .392 | .011 |
| dopamine | .347 | .097 |
| histamine | .316 | .0885 |
|  | 3.16 × 10⁻¹⁰ gauss |  |
|  | .0538 | .0015 |
| water | .046 | .001288 |
|  | 4.6 × 10⁻¹¹ gauss |  |

In Table 6, the Jacobson resonator is placed in the "Microgauss" setting.

TABLE 6

| | Brain grouping | |
|---|---|---|
| 30–40 minutes | .077 | 2.1 |
|  | .076 | 2.13 |
|  | .075 | 2.1 |
|  | .074 | 2.072 |
|  | .073 | 2.044 |
|  | .072 | 2.016 |
|  | .071 | 1.988 |
|  | .07 | 1.96 |
|  | .069 | 1.932 |
|  | .068 | 1.904 |
|  | .0667 | 1.8667 |
|  | .0661 | 1.864 |
|  | .065 | 1.83 |
|  | .064 | 1.8 |
| | Joint Pain Including Bone | |
| about | .2 | 5.6 |
| 40 | .15 | 4.1 |
| minutes | .126 | 3.5 |
|  | .09 | 2.5 |
|  | .078 | 2.1 |
|  | .05 | 1.4 |
|  | .034 | .97 |
| | Headache | |
| about | .038 | 1.064 |
| 40 | .034 | .976 |
| minutes | .032 | .896 |
|  | .03 | .84 |
|  | .028 | .784 |
|  | .025 | .7 |

Table 7 list various protocols which have been developed using the Jacobson Resonator for beneficially restructuring water and/or other ingestible substances for application to humans to improve the health of the person treated with the restructured water and/or other ingestible substances.

TABLE 7

DEAFNESS

| Amplitude | Frequency | Time |
|---|---|---|
| 0.077 | 2.17 | 2'5' |
| 0.076 | 2.13 | 2'5' |
| 0.075 | 2.1 | 2'5' |
| 0.074 | 2.072 | 2'5' |
| 0.073 | 2.044 | 2'5' |
| 0.072 | 2.016 | 2'5' |
| 0.071 | 1.988 | 2'5' |
| 0.070 | 1.960 | 2'5' |
| 0.069 | 1.932 | 2'5' |
| 0.068 | 1.904 | 2'5' |
| 0.067 | 1.866 | 2'5' |
| 0.066 | 1.864 | 2'5' |
| 0.065 | 1.863 | 2'5' |
| 0.064 | 1.80 | 2'5' |
| 0.034 | 0.952 | 2'5' |
| 0.033 | 0.920 | 2'5' |
| 0.032 | 0.890 | 2'5' |
| 0.031 | 0.870 | 2'5' |
| 0.030 | 0.830 | 2'5' |
| 0.029 | 0.800 | 2'5' |

TOTAL TIME: 50'

HEADACHE

| Amplitude | Frequency | Time |
|---|---|---|
| 0.038 | 1.064 | 5–15 |
| 0.037 | 1.063 | 2'5' |
| 0.036 | 1.000 | 2'5' |
| 0.035 | 0.98 | 2'5' |
| 0.034 | 0.952 | 5 |
| 0.032 | 0.890 | 2'5' |
| 0.031 | 0.870 | 2'5' |
| 0.030 | 0.830 | 2'5' |
| 0.029 | 0.800 | 2'5' |
| 0.028 | 0.784 | 2'5' |
| 0.025 | 0.700 | 2'5' |

TOTAL TIME: 40–50 min.

MIGRAINE

| Amplitude | Frequency | Time |
|---|---|---|
| 0.034 | 0.952 | 5–20 |
| 0.0335 | 0.937 | 2'5' |
| 0.033 | 0.928 | 2'5' |
| 0.0325 | 0.909 | 2'5' |
| 0.032 | 0.890 | 2'5' |
| 0.0315 | 0.882 | 2'5' |
| 0.031 | 0.870 | 2'5' |
| 0.030 | 0.830 | 2'5' |
| 0.029 | 0.800 | 2'5' |
| 0.028 | 0.780 | 2'5' |
| 0.027 | 0.750 | 2'5' |
| 0.026 | 0.728 | 2'5' |
| 0.025 | 0.700 | 2'5' |
| 0.024 | 0.670 | 2'5' |
| 0.023 | 0.640 | 2'5' |
| 0.022 | 0.620 | 2'5' |
| 0.021 | 0.590 | 2'5' |
| 0.020 | 0.560 | 2'5' |

TOTAL TIME: 47'5–55 min.

SPRAINED ANKLE

| Amplitude | Frequency | Time |
|---|---|---|
| 0.343 | 950 | 15 |
| 0.274 | 7.7 | 15 |

TABLE 7-continued

| 0.033 | 0.920 | 20' |
|---|---|---|
| 0.032 | 0.890 | 20' |

TOTAL TIME: 60–70 min.

FLU VIRUS

| Amplitude | Frequency | Time |
|---|---|---|
| 0.274 | 7.7 | 15 |
| 0.200 | 5.6 | 10 |
| 0.150 | 4.1 | 10 |
| 0.126 | 3.5 | 10 |
| 0.090 | 2.5 | 5 |
| 0.078 | 2.1 | 5 |
| 0.050 | 1.4 | 5 |
| 0.034 | 0.952 | 5 |

TENNIS ELBOW

| Amplitude | Frequency | Time |
|---|---|---|
| 0.034 | 0.952 | 15 |
| 0.274 | 7.7 | 15 |
| 0.200 | 5.6 | 5 |
| 0.150 | 4.1 | 5 |
| 0.126 | 3.5 | 5 |
| 0.090 | 2.5 | 5 |
| 0.078 | 2.1 | 5 |
| 0.050 | 1.4 | 5 |
| 0.034 | 0.952 | 5 |

TOTAL TIME: 60 min.

OSTEOARTHRITIS ROTULIANA (KNEES)

| Amplitude | Frequency | Time |
|---|---|---|
| 0.0340 | 0.952 | 15–20 |
| 0.457 | 12.8 | 5 |
| 0.343 | 9.6 | 5 |
| 0.274 | 7.7 | 5 |
| 0.200 | 5.6 | 5 |
| 0.150 | 4.2 | 5 |

TOTAL TIME: 40–45 min.

RHEUMATOID ARTHRITIS (HANDS)

| Amplitude | Frequency | Time |
|---|---|---|
| 0.034 | 0.952 | 20 |
| 0.457 | 12.8 | 10 |
| 0.343 | 9.6 | 10 |
| 0.274 | 7.7 | 10 |
| 0.200 | 5.6 | 10 |
| 0.150 | 4.1 | 10 |

TOTAL TIME: 70

WATER

| Amplitude | Frequency | Time | |
|---|---|---|---|
| 0.457 | 12.8 | 30 | SKIN, WINE, PLANTS |
| 0.075 | 2.1 | 35 | SKIN |
| 0.15 | 4.1 | 35 | LAXATIVE, PLANTS, CEMENT |
| 0.034 | 0.952 | 40 | RELAX |
| 0.15 | 4.1 | 30 | PLANTS, WINE |
| 0.075 | 2.1 | 25 | COSMETICS |
| 0.075 | 2.2 | 15 | BEER |
| 0.075 | 2.1 | 15 | CANNED FRUITS |
| .274 | 7.7 | 25 | WINE, ENERGY, PLANTS |

NEUROPATHY OF THE FOOT

| Amplitude | Frequency | Time |
|---|---|---|
| Reducing tension in tissue | | |
| .034 | .952 | 5 |
| .274 | 7.70 | 5 |
| .033 | .92 | 5 |

TABLE 7-continued

Once you go over 5 minutes, you are changing rhythms.

| Amplitude | Frequency | Time |
|---|---|---|
| .20 | 5.6 | 6 |

If pain is in the sole of metatarsals, need more # in .033 range.

| | | |
|---|---|---|
| .032 | .89 | 15 |

Does pain move from sole to heel? Use heel or bone #'s

| | | |
|---|---|---|
| .274 | 7.7 | 4–7 |

Is pain just in sole?

| | | |
|---|---|---|
| .033 | 9.8 | 8–10 |

TOTAL TIME: 44 min.

PAIN IN FOOT - Plantar Fascitis, Neuropathy, Tarsal Tunnel

| Amplitude | Frequency | Time | |
|---|---|---|---|
| FOR SOFT STRUCTURES | | | |
| .031 | .867 | 5–6 | |
| .03 | .84 | 5–6 | |
| FOR HARD STRUCTURES | | | |
| .078 | 2.1 | 5 | |
| .126 | 3.5 | 5 | |
| .15 | 4.2 | 5 | |
| .457 | 12.8 | 4–5 | If left too long, pain will increase |
| .457 | .0069 | 4–5 | |
| .57 | 15.99 | 4–5 | If too much tension builds in soft tissue, use .0085. |
| .7 | 19.6 or .01 | 3 | |
| .84 | 23.5 or .013 | 3 | |
| *Best sequence for feet | | | |
| .033 | | | |
| .274 | | | |
| .032 | | | |
| .2 | | | |
| .031 | | | |
| .15 | | | |
| .03 | | | |
| .126 | | | |
| If needed | | | |
| .343 | 9.8 | | |
| .033 | | | |
| .457 | | | |
| .032 | | | |
| .57 | | 2–3 | |
| .7 | | 2–3 | |
| .84 | | 2–3 | |
| .033 | | | |

Generally, it is better to move from low to high and keep going back and forth rather than to use big frequencies for too long. If you don't release the foot from big frequencies, you will increase the pain in the soft tissues.

PARKINSON DISEASE PROTOCOL

*If there is any pressure in the head, move to .033 ug at .92 hz until the pressure subsides or disappears.
TREAT SIDE TO SIDE

| Amplitude | Frequency | Time |
|---|---|---|
| .077 | 2.17 | 3.50 |
| .076 | 2.13 | 3.50 |
| .075 | 2.10 | 3.50 |
| .074 | 2.07 | 3.50 |

REST FOR 20–30 MINUTES
TREAT FRONT TO BACK

| | | |
|---|---|---|
| .075 | 2.10 | 3.5 |
| .074 | 2.07 | 3.50 |
| .073 | 2.04 | 3.50 |
| .072 | 2.02 | 3.50 |

TOTAL TREATMENT TIME: 28 min.

CEREBRAL PALSY PROTOCOL

| Amplitude | Frequency | Time | |
|---|---|---|---|
| .034 | .952 or .976 | 10 | *or 15 minutes UE and LE to decrease spasticity (not for brain exposure in small resonator but for focused field on limbs) |
| .033 | .92 | 10 | |
| .032 | .9 | 10 | |
| Other numbers are | | | |
| .457 | 12.8 | 1.5 | } |
| .343 | 9.6 | 1.5 | } |
| .274 | 7.7 | 1.5 | } For large resonator for full body exposure |
| .2 | 5.6 | 1.5 | } |
| .15 | 4.2 | 1.5 | } |
| .075 | 2.1 | 5.5 | } |

TOTAL TREATMENT TIME: 43 min.

Always end a .034 at .952 for 20 minutes to decrease rigidity and facilitate good sleeping. Watch carefully on head. If pressure wave develops, drop down to .075 from any number. If pressure persists, drop to .033 @ .92 for 5–10 minutes. Use .033 on head only when necessary (does not help cognition). Generally 10–12 minutes @ .075 on head is excellent.

ALZHEIMER'S DISEASE PROTOCOL

*If there is a pressure wave in the head, balance with .033 ug at .92 hz or .032 at .89 hz until the pressure subsides or disappears.

| Amplitude | Frequency | Time |
|---|---|---|
| .077 | 2.17 | 4 |
| .076 | 2.13 | 4 |
| .075 | 2.1 | 4 |
| .074 | 2.07 | 4 |

REST FOR 20–30 MINUTES

| | | |
|---|---|---|
| .075 | 2.1 | 4 |
| .074 | 2.07 | 4 |
| .073 | 2.04 | 3 |
| .072 | 2.02 | 3 |

ATTENTION DEFICIT DISORDER

| Amplitude | Frequency | Time |
|---|---|---|
| SIDE TO SIDE | | |
| .076 | 2.05 | 4 |
| .075* | 2.10 | 4 |
| .074 | 2.0 | 4 |
| REST | | 30 |
| FRONT TO BACK | | |
| .076 | 2.05 | 4 |
| .075 | 2.10 | 4 |
| .074 | 2.0 | 4 |

*MAJIC NUMBER FOR CALMING KIDS/TUNES IN NERVE GROWTH NUMBER. Some researchers use .075 @ 2 hz.

ADDITIONAL HEADACHE SETTINGS

| Amplitude | Frequency | Time |
|---|---|---|
| .038 | 1.064 | setting is rarely used; for thick, heavy skull |
| .034 | .976 | 8–10 |
| .033 | .952 | 8–10 |
| .032 | .92 | 10–30 |
| .031 | .89 | 10 |
| .03 | .84 | 5–10 |

-continued

| | | |
|---|---|---|
| .028 | .784 | 5–10 |
| .025 | .7 | 5–10 |

MIGRAINE PROTOCOL

Treat 30–40 minutes side to side then front to back
*Most headaches go away at .031 at .87

| Amplitude | Frequency | Time |
|---|---|---|
| .034 | .952 | 5–15 |

If pain decreases, leave longer at .034

| | | |
|---|---|---|
| 0.033 | .92 | 10–15 |
| .032 | .89 | 10 |
| *.031 | .87 | 10–15 |

If continues to subside, leave at .031

| | | |
|---|---|---|
| .03 | .83 | 5 |
| .029 | .8 | 5 |
| .028 | .78 | 5 |
| .027 | .75 | 5 |
| .026 | .73 | 5 |
| .025 | .7 | 5 |
| .024 | .67 | 5 |

TOTAL TREATMENT TIME: 60+

UNMOTIVATED, LOST AND APATHETIC PROTOCOL

| Amplitude | Frequency | Time | |
|---|---|---|---|
| FRONT TO BACK | | | |
| .06 | 1.68 | 8 | |
| .05 | 1.4 | 8 | |
| .0428 | 1.2 | 8* | great results for men |
| .0464 | 1.3 | 8* | great results for women |
| SIDE TO SIDE | | | |
| .075 | 2.1 | 3 | |
| .0428 | 1.2 | 7 | |

REEVALUATE. If patient's mood elevates, stop. If patient is still sluggish, do

| | | | |
|---|---|---|---|
| .075 | 2.1 | 4 | |
| .05 | 1.4 | 4 | |

If there is any pressure, go to

| | | | |
|---|---|---|---|
| .033 | .92 | until pressure is gone | |
| .0428 | 1.2 | (men | 5 |
| .0464 | 1.3 | (women) | 5 |

TOTAL TREATMENT TIME: 50 min.

TENDONITIS OF THE ELBOW (and MUSCLE SPASM)

| Amplitude | Frequency | Time | |
|---|---|---|---|
| .034 | .952 | 20 | |

It still has pain go to:

| | | | |
|---|---|---|---|
| .033 | .92 | 10–15 | |
| .343 | 9.8 | 6–8 | |
| .032 | .89 | 5–10 | *relax before going back up |
| .274 | 7.7 | 15–20 | |
| .2 | 5.6 | 5–10 | |
| .034 | .952 | 5–15 | |
| .15 | 4.2 | extra 10 minutes if necessary | |
| .034 | .952 | 20–30 | |

TOTAL TREATMENT TIME: 85 min.

Times can be cut but .034 and .274 are the critical signals. .034 at .952 is used to reduce tension. .274 at 7.7 is used to reduce pain. If pain doesn't decrease after 30–40 minutes of weak signals then try some plain numbers. A muscle spasm usually doesn't need pain numbers; but, longstanding tendonitis does after 25–30 minutes.

MIGRAINE HEADACHE PROTOCOL

| Amplitude | Frequency | Time |
|---|---|---|
| .034 | .95 | 10 |
| .033 | .92 | 10 |
| .032 | .9 | 10 |
| .031 | .87 | 10 |
| .03 | .84 | 10 |
| .027 | .72 | 10 |

TOTAL TREATMENT TIME: 50 min.

Extend treatment time on any signal that seems to work the best.

OTHER NUMBERS PARKINSON'S DISEASE, ALZHEIMERS AND MULTIPLE SCLEROSIS

| Amplitude | Frequency | Time |
|---|---|---|
| Side to Side | | |
| .077 | 2.17 | 4 |
| .076 | 2.13 | 4 |
| .075 | 2.10 | 4 |
| .074 | 2.07 | 4 |
| Front to Back | | |
| .073 | 2.04 | 4 |
| .072 | 2.02 | 4 |
| .071 | 1.99 | 4 |
| .070 | 1.96 | 4 |

32 minute treatment every other day
Treat 3 × week for 2–3 weeks then reevaluate.

ADD MORE SIGNALS

| | | |
|---|---|---|
| .069 | 1.93 | 3 |
| .068 | 1.90 | 3 |
| .067 | 1.87 | 3 |
| .066 | 1.86 | 3 |

CANCER and AIDS

Parkinson disease may possibly have pressure.
M.S. and Alzheimer's most likely will not have pressure.
Any pressure, drop to .033 or .032 until pressure goes away.

Large Resonator - full body immersion in field.

| FIELD STRENGTH (micro-gauss) | FREQUENCY (hz) | TIME (minutes) | |
|---|---|---|---|
| 1.0 ug | 27.9 hz | 1 min | 3 |
| .82 ug | 23.0 hz | 1 min | 3 |
| .72 ug | 20.16 hz | 1 min | 3 |
| .654 ug | 18.2 hz | 1 min | 2 |
| .57 ug | 16.0 hz | 1 min | 2 |
| .475 ug | 12.8 hz | 1 min | 2 |
| REST PERIOD | | 3 min | |
| .343 ug | 9.59 hz | 2 min | 3 |
| .274 ug | 7.68 hz | 5 min | 6 |
| .200 ug | 5.6 hz | 4 min | 5 |
| .175 ug | 4.9 hz | 2 min | 3 |
| REST PERIOD | | 6 min | |
| .150 ug | 4.2 hz | 6 min | 7 |
| .126 ug | 3.5 hz | 3 min | 6 |
| .115 ug | 3.15 hz | 1 min | 2 |
| .090 ug | 2.52 hz | 4 min | 5 |
| .075 ug | 2.1 hz | 8 min | 10 |
| REST PERIOD | | 10 min | |
| .050 ug | 1.4 hz | 3 min | 4 |
| .038 ug | 1.1 hz | 3 min | 4 |
| .034 ug | .976 hz | 10 min | 12 |
| .030 ug | .84 hz | 2 min | 3 |

| -continued | | | |
|---|---|---|---|
| .025 ug | .7 hz | 2 min | 3 |
| .020 ug | .56 hz | 2 min | 3 |

| Microgauss Setting |  |
|---|---|
| FOR HUMAN NERVE |  |
| 2.54 | 71 |
| 1.3 | 36 |
| .997 | 27.9 |
| .84 | 23.5 |
| .72 | 20.16 |
| .654 | 18.2 |
| .57 | 16 |
| .5157 (EGF-R) | 14.56 |
| .457 | 12.8 |
| .343 | 9.6 |
| .274 | 7.7 |
| .2 | 5.6 |
| .194 | 5.45 |
| .175 | 4.9 |
| .162 | 4.53 |
| .15 | 4.2 |
| .137 | 3.84 |
| .126 | 3.5 |
| .1 | 2.8 |
| .09 | 2.52 |

TOTAL TREATMENT TIME: 1 hour and 42.5 minutes

| Signal Protocol - 41 Signals for human nerve | |
|---|---|
| .078 | 2.1 |
| .0667 | 2.01 |
| .06 | 1.68 |
| .0589 (TGF-OC Precursor) | 1.65 |
| .05 | 1.4 |
| .04 | 1.12 |
| .038 | 1.1 |
| .034 | .976 |
| .184 | .52 |
| .1769 | .495 |
| .1168 | .3267 |

| Nanogauss Setting (32 Signals in $\eta$ G) | |
|---|---|
| 5.9 | .16 |
| 2.99 | .083 |
| 1.76 | .049 |
| .895 | .025 |
| .667 | .02 |
| .494 | .014 |
| .431 | .0121 |
| .392 | .0109 |
| .316 | .0089 |

The examples above use are based on a human length. It is also possible to use the length of a water container. As discussed above, it is also possible to use this procedure to treat organisms other than humans. For such treatment, the length of the organism at the appropriate stage of development is used. The following calculations demonstrate methodologies for determining the proper flux density and frequency for treating plants.

The four inertial velocities that have been used for calculations are as follows:

1. $3.22 \times 10^7$ cm/s—star cluster (SC)
2. $2.98 \times 10^6$ cm/s—earth orbital (EO)
3. $1.93 \times 10^6$ cm/s—solar system (SS)
4. $4.642 \times 10^4$ cm/s—earth rotational (ER)

Lengths (Samples)

($1.7 \times 10^2$ cm) 1. Human length is about 5'8" (170 cm) $L_H$ ($1.5 \times 10^1$ cm) 2. Mouse length is about 15 cm $L_M$ 3. nerve piece length—
   A) 1.5 cm—$1^{st}$ experiment in Cornell lengths of nerve pieces
   B) 2–.7 cm—$2^{nd}+3^{rd}$ experiments in Cornell Note (Samples of Calculations in Table Form are included)

| electron $q/2\pi m$ | Examples I (Plants) chlorophyll a(g) | chloroplast ~5 $\mu$m long ellipsoids |
|---|---|---|
| $2.79 \times 10^7$ Coul/gram proton $q/2\pi m$ $1.5 \times 10^4$ Coul/gram | $\dfrac{\sim 625 \text{ Daltons}}{1.67 \times 10^{-24} \text{ g} \cdot 625} = 1 \times 10^{-21}$ g $\begin{pmatrix} \text{principal photoreceptor} \\ \text{in photosynthesis} \end{pmatrix}$ $\begin{bmatrix} \text{in eukaryotes and} \\ \text{cyano Bacteria} \end{bmatrix}$ | $5 \times 10^{-6}$ m = $\boxed{5 \times 10^{-4} \text{ cm}}$ membranous subcellular organelle and site of photosynthesis |

$mx(c^2)$ $1 \times 10^{-21}$ g $\times \underset{(v)}{9 \times 10^{20}}$ cm$^2$/s$^2$ = B $\cdot 2.98 \times 10^6$ cm/s $\cdot \underset{(L)}{5 \times 10^{-4}}$ cm -continued $$\frac{9 \times 10^{-1} \text{ gcm}^2 5^2}{1.5 \times 10^3 \text{ cm}^2/\text{s}} = B;$$

$$B = 6 \times 10^{-4} \text{ gauss}$$

$$\text{ficr} = qB / n\pi m = 2.79 \times 10^7 \frac{e}{q} \cdot B;$$

$$\text{frequency} = 2.79 \times 10 \cdot 6 \times 10^{-4}$$

If $q/2 \pi m$ is for $p^+$ (proton) instead of $e^-$ (electron) then $q/2 \pi m = 1.5 \times 10^4$ c/q instead of $2.79 \times 10^7$ c/q Thus, frequency$_{(ion\ cyclotronresonance,\ ICR)} = 1.5 \times 10^4$ c/q. $6 \times 10^{-4}$ gauss $f = 9$ Hz Therefore, the protocol is:

1. $1^{st}$ week—$B = 6 \times 10^{-4}$ gauss and $f = 9$ Hz or $1.67 \times 10^4$ Hz Then, $2^{nd}$ week L could be 0.2 cm (length of seed for example)

$10^{-21}$ g×$9 \times 10^{20}$ cm$^2$s$^{-2}$=B. $2.98 \times 10^6$ cm/s. $2 \times 10^{-1}$ cm ∴ $B = 1.5 \times 10^{-6}$ gauss $$f = 2.79 \underset{(e^-)}{\times} 10^7 \cdot 1.5 \times 10^{-6} = 4.2 \times 10^1 = 42 \text{ Hz or}$$

$$f = 1.5 \times 10^4 \cdot 1.5 \times 10^{-6} = 2.25 \times 10^{-2} = .0225 \text{ Hz}$$

2. Week #2—$B = 1.5 \times 10^{-6}$ gauss at 42 Hz or 0.0225 Hz $3^{rd}$ week; L is increasing; L=2 cm (arbitrary depends upon growth cycle of plants)

$$\frac{9 \times 10^{-6}}{6 \times 10^6} = B = 1.5 \times 10^{-7} \text{ gauss}$$

$f = 4.2$ Hz $f$ or $e^-$ (protocol for plants)

| B (gauss) | f (Hz) | |
|---|---|---|
| $6 \times 10^{-4}$ | 9 | $1^{st}$ week |
| $1.5 \times 10^{-6}$ | 42 | $2^{nd}$ week |
| $1.5 \times 10^{-7}$ | 4.2 | $3^{rd}$ week through maturity of fruit |

* { See chart which has flux densities in microgauss setting with associateed frequencies based in electronic gyromagnetic ratio. } again plants Example II    seedlength/0.1 cm

--- t arg et{~600Daltonsiron protoporphyrinIX }
$1 \times 10^{-21}\ 9 \times 9 \times 10^{20}$ cm$^2$/s$^2$ = B.$4.6 \times 10^4$ cm/s.0.2 cm
(EO) (L)
seed 1.
$1^{st}$ week    $\frac{9 \times 10^{-1}}{9.2 \times 10^3} = 1 \times 10^{-4}$ gauss = B $$f = 1.5 \times 10^4 \cdot 1 \times 10^{-4} = 1.5 \text{ Hz} \begin{pmatrix} \text{using } p^+q/2\pi m \\ \text{protonic} \end{pmatrix}$$

-continued t arg et{~600Daltonsiron protoporphyrinIX }
$1 \times 10^{-21}\ 9 \times 9 \times 10^{20}$ cm$^2$/s$^2$ = B.$4.6 \times 10^4$ cm/s.0.2 cm
(EO) (L)
seed 2.
$2^{nd}$ week L → 2 cm   B = $10^{-5}$ $$f = 15 \text{ Hz} \begin{pmatrix} \text{using } p^+q/2\pi m \\ \text{protonic} \end{pmatrix}$$

3.
$3^{rd}$ week

L → 20 cm

B = $10^{-6}$ $$f = 28 \text{ Hz} \begin{pmatrix} \text{using } e^-q/2\pi m \\ \text{electronic} \end{pmatrix}$$

4.
$4^{th}$ week through duration

B = $10^{-7}$ $$f = 2.8 \text{ Hz} \begin{pmatrix} \text{using } e^-q/2\pi m \\ \text{electronic} \end{pmatrix}$$

EXAMPLE II

| B (gauss) | f (Hertz) |
|---|---|
| $1 \times 10^{-4}$ | 1.5 |
| $1 \times 10^{-5}$ | 15 Hz |
| $1 \times 10^{-6}$ | 28 Hz |
| $1 \times 10^{-7}$ | 2.8 |

* Water should be treated (resonated) for one hour and plants should be water only with resonated water from initiation to maturity of fruit.

EXAMPLE III

Dog protocol
treat racing heart syndrome (tachycardia)

| Water should be resonated for 1 hour | B (gauss) | f (Hz) | |
|---|---|---|---|
| (2 days) | $3.4 \times 10^{-8}$ | .952 | 4 signals to treat dogs with resonated water |
| (2 days) | $3.3 \times 10^{-8}$ | .92 | |
| (2 days) | $3.2 \times 10^{-8}$ | .89 | |
| (2 days) | $3.0 \times 10^{-8}$ | .80 | |

A) 8 day treatment—dogs should only be given resonated water (one signal at a time) or B) water may be treated with all four signals—20 minutes for each signal.

To treat humans with multiple signal protocols as indicated on various tables—the patient should drink either:

A) water treated with one signal at a time; in successive days as many as there are signals (1 signal for each day)

B) treat water with entire protocol at one sitting—multiple frequencies imbued in $H_2O$ (each signal should be used to resonate water for the length of time at least (20 minutes).

Table 7, below, gives an example of the settings for the Jacobson Resonator which have demonstrated beneficial nerve regeneration in mice. The information in Table 4 was determined with the Jacobson Resonator placed in the "Microgauss" setting.

TABLE 8

Nerve Regeneration In Mice

| | |
|---|---|
| .10 | 280 or .15 |
| 2.54 | 71 |
| 1.3 | 36 |
| .997 | 27.9 |
| .825 | 23 |
| .7 | 19.6 |
| .57 | 16 |
| .46 | 12.8 |
| .34 | 9.6 |
| .27 | 7.6 |
| .175 | 5.4 |
| .15 | 4.1 |
| .126 | 3.5 |
| .09 | 2.5 |

TABLE 9

Resonated Water to Enhance Plant Growth

| | Amplitude | Frequency | Time |
|---|---|---|---|
| A | 0.63 | 17.6 | 30 |
| | 0.84 | 23.5 | 30 |
| | 1.0 | 28 | 30 |
| B | .15 | 4.2 | 30 |
| | .268 | 7.5 | 30 |
| | .381 | 10.68 | 30 |
| C | 6.5 | 0.975 | 30 |
| | 4.0 | 0.6 | 30 |
| | 2.0 | 0.3 | 30 |
| D | 6.5 | 182 | 30 |
| | 4.0 | 112 | 30 |
| | 2.0 | 56 | 30 |

It should be understood that the foregoing is illustrative of the instant invention and should not be considered limitative or restrictive thereof. The scope of the invention may be further described within the scope of the attached claims.

What is claimed is:

1. A method for beneficially restructuring an ingestible substance comprising:

subjecting an ingestible substance for a period of time to an electromagnetic field of a specific flux density varying from $10^{-5}$ to $10^{-21}$ gauss and a specific frequency varying from 0 hertz to 300 hertz depending on the intended subsequent use of said ingestible substance, wherein said specific flux density and said specific frequency has been empirically determined to restructure said ingestible substance such that said ingestible substance beneficially affects the organism to which the ingestible substance is subsequently applied.

2. The method of claim 1, wherein said ingestible substance is at least one of an aqueous mixture, a sports drink, a geriatric drink, an electrolyte drink, a neutraceutical, a pharmaceutical, a medicinal formulation, a cream, a lotion, and an alcoholic beverage.

3. The method of claim 1, further comprising calculating said electromagnetic field to impinge upon said ingestible substance in a manner which is directly correlated to target masses in biosystems.

4. The method of claim 3, further comprising after subjecting said ingestible substance to said electromagnetic field of a specific flux density and specific frequency corresponding to a particular target, repeating subjecting said electromagnetic field of a specific flux density and specific frequency for each of a plurality of targets.

5. The method of claim 1, further comprising generating said electromagnetic field using a solenoid to which electric power has been applied.

6. The method of claim 1, further comprising generating said electromagnetic field using helmholts coils to which electric power has been applied.

7. The method of claim 1, further comprising generating said electromagnetic field using poloidal magnets to which electric power has been applied.

8. The method of claim 1, further comprising generating said electromagnetic field using toroidal coils to which electric power has been applied.

9. A method for restructuring an ingestible substance, comprising:

subjecting an ingestible substance to an electromagnetic field of a specific flux density varying from $10^{-5}$ to $10^{-21}$ gauss and a specific frequency varying from 0 hertz to 300 hertz depending on the intended subsequent use of said ingestible substance, wherein said specific flux density and said specific frequency being calculated using the formula $mc^2=Bvlq$, wherein m equals a mass of one of a plurality of targets;

c equals the speed of light;

v equals the inertial velocity of said mass;

l equals length of the organism to which the water will be applied; and q equals unity of charge, to thereby determine a magnetic flux density (B).

10. The method of claim 9, wherein said ingestible substance is at least one of an aqueous mixture, a sports drink, a geriatric drink, an electrolyte drink, a neutraceutical, a pharmaceutical, a medicinal formulation, a cream, a lotion, and an alcoholic beverage.

11. The method of claim 9, further comprising calculating said electromagnetic field to impinge upon the ingestible substance in a manner which is directly correlated to target masses in biosystems.

12. The method of claim 11, further comprising after subjecting said ingestible substance to said electromagnetic field of a specific flux density and specific frequency corresponding to a particular target, repeating subjecting said electromagnetic field of a specific flux density and specific frequency for each of a plurality of targets.

13. The method of claim 9, further comprising generating said electromagnetic field using a solenoid to which electric power has been applied.

14. The method of claim 9, further comprising generating said electromagnetic field using helmholts coils to which electric power has been applied.

15. The method of claim 9, further comprising generating said electromagnetic field using poloidal magnets to which electric power has been applied.

16. The method of claim 9, further comprising generating said electromagnetic field using toroidal coils to which electric power has been applied.

17. The method of claim 14, further comprising arranging said coils such that each of the coils have equal diameters and the distance between the coils is about equal to the radius of each of the coils such that upon applying power to said coils, a relatively uniform magnetic field exists between the coils.

18. The method of claim 9, further comprising generating said electromagnetic field using plates to which electric power has been applied.

\* \* \* \* \*

UNITED STATES PATENT AND TRADEMARK OFFICE
CERTIFICATE OF CORRECTION

PATENT NO. : 6,733,434 B2
DATED : May 11, 2004
INVENTOR(S) : Jerry I. Jacobson

It is certified that error appears in the above-identified patent and that said Letters Patent is hereby corrected as shown below:

Title page,
Item [56], References Cited, U.S. PATENT DOCUMENTS, please insert the following:
-- 781,448--------1/1905---McIntyre
   2,099,511---11/1937---Caesar
   2,103,440---12/1937---Weissenberg
   3,738,369---06/1973---Adams et al.
   3,890,953---06/1975---Kraus
   4,323,056---04/1982---Borrelli
   4,576,172---03/1986---Bentall
   4,611,599---09/1986---Bentall
   5,269,746---12/1993---Jacobson
   5,366,435---11/1994---Jacobson --

FOREIGN PATENT DOCUMENTS, please insert the following:
-- AU-B-45680/89---6/1990---Jacobson
   EP 0 371 504 A2--6/1990—Jacobson --

OTHER PUBLICATIONS, please insert the following:
-- Adey, W.R., Physiological Signalling Across Cell Membranes and Cooperative Influences of Extremely Low Frequency Electromagnetic Fields, Biological Coherence and Response to External Stimuli, (1988), 148-170.

Adey, W.R., Tissue Interactions With Nonionizing Electromagnetic Fields, Physiological Reviews, (1981), Vol. 61, No. 2, 435-514.

Anninos, P.A. et al., Magnetic Stimulation in the Treatment of Partial Seizures, Intern J. Neuroscience, Vol. 60, (1991), 141-171.

Anninos, P.A. et al., The Biological Effects of Magnetic Stimulation in Epileptic Patients, PanMinerva Med, Vol. 41, No. 3, (1999), 207-215.

Beall, P.T. et al., Distinction of Normal, Preneoplastic, and Neoplastic Mouse Mammary Primary Cell Cultures by Water Nuclear Magnetic Resonance Relaxation Times, JNCI, (1980), Vol. 64, No. 2, 335-338.

Bistolfi, F., Biostructures and Radiation Order Disorder, Edizioni Minerva Medica, Toreno (1991).

Clegg, J.S., Intracellular Water and the Cytomatrix: Some Methods of Study and Current Views, The Journal of Cell Biology, (1984), Vol. 99, No.1, Part 2, 167-171.

Clegg, J.S. Intracellular Water, Metabolism and Cell Architecture: Part 2, Coherent Excitations in Biological Systems, (1983), 162-177.

Clegg, J.S., Properties and Metabolism of the Aqueous Cytoplasm and its Boundaries, American Journal of Physiology, 246:R-136.

Cohen, D., Magnetoencephalography: Detection of the Brain's Electrical Activity with a Superconducting Magnetometer, Science, (1972), Vol. 175, 664-666.

Egan, T.F., Molecular Basis of Contrast in MRI, Cell Function and Disease, Plenum Press 1988.

Eichhorn, G.L., Aging, Genetics, and the Environment: Potential of Errors Introduced Into Genetic Information Transfer by Metal Ions, Mechanisms of Ageing and Development (1979), Vol. 9, 291-301.

Hazlewood, C.F., Implications of Cellular Water in Health and Disease, Second Advanced Water Sciences Symposium, Section 3, Page I.

Hazlewood, C.F., A Role for Water in the Exclusion of Cellular Sodium - Is a Sodium Pump Needed? Cardiovascular Diseases, Bulletin of the Texas Heart Institute, (1975), Vol. 2, No. 1, 83-103.

UNITED STATES PATENT AND TRADEMARK OFFICE
CERTIFICATE OF CORRECTION

PATENT NO. : 6,733,434 B2
DATED : May 11, 2004
INVENTOR(S) : Jerry I. Jacobson

It is certified that error appears in the above-identified patent and that said Letters Patent is hereby corrected as shown below:

OTHER PUBLICATIONS, (cont)

Hazlewood, C. F., A View of the Significance and Understanding of the Physical Properties of Cell-Associated Water, Baylor College of Medicine, Academic Press, Inc., NY,(1979), 165-259.

Hazlewood, C.F. et al., Diffusion of Water in Tissues and MRI, Magnetic Resonance in Medicine,(1991), Vol. 19, 214-216.

Jacobson, J. I., The Coupling Mechanism for Weak Electromagnetic Fields: Bioeffects and a New Way to Approach Magnetotherapy, PanMinerva Medica, (1993), Vol.36, 34-41.

Jacobson, J. I., Exploring the Potential of Magneto-Recrystallization of Genes and Associated Structures with Respect to Nerve Regeneration and Cancer, International Journal of Neuroscience, (1992), Vol.64, 153-165.

Jacobson, J.I., Is the Fusion Process the Basis for Growth, Repair and Aging?, Quarterly Review of European Medicine Official Journal of the Italian Medical Association Official Journal of "Europa Medica", (1990), Vol. 32, 132-140.

Jacobson, J.I., Jacobson Resonance: The Quantum-Mechanical Basis for a Novel Radiological Approach to Treating Cancer and AIDS, Frontier Perspectives, (1996), Vol. 6, No. 1, 17-26.

Jacobson, J.I., Jacobson Resonance is the Basis from Which to Evaluate Potential Hazard and Therapeutic Benefit from Extrinsic Magnetic Fields, PanMinerva Medica, (1993), Vol.35, 138+14.

Jacobson, J. I., A Look at the Possible Mechanism and Potential of Magnotherapy, Journal of Theoretical Biology, (1991), Vol. 148, 97-120.

Jacobson, J.I., Physics in Medicine: A Potential Unfolding in the Radiological Sciences, PanMinerva Medica, (1997), Vol. 39, No. 2, 111-127.

Jacobson, J.I., Pineal-hypothalamic Tract Mediation of Picotesla Magnetic Fields in the Treatment of Neurological Disorders, Panminerva Medica, (1994), Vol. 36, No. 4, 201-205.

Sandyk, R., Successful Treatment of Multiple Sclerosis with Magnetic Fields, Intern J .Neuroscience, (1992), Vol. 66, 237-250.

Seitz, P.K. et al., Proton Magnetic Resonance Studies on the Physical State of Water in Artemia Cysts The Brine Shrimp Artemia, (1980), Vol. 2, Physiology,Biochemistry, Molecular Biology, 545-554.

Welker, H.A et al., Effects of an Artificial Magnetic Field on Serotonin N-Acetyltransferase Activity and Melatonin Content of the Rat Pineal Gland, Experimental Brain Research, (1983), Vol. 50, 426-432.

Column 33,
Line 17, the phrase "$cm^2s^2$" should read -- $cm^2s^{-2}$ --.
Lines 62-63, the phrase that reads "Sympathetic, Electronic Resonance at 0.15 Hz is associated with 5.36x10 gauss (B)" should be deleted.

Column 33, line 65 to Column 34, line 9,
The paragraph that reads "the range for parasympathetic stimulation ...resonance at about a few microgauss" should be deleted.

UNITED STATES PATENT AND TRADEMARK OFFICE
CERTIFICATE OF CORRECTION

PATENT NO. : 6,733,434 B2
DATED : May 11, 2004
INVENTOR(S) : Jerry I. Jacobson

It is certified that error appears in the above-identified patent and that said Letters Patent is hereby corrected as shown below:

<u>Column 52,</u>
Line 44, the word "water" should read -- ingestible substance --

Signed and Sealed this

Fifth Day of April, 2005

JON W. DUDAS
*Director of the United States Patent and Trademark Office*